(12) United States Patent
Garalde et al.

(10) Patent No.: US 10,480,026 B2
(45) Date of Patent: Nov. 19, 2019

(54) METHOD FOR NANOPORE RNA CHARACTERISATION

(71) Applicant: Oxford Nanopore Technologies Ltd., Oxford (GB)

(72) Inventors: Daniel Ryan Garalde, Oxford (GB); Andrew John Heron, Oxford (GB); Lakmal Jayasinghe, Oxford (GB); Daniel John Turner, Oxford (GB); James White, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 75 days.

(21) Appl. No.: 15/519,599

(22) PCT Filed: Oct. 19, 2015

(86) PCT No.: PCT/GB2015/053097
§ 371 (c)(1),
(2) Date: Apr. 17, 2017

(87) PCT Pub. No.: WO2016/059436
PCT Pub. Date: Apr. 21, 2016

(65) Prior Publication Data
US 2017/0253923 A1      Sep. 7, 2017

Related U.S. Application Data

(63) Continuation-in-part of application No. PCT/GB2015/052916, filed on Oct. 6, 2015.

(30) Foreign Application Priority Data

Oct. 17, 2014   (GB) .................................. 1418459.2
May 14, 2015   (GB) .................................. 1508270.4
Oct. 6, 2015   (GB) .................................. 1517634

(51) Int. Cl.
C12Q 1/6869   (2018.01)
C12N 9/14     (2006.01)
G01N 27/447   (2006.01)

(52) U.S. Cl.
CPC ............. *C12Q 1/6869* (2013.01); *C12N 9/14* (2013.01); *C12Y 306/04012* (2013.01); *G01N 27/44791* (2013.01)

(58) Field of Classification Search
None
See application file for complete search history.

(56) References Cited

U.S. PATENT DOCUMENTS 5,576,204 A    11/1996   Blanco et al.
6,426,231 B1   7/2002    Bayley et al.
(Continued)

FOREIGN PATENT DOCUMENTS

WO   WO 2008/124107   10/2008
WO   WO 2010/004265   1/2010
(Continued)

OTHER PUBLICATIONS

Shin et al, J. Biol. Chem., vol. 281, pp. 16914-16921, published online Jul. 5, 2006. (Year: 2006).*

(Continued)

*Primary Examiner* — Robert T. Crow
(74) *Attorney, Agent, or Firm* — Wolf, Greenfield & Sacks, P.C.

(57) ABSTRACT

The invention relates to a new method of characterizing a target RNA polynucleotide by taking one or more measurements as the target RNA polynucleotide moves with respect to a transmembrane pore. The movement is controlled by a DNA helicase. The invention also relates to a modified RNA (Continued)

construct wherein the RNA polynucleotide has been modified to increase DNA helicase binding thereto.

32 Claims, 22 Drawing Sheets

Specification includes a Sequence Listing.

(56) References Cited

U.S. PATENT DOCUMENTS

| | | | |
|---|---|---|---|
| 6,617,113 | B2 | 9/2003 | Deamer et al. |
| 8,105,846 | B2 | 1/2012 | Bayley et al. |
| 8,828,208 | B2 | 9/2014 | Canas et al. |
| 9,057,102 | B2 | 6/2015 | Turner et al. |
| 9,546,400 | B2 | 1/2017 | Turner et al. |
| 9,551,023 | B2 | 1/2017 | Turner et al. |
| 9,556,480 | B2 | 1/2017 | Turner et al. |
| 9,678,056 | B2 | 6/2017 | Turner et al. |
| 9,738,929 | B2 | 8/2017 | Turner et al. |
| 9,995,728 | B2 | 6/2018 | Fordham et al. |
| 2002/0197618 | A1 | 12/2002 | Sampson |
| 2004/0058378 | A1* | 3/2004 | Kong .............. C12Q 1/6844 435/6.12 |
| 2005/0014162 | A1 | 1/2005 | Barth et al. |
| 2007/0224613 | A1 | 9/2007 | Strathmann |
| 2010/0196203 | A1 | 8/2010 | Sanghera et al. |
| 2010/0291548 | A1 | 11/2010 | Sharaf et al. |
| 2011/0120871 | A1 | 5/2011 | Reid et al. |
| 2011/0121840 | A1 | 5/2011 | Sanghera et al. |
| 2011/0177498 | A1 | 7/2011 | Clarke et al. |
| 2011/0229877 | A1 | 9/2011 | Jayasinghe et al. |
| 2012/0058468 | A1 | 3/2012 | Mckeown |
| 2012/0100530 | A1 | 4/2012 | Moysey et al. |
| 2012/0107802 | A1 | 5/2012 | Stoddart et al. |
| 2012/0322679 | A1 | 12/2012 | Brown et al. |
| 2013/0116130 | A1 | 5/2013 | Fu et al. |
| 2014/0051069 | A1 | 2/2014 | Jayasinghe et al. |
| 2014/0186823 | A1 | 7/2014 | Clarke et al. |
| 2014/0234834 | A1* | 8/2014 | Di Pasquale ........ C12Q 1/6851 435/6.11 |
| 2014/0296083 | A1 | 10/2014 | Brown et al. |
| 2015/0008126 | A1 | 1/2015 | Maglia et al. |
| 2015/0031020 | A1 | 1/2015 | Jayasinghe et al. |
| 2015/0152492 | A1 | 6/2015 | Brown et al. |
| 2015/0177237 | A1 | 6/2015 | Turner et al. |
| 2015/0247183 | A1 | 9/2015 | Turner et al. |
| 2015/0301015 | A1 | 10/2015 | Fordham et al. |
| 2016/0010147 | A1 | 1/2016 | Heron et al. |
| 2016/0251710 | A1 | 9/2016 | Brown et al. |
| 2016/0257942 | A1 | 9/2016 | Bruce et al. |

FOREIGN PATENT DOCUMENTS

| | | | |
|---|---|---|---|
| WO | WO 2010/004273 | | 1/2010 |
| WO | WO 2010/109197 | | 9/2010 |
| WO | WO 2010/122293 | | 10/2010 |
| WO | WO 2011/067559 | | 6/2011 |
| WO | WO 2011/103424 | A2 | 8/2011 |
| WO | WO 2012/009578 | | 1/2012 |
| WO | WO 2012/033524 | | 3/2012 |
| WO | WO 2012/088339 | A2 | 6/2012 |
| WO | WO 2012/107778 | A2 * | 8/2012 ........... C12Q 1/6869 |
| WO | WO 2012/129242 | A2 | 9/2012 |
| WO | WO 2012/164270 | A1 | 12/2012 |
| WO | WO 2013/014451 | A1 | 1/2013 |
| WO | WO 2013/057495 | A2 | 4/2013 |
| WO | WO 2013/098561 | A1 | 7/2013 |
| WO | WO 2013/098562 | A2 | 7/2013 |
| WO | WO 2013/121201 | | 8/2013 |
| WO | WO 2013/153359 | A1 | 10/2013 |
| WO | WO 2014/013259 | A1 | 1/2014 |
| WO | WO 2014/013260 | A1 | 1/2014 |
| WO | WO 2014/013262 | A1 | 1/2014 |
| WO | WO 2014/041337 | A1 | 3/2014 |
| WO | WO 2014/072703 | A1 | 5/2014 |
| WO | WO 2014/135838 | A1 | 9/2014 |
| WO | WO 2015/055981 | A2 | 4/2015 |
| WO | WO 2015/056028 | A1 | 4/2015 |
| WO | WO 2015/110777 | A1 | 7/2015 |
| WO | WO 2015/150786 | A1 | 10/2015 |

OTHER PUBLICATIONS

Ayub et al., Individual RNA base recognition in immobilized oligonucleotides using a protein nanopore. Nano Lett. Nov. 14, 2012;12(11):5637-43. doi: 10.1021/nl3027873. Epub Oct. 19, 2012.
Chandler et al., Membrane surface dynamics of DNA-threaded nanopores revealed by simultaneous single-molecule optical and ensemble electrical recording. Langmuir. Feb. 3, 2004;20(3):898-905.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Deamer, Nanopore analysis of nucleic acids bound to exonucleases and polymerases. Annu Rev Biophys. 2010;39:79-90. doi:10.1146/annurev.biophys.093008.131250.
Gu et al., Single molecule sensing by nanopores and nanopore devices. Analyst. Mar. 2010;135(3):441-51. doi: 10.1039/b907735a. Epub Dec. 22, 2009.
Holden et al., Direct introduction of single protein channels and pores into lipid bilayers. J Am Chem Soc. May 11, 2005;127(18):6502-3.
Hornblower et al., Single-molecule analysis of DNA-protein complexes using nanopores. Nat Methods. Apr. 2007;4(4):315-7. Epub Mar. 4, 2007.
Ivanov et al., DNA tunneling detector embedded in a nanopore. Nano Lett. Jan. 12, 2011;11(1):279-85. doi: 10.1021/nl103873a. Epub Dec. 6, 2010.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Movileanu, Interrogating single proteins through nanopores: challenges and opportunities. Trends Biotechnol. Jun. 2009;27(6):333-41. doi:10.1016/j.tibtech.2009.02.008. Epub Apr. 23, 2009.
Nikolov et al., Behavior of giant vesicles with anchored DNA molecules. Biophys J. Jun. 15, 2007;92(12):4356-68. Epub Mar. 23, 2007.
Pfeiffer et al., Bivalent cholesterol-based coupling of oligonucletides to lipid membrane assemblies. J Am Chem Soc. Aug. 25, 2004;126(33):10224-5.
Rotem et al., Protein detection by nanopores equipped with aptamers. J Am Chem Soc. Feb. 8, 2012;134(5):2781-7. doi:10.1021/ja2105653. Epub Jan. 26, 2012.
Shim et al., Single-molecule detection of folding and unfolding of the G-quadruplex aptamer in a nanopore nanocavity. Nucleic Acids Res. Feb. 2009;37(3):972-82. doi: 10.1093/nar/gkn968. Epub Dec. 26, 2008.
Soni et al., Synchronous optical and electrical detection of biomolecules traversing through solid-state nanopores. Rev Sci Instrum. Jan. 2010;81(1):014301. doi: 10.1063/1.3277116.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Tian et al., Designing a polycationic probe for simultaneous enrichment and detection of microRNAs in a nanopore. ACS Nano. May 28, 2013;7(5):3962-9. doi: 10.1021/nn305789z. Epub Apr. 10, 2013.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.

(56) References Cited

OTHER PUBLICATIONS

Venkatesan et al., Nanopore sensors for nucleic acid analysis. Nat Nanotechnol. Sep. 18, 2011;6(10):615-24. doi: 10.1038/nnano.2011.129.
Wang et al., Nanopore-based detection of circulating microRNAs in lung cancer patients. Nat Nanotechnol. Sep. 4, 2011;6(10):668-74. doi: 10.1038/nnano.2011.147.
United States District Court for the District of Delaware Order. *Pacific Biosciences of California, Inc. v. Oxford Nanopore Technolgoies, Inc.* Civil Action No. 17-275-RGA. Nov. 9, 2017.
Case 1:17-cv-01353-LPS Document 15. Plaintiff's response to Oxford Nanopore Techologies, Inc.'s Motion to Dismiss and Request for Scheduling Conference. Nov. 30, 2017.
Case 1:17-cv-01353-LPS Document 13. First Amended Complaint for Patent Infringement. Nov. 30, 2017.
Case 1:17-cv-01353-RGA Document 10. Oxford's opening brief in support of its motion to partially dismiss Pacbio's complaint for patent infringement. Nov. 16, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-LPS Document 18. Notice of subsequent events relating to Oxford's motion to dismiss (D.I. 9). Oct. 18, 2017.
Case 1:17-cv-00275-RGA Document 16. Oxford's reply brief in support of its motion to dismiss PacBio's complaint for patent infringement. Jun. 26, 2017.
Case 1:17-cv-00275-RGA Document 14. PacBio's response to Oxford's motion to dismiss. Jun. 5, 2017.
Case 1:17-cv-00275-RGA Document 10. Oxford's opening brief in support of its motion to dismiss PacBio's complaint for patent infringement. May 8, 2017.
PCT/GB2015/053097, Dec. 18, 2015, International Search Report and Written Opinion
PCT/GB2015/053097, Apr. 27, 2017, International Preliminary Report on Patentability.

\* cited by examiner

SEQUENCE LISTING

<160> NUMBER OF SEQ ID NOS: 72

<210> SEQ ID NO 1
<211> LENGTH: 558
<212> TYPE: DNA
<213> ORGANISM: Artificial Sequence
<220> FEATURE:
<223> OTHER INFORMATION: Synthetic polynucleotide

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
```

```
ccgtggaata tgaactaa                                                      558
```

<210> SEQ ID NO 2
<211> LENGTH: 184
<212> TYPE: PRT
<213> ORGANISM: Artificial Sequence
<220> FEATURE:
<223> OTHER INFORMATION: Synthetic polypeptide

<400> SEQUENCE: 2

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 3
<211> LENGTH: 885
<212> TYPE: DNA
<213> ORGANISM: Artificial Sequence
<220> FEATURE:
<223> OTHER INFORMATION: Synthetic polynucleotide

<400> SEQUENCE: 3

```
atggcagatt ctgatattaa tattaaaacc ggtactacag atattggaag caatactaca     60
gtaaaaacag gtgatttagt cacttatgat aaagaaaatg gcatgcacaa aaagtatttt    120
tatagtttta tcgatgataa aaatcacaat aaaaaactgc tagttattag aacaaaaggt    180
accattgctg gtcaatatag agtttatagc gaagaaggtg ctaacaaaag tggtttagcc    240
tggccttcag cctttaaggt acagttgcaa ctacctgata tgaagtagc tcaaatatct     300 gattactatc aagaaattc gattgataca aaaaactata tgagtacttt aacttatgga    360
ttcaacggta atgttactgg tgatgataca ggaaaaattg gcggcttat tggtgcaaat    420 gtttcgattg gtcatacact gaactatgtt caacctgatt tcaaaacaat tttagagagc    480
ccaactgata aaaagtagg ctggaaagtg atatttaaca atatggtgaa tcaaaattgg    540
ggaccatacg atcgagattc ttggaacccg gtatatggca tcaacttttt catgaaaact    600
```

```
agaaatggtt ctatgaaagc agcagataac ttccttgatc ctaacaaagc aagttctcta      660
ttatcttcag ggttttcacc agacttcgct acagttatta ctatggatag aaaagcatcc      720
aaacaacaaa caaatataga tgtaatatac gaacgagttc gtgatgatta ccaattgcat      780
tggacttcaa caaattggaa aggtaccaat actaaagata atggacaga tcgttcttca       840 gaaagatata aaatcgattg ggaaaaagaa gaaatgacaa attaa                      885
```

<210> SEQ ID NO 4
<211> LENGTH: 293
<212> TYPE: PRT
<213> ORGANISM: Artificial Sequence
<220> FEATURE:
<223> OTHER INFORMATION: Synthetic polypeptide

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 5

<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Val Ala Val
    130                 135                 140

Ser Asn Ala His Gly Thr Val Thr Gly Ala Ala Gly Gly Val Leu Leu
145                 150                 155                 160

```
Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 7
<211> LENGTH: 183
<212> TYPE: PRT
<213> ORGANISM: Mycobacterium smegmatis

<400> SEQUENCE: 7

```
Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180
```

<210> SEQ ID NO 8
<211> LENGTH: 760
<212> TYPE: PRT
<213> ORGANISM: Methanococcoides burtonii

<400> SEQUENCE: 8

```
Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110
```

Val Asn Asp Ile Ile Val Ala Thr Ser Glu Lys Thr Asp Ser Leu Leu
    115                 120                 125

Arg Asn Gly Thr Ser Trp Met Asp Glu Ile Thr Thr Val Val Val Asp
130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
        435                 440                 445

Gly Ala Thr Phe Phe Ala Tyr Gln Gln Asp Lys Trp Met Leu Glu Glu
    450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

```
Asn Met Gly Ser Leu Glu Asp Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
        595                 600                 605

Glu Trp Val Thr Glu Val Ser Ala Glu Asp Ile Thr Arg His Phe Asn
610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
        675                 680                 685

Arg Lys Leu Tyr Asn Ala Gly Phe Val Ser Val Ala Lys Leu Lys Gly
690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760

<210> SEQ ID NO 9
<211> LENGTH: 707
<212> TYPE: PRT
<213> ORGANISM: Cenarchaeum symbiosum

<400> SEQUENCE: 9

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Pro Asp Trp Met Asp Glu Val Gly
    130                 135                 140
```

```
Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
                180                 185                 190

Ala Gly Trp Leu Asp Cys Thr Leu Val His Ser Thr Trp Arg Pro Val
            195                 200                 205

Pro Leu Ser Glu Gly Val Tyr Gln Asp Gly Glu Val Ala Met Gly Asp
            210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                    245                 250                 255

Asp Thr Arg Ala Arg Ser Ala Ser Leu Ala Ala Lys Ala Ser Ala Val
                260                 265                 270

Ile Pro Glu Ala Lys Gly Ala Asp Ala Ala Lys Leu Ala Ala Ala Ala
            275                 280                 285

Lys Lys Ile Ile Ser Ser Gly Gly Glu Thr Lys Leu Ala Lys Thr Leu
            290                 295                 300

Ala Glu Leu Val Glu Lys Gly Ala Ala Phe His His Ala Gly Leu Asn
305                 310                 315                 320

Gln Asp Cys Arg Ser Val Val Glu Glu Phe Arg Ser Gly Arg Ile
                325                 330                 335

Arg Leu Leu Ala Ser Thr Pro Thr Leu Ala Ala Gly Val Asn Leu Pro
                340                 345                 350

Ala Arg Arg Val Val Ile Ser Ser Val Met Arg Tyr Asn Ser Ser Ser
                355                 360                 365

Gly Met Ser Glu Pro Ile Ser Ile Leu Glu Tyr Lys Gln Leu Cys Gly
            370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
            435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
                500                 505                 510

Leu Arg Asp Ala Val Gly Glu Ala Ser Pro Gly Arg Met His Thr Leu
                515                 520                 525

Gly Phe Leu His Leu Val Ser Glu Cys Ser Glu Phe Met Pro Arg Phe
            530                 535                 540

Ala Leu Arg Gln Lys Asp His Glu Val Ala Glu Met Met Leu Glu Ala
545                 550                 555                 560
```

-continued

```
Gly Arg Gly Glu Leu Leu Arg Pro Val Tyr Ser Tyr Glu Cys Gly Arg
                565                 570                 575
Gly Leu Leu Ala Leu His Arg Trp Ile Gly Glu Ser Pro Glu Ala Lys
            580                 585                 590
Leu Ala Glu Asp Leu Lys Phe Glu Ser Gly Asp Val His Arg Met Val
            595                 600                 605
Glu Ser Ser Gly Trp Leu Leu Arg Cys Ile Trp Glu Ile Ser Lys His
610                 615                 620
Gln Glu Arg Pro Asp Leu Gly Glu Leu Asp Val Leu Arg Ser Arg
625                 630                 635                 640
Val Ala Tyr Gly Ile Lys Ala Glu Leu Val Pro Leu Val Ser Ile Lys
                645                 650                 655
Gly Ile Gly Arg Val Arg Ser Arg Arg Leu Phe Arg Gly Gly Ile Lys
            660                 665                 670
Gly Pro Gly Asp Leu Ala Ala Val Pro Val Glu Arg Leu Ser Arg Val
            675                 680                 685
Glu Gly Ile Gly Ala Thr Leu Ala Asn Asn Ile Lys Ser Gln Leu Arg
            690                 695                 700
Lys Gly Gly
705

<210> SEQ ID NO 10
<211> LENGTH: 720
<212> TYPE: PRT
<213> ORGANISM: Thermococcus gammatolerans

<400> SEQUENCE: 10

Met Lys Val Asp Glu Leu Pro Val Asp Glu Arg Leu Lys Ala Val Leu
1               5                   10                  15
Lys Glu Arg Gly Ile Glu Glu Leu Tyr Pro Pro Gln Ala Glu Ala Leu
                20                  25                  30
Lys Ser Gly Ala Leu Glu Gly Arg Asn Leu Val Leu Ala Ile Pro Thr
            35                  40                  45
Ala Ser Gly Lys Thr Leu Val Ser Glu Ile Val Met Val Asn Lys Leu
50                  55                  60
Ile Gln Glu Gly Gly Lys Ala Val Tyr Leu Val Pro Leu Lys Ala Leu
65                  70                  75                  80
Ala Glu Glu Lys Tyr Arg Glu Phe Lys Glu Trp Glu Lys Leu Gly Leu
                85                  90                  95
Lys Val Ala Ala Thr Thr Gly Asp Tyr Asp Ser Thr Asp Asp Trp Leu
            100                 105                 110
Gly Arg Tyr Asp Ile Ile Val Ala Thr Ala Glu Lys Phe Asp Ser Leu
            115                 120                 125
Leu Arg His Gly Ala Arg Trp Ile Asn Asp Val Lys Leu Val Val Ala
            130                 135                 140
Asp Glu Val His Leu Ile Gly Ser Tyr Asp Arg Gly Ala Thr Leu Glu
145                 150                 155                 160
Met Ile Leu Thr His Met Leu Gly Arg Ala Gln Ile Leu Ala Leu Ser
                165                 170                 175
Ala Thr Val Gly Asn Ala Glu Glu Leu Ala Glu Trp Leu Asp Ala Ser
            180                 185                 190
Leu Val Val Ser Asp Trp Arg Pro Val Gln Leu Arg Arg Gly Val Phe
            195                 200                 205
His Leu Gly Thr Leu Ile Trp Glu Asp Gly Lys Val Glu Ser Tyr Pro
            210                 215                 220
```

```
Glu Asn Trp Tyr Ser Leu Val Asp Ala Val Lys Arg Gly Lys Gly
225                 230                 235                 240

Ala Leu Val Phe Val Asn Thr Arg Arg Ser Ala Glu Lys Glu Ala Leu
                    245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                    325                 330                 335

Leu Pro Ser Phe Arg Val Ile Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                    405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                    485                 490                 495

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
        515                 520                 525

Leu Thr Ala Arg Arg Arg Glu Met Glu Asp Tyr Leu Asp Leu Ala Tyr
530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                    565                 570                 575

Asp Trp Ile Asn Glu Val Pro Glu Ala Arg Ile Tyr Glu Thr Tyr Ser
            580                 585                 590

Ile Asp Pro Gly Asp Leu Tyr Arg Leu Leu Glu Leu Ala Asp Trp Leu
        595                 600                 605

Met Tyr Ser Leu Ile Glu Leu Tyr Lys Leu Phe Glu Pro Lys Glu Glu
610                 615                 620

Ile Leu Asn Tyr Leu Arg Asp Leu His Leu Arg Leu Arg His Gly Val
625                 630                 635                 640
```

Arg Glu Glu Leu Leu Glu Leu Val Arg Leu Pro Asn Ile Gly Arg Lys
            645             650             655

Arg Ala Arg Ala Leu Tyr Asn Ala Gly Phe Arg Ser Val Glu Ala Ile
        660             665             670

Ala Asn Ala Lys Pro Ala Glu Leu Leu Ala Val Glu Gly Ile Gly Ala
        675             680             685

Lys Ile Leu Asp Gly Ile Tyr Arg His Leu Gly Ile Glu Lys Arg Val
        690             695             700

Thr Glu Glu Lys Pro Lys Arg Lys Gly Thr Leu Glu Asp Phe Leu Arg
705             710             715             720

<210> SEQ ID NO 11
<211> LENGTH: 799
<212> TYPE: PRT
<213> ORGANISM: Methanospirillum hungatei

<400> SEQUENCE: 11

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
            20                  25                  30

Glu Lys Gly Leu Leu Glu Gly Lys Asn Leu Leu Ile Ser Ile Pro Thr
        35                  40                  45

Ala Ser Gly Lys Thr Leu Leu Ala Glu Met Ala Met Trp Ser Arg Ile
50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
            85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
            115                 120                 125

Arg Thr Pro Trp Leu Ser Gln Ile Thr Cys Ile Val Leu Asp Glu Val
        130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
            165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
        195                 200                 205

Tyr Asn Gly Lys Ile Arg Phe Ser Asp Ser Glu Arg Pro Ile Gln Gly
210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
            245                 250                 255

Phe Ala Lys Lys Ala Ala Gly Ala Leu Lys Ala Gly Ser Pro Asp Ser
            260                 265                 270

Lys Ala Leu Ala Gln Glu Leu Arg Arg Leu Asp Arg Asp Glu Gly
        275                 280                 285

Asn Val Leu Ala Asp Cys Val Glu Arg Gly Ala Ala Phe His His Ala
        290                 295                 300

```
Gly Leu Ile Arg Gln Glu Arg Thr Ile Ile Glu Gly Phe Arg Asn
305                 310                 315                 320

Gly Tyr Ile Glu Val Ile Ala Ala Thr Pro Thr Leu Ala Ala Gly Leu
            325                 330                 335

Asn Leu Pro Ala Arg Arg Val Ile Ile Arg Asp Tyr Asn Arg Phe Ala
        340                 345                 350

Ser Gly Leu Gly Met Val Pro Ile Pro Val Gly Glu Tyr His Gln Met
        355                 360                 365

Ala Gly Arg Ala Gly Arg Pro His Leu Asp Pro Tyr Gly Glu Ala Val
370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
            405                 410                 415

Ser Leu Cys Ala His Ile Leu Ser Leu Ile Ala Thr Gly Phe Ala His
        420                 425                 430

Asp Gln Glu Ala Leu Ser Ser Phe Met Glu Arg Thr Phe Tyr Phe Phe
    435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
            485                 490                 495

Cys Thr Ala Arg Leu Ile Leu Asp Ser Leu Lys Ser Cys Lys Thr Pro
        500                 505                 510

Thr Leu Ile Gly Leu Leu His Val Ile Cys Val Ser Pro Asp Met Gln
    515                 520                 525

Arg Leu Tyr Leu Lys Ala Ala Asp Thr Gln Leu Leu Arg Thr Phe Leu
    530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
            565                 570                 575

Asp Trp Ala Asp Glu Phe Ser Glu Gly Met Ile Glu Glu Arg Tyr Gly
        580                 585                 590

Ile Gly Ala Gly Asp Leu Tyr Asn Ile Val Asp Ser Gly Lys Trp Leu
    595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
            645                 650                 655

Arg Thr Leu Tyr Asn Ala Gly Tyr Pro Asp Pro Glu Ala Val Ala Arg
        660                 665                 670

Ala Gly Leu Ser Thr Ile Ala Arg Ile Ile Gly Glu Gly Ile Ala Arg
    675                 680                 685

Gln Val Ile Asp Glu Ile Thr Gly Val Lys Arg Ser Gly Ile His Ser
    690                 695                 700

Ser Asp Asp Asp Tyr Gln Gln Lys Thr Pro Glu Leu Leu Thr Asp Ile
705                 710                 715                 720
```

```
Pro Gly Ile Gly Lys Lys Met Ala Glu Lys Leu Gln Asn Ala Gly Ile
                725                 730                 735
Ile Thr Val Ser Asp Leu Leu Thr Ala Asp Glu Val Leu Leu Ser Asp
            740                 745                 750
Val Leu Gly Ala Ala Arg Ala Arg Lys Val Leu Ala Phe Leu Ser Asn
        755                 760                 765
Ser Glu Lys Glu Asn Ser Ser Asp Lys Thr Glu Ile Pro Asp
770                 775                 780
Thr Gln Lys Ile Arg Gly Gln Ser Ser Trp Glu Asp Phe Gly Cys
785                 790                 795

<210> SEQ ID NO 12
<211> LENGTH: 1756
<212> TYPE: PRT
<213> ORGANISM: Escherichia coli

<400> SEQUENCE: 12

Met Met Ser Ile Ala Gln Val Arg Ser Ala Gly Ser Ala Gly Asn Tyr
1               5                   10                  15
Tyr Thr Asp Lys Asp Asn Tyr Tyr Val Leu Gly Ser Met Gly Glu Arg
            20                  25                  30
Trp Ala Gly Lys Gly Ala Glu Gln Leu Gly Leu Gln Gly Ser Val Asp
        35                  40                  45
Lys Asp Val Phe Thr Arg Leu Leu Glu Gly Arg Leu Pro Asp Gly Ala
    50                  55                  60
Asp Leu Ser Arg Met Gln Asp Gly Ser Asn Lys His Arg Pro Gly Tyr
65                  70                  75                  80
Asp Leu Thr Phe Ser Ala Pro Lys Ser Val Ser Met Met Ala Met Leu
                85                  90                  95
Gly Gly Asp Lys Arg Leu Ile Asp Ala His Asn Gln Ala Val Asp Phe
            100                 105                 110
Ala Val Arg Gln Val Glu Ala Leu Ala Ser Thr Arg Val Met Thr Asp
        115                 120                 125
Gly Gln Ser Glu Thr Val Leu Thr Gly Asn Leu Val Met Ala Leu Phe
    130                 135                 140
Asn His Asp Thr Ser Arg Asp Gln Glu Pro Gln Leu His Thr His Ala
145                 150                 155                 160
Val Val Ala Asn Val Thr Gln His Asn Gly Glu Trp Lys Thr Leu Ser
                165                 170                 175
Ser Asp Lys Val Gly Lys Thr Gly Phe Ile Glu Asn Val Tyr Ala Asn
            180                 185                 190
Gln Ile Ala Phe Gly Arg Leu Tyr Arg Glu Lys Leu Lys Glu Gln Val
        195                 200                 205
Glu Ala Leu Gly Tyr Glu Thr Glu Val Val Gly Lys His Gly Met Trp
    210                 215                 220
Glu Met Pro Gly Val Pro Val Glu Ala Phe Ser Gly Arg Ser Gln Ala
225                 230                 235                 240
Ile Arg Glu Ala Val Gly Glu Asp Ala Ser Leu Lys Ser Arg Asp Val
                245                 250                 255
Ala Ala Leu Asp Thr Arg Lys Ser Lys Gln His Val Asp Pro Glu Ile
            260                 265                 270
Arg Met Ala Glu Trp Met Gln Thr Leu Lys Glu Thr Gly Phe Asp Ile
        275                 280                 285
Arg Ala Tyr Arg Asp Ala Ala Asp Gln Arg Thr Glu Ile Arg Thr Gln
    290                 295                 300
```

```
Ala Pro Gly Pro Ala Ser Gln Asp Gly Pro Asp Val Gln Ala Val
305                 310                 315                 320

Thr Gln Ala Ile Ala Gly Leu Ser Glu Arg Lys Val Gln Phe Thr Tyr
            325                 330                 335

Thr Asp Val Leu Ala Arg Thr Val Gly Ile Leu Pro Pro Glu Asn Gly
        340                 345                 350

Val Ile Glu Arg Ala Arg Ala Gly Ile Asp Glu Ala Ile Ser Arg Glu
            355                 360                 365

Gln Leu Ile Pro Leu Asp Arg Glu Lys Gly Leu Phe Thr Ser Gly Ile
370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Ala Ala Gly Gln Arg Glu Arg
            435                 440                 445

Val Ala Glu Leu Val Met Met Ala Arg Glu Gln Gly Arg Glu Val Gln
450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
            485                 490                 495

Met Ala Phe Thr Pro Gly Ser Thr Val Ile Val Asp Gln Gly Glu Lys
                500                 505                 510

Leu Ser Leu Lys Glu Thr Leu Thr Leu Leu Asp Gly Ala Ala Arg His
            515                 520                 525

Asn Val Gln Val Leu Ile Thr Asp Ser Gly Gln Arg Thr Gly Thr Gly
            530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
            595                 600                 605

Ile Leu Thr Gln Ala Ile Arg Ser Glu Leu Lys Thr Gln Gly Val Leu
            610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
            660                 665                 670

Arg Val Thr Ala Gln Ser His Ser Leu Thr Leu Arg Asp Ala Gln Gly
            675                 680                 685

Glu Thr Gln Val Val Arg Ile Ser Ser Leu Asp Ser Ser Trp Ser Leu
            690                 695                 700

Phe Arg Pro Glu Lys Met Pro Val Ala Asp Gly Glu Arg Leu Arg Val
705                 710                 715                 720
```

```
Thr Gly Lys Ile Pro Gly Leu Arg Val Ser Gly Gly Asp Arg Leu Gln
            725                 730                 735

Val Ala Ser Val Ser Glu Asp Ala Met Thr Val Val Pro Gly Arg
        740                 745                 750

Ala Glu Pro Ala Ser Leu Pro Val Ser Asp Ser Pro Phe Thr Ala Leu
        755                 760                 765

Lys Leu Glu Asn Gly Trp Val Glu Thr Pro Gly His Ser Val Ser Asp
        770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
            805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
            835                 840                 845

Leu Glu Thr Ala Ile Ser Leu Gln Lys Ala Gly Leu His Thr Pro Ala
        850                 855                 860

Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
            885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
        930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
            965                 970                 975

Thr Arg Met Ile Leu Glu Thr Ser Asp Arg Phe Thr Val Val Gln Gly
            980                 985                 990

Tyr Ala Gly Val Gly Lys Thr Thr Gln Phe Arg Ala Val Met Ser Ala
        995                 1000                1005

Val Asn Met Leu Pro Ala Ser Glu Arg Pro Arg Val Val Gly Leu
        1010                1015                1020

Gly Pro Thr His Arg Ala Val Gly Glu Met Arg Ser Ala Gly Val
        1025                1030                1035

Asp Ala Gln Thr Leu Ala Ser Phe Leu His Asp Thr Gln Leu Gln
        1040                1045                1050

Gln Arg Ser Gly Glu Thr Pro Asp Phe Ser Asn Thr Leu Phe Leu
        1055                1060                1065

Leu Asp Glu Ser Ser Met Val Gly Asn Thr Glu Met Ala Arg Ala
        1070                1075                1080

Tyr Ala Leu Ile Ala Ala Gly Gly Gly Arg Ala Val Ala Ser Gly
        1085                1090                1095

Asp Thr Asp Gln Leu Gln Ala Ile Ala Pro Gly Gln Ser Phe Arg
        1100                1105                1110

Leu Gln Gln Thr Arg Ser Ala Ala Asp Val Val Ile Met Lys Glu
        1115                1120                1125

Ile Val Arg Gln Thr Pro Glu Leu Arg Glu Ala Val Tyr Ser Leu
```

```
                1130              1135              1140
Ile Asn Arg Asp Val Glu Arg Ala Leu Ser Gly Leu Glu Ser Val
    1145              1150              1155
Lys Pro Ser Gln Val Pro Arg Leu Glu Gly Ala Trp Ala Pro Glu
    1160              1165              1170
His Ser Val Thr Glu Phe Ser His Ser Gln Glu Ala Lys Leu Ala
    1175              1180              1185
Glu Ala Gln Gln Lys Ala Met Leu Lys Gly Glu Ala Phe Pro Asp
    1190              1195              1200
Ile Pro Met Thr Leu Tyr Glu Ala Ile Val Arg Asp Tyr Thr Gly
    1205              1210              1215
Arg Thr Pro Glu Ala Arg Glu Gln Thr Leu Ile Val Thr His Leu
    1220              1225              1230
Asn Glu Asp Arg Arg Val Leu Asn Ser Met Ile His Asp Ala Arg
    1235              1240              1245
Glu Lys Ala Gly Glu Leu Gly Lys Glu Gln Val Met Val Pro Val
    1250              1255              1260
Leu Asn Thr Ala Asn Ile Arg Asp Gly Glu Leu Arg Arg Leu Ser
    1265              1270              1275
Thr Trp Glu Lys Asn Pro Asp Ala Leu Ala Leu Val Asp Asn Val
    1280              1285              1290
Tyr His Arg Ile Ala Gly Ile Ser Lys Asp Asp Gly Leu Ile Thr
    1295              1300              1305
Leu Gln Asp Ala Glu Gly Asn Thr Arg Leu Ile Ser Pro Arg Glu
    1310              1315              1320
Ala Val Ala Glu Gly Val Thr Leu Tyr Thr Pro Asp Lys Ile Arg
    1325              1330              1335
Val Gly Thr Gly Asp Arg Met Arg Phe Thr Lys Ser Asp Arg Glu
    1340              1345              1350
Arg Gly Tyr Val Ala Asn Ser Val Trp Thr Val Thr Ala Val Ser
    1355              1360              1365
Gly Asp Ser Val Thr Leu Ser Asp Gly Gln Gln Thr Arg Val Ile
    1370              1375              1380
Arg Pro Gly Gln Glu Arg Ala Glu Gln His Ile Asp Leu Ala Tyr
    1385              1390              1395
Ala Ile Thr Ala His Gly Ala Gln Gly Ala Ser Glu Thr Phe Ala
    1400              1405              1410
Ile Ala Leu Glu Gly Thr Glu Gly Asn Arg Lys Leu Met Ala Gly
    1415              1420              1425
Phe Glu Ser Ala Tyr Val Ala Leu Ser Arg Met Lys Gln His Val
    1430              1435              1440
Gln Val Tyr Thr Asp Asn Arg Gln Gly Trp Thr Asp Ala Ile Asn
    1445              1450              1455
Asn Ala Val Gln Lys Gly Thr Ala His Asp Val Leu Glu Pro Lys
    1460              1465              1470
Pro Asp Arg Glu Val Met Asn Ala Gln Arg Leu Phe Ser Thr Ala
    1475              1480              1485
Arg Glu Leu Arg Asp Val Ala Ala Gly Arg Ala Val Leu Arg Gln
    1490              1495              1500
Ala Gly Leu Ala Gly Gly Asp Ser Pro Ala Arg Phe Ile Ala Pro
    1505              1510              1515
Gly Arg Lys Tyr Pro Gln Pro Tyr Val Ala Leu Pro Ala Phe Asp
    1520              1525              1530
```

```
Arg Asn Gly Lys Ser Ala Gly Ile Trp Leu Asn Pro Leu Thr Thr
    1535                1540                1545

Asp Asp Gly Asn Gly Leu Arg Gly Phe Ser Gly Glu Gly Arg Val
    1550                1555                1560

Lys Gly Ser Gly Asp Ala Gln Phe Val Ala Leu Gln Gly Ser Arg
    1565                1570                1575

Asn Gly Glu Ser Leu Leu Ala Asp Asn Met Gln Asp Gly Val Arg
    1580                1585                1590

Ile Ala Arg Asp Asn Pro Asp Ser Gly Val Val Val Arg Ile Ala
    1595                1600                1605

Gly Glu Gly Arg Pro Trp Asn Pro Gly Ala Ile Thr Gly Gly Arg
    1610                1615                1620

Val Trp Gly Asp Ile Pro Asp Asn Ser Val Gln Pro Gly Ala Gly
    1625                1630                1635

Asn Gly Glu Pro Val Thr Ala Glu Val Leu Ala Gln Arg Gln Ala
    1640                1645                1650

Glu Glu Ala Ile Arg Arg Glu Thr Glu Arg Arg Ala Asp Glu Ile
    1655                1660                1665

Val Arg Lys Met Ala Glu Asn Lys Pro Asp Leu Pro Asp Gly Lys
    1670                1675                1680

Thr Glu Leu Ala Val Arg Asp Ile Ala Gly Gln Glu Arg Asp Arg
    1685                1690                1695

Ser Ala Ile Ser Glu Arg Glu Thr Ala Leu Pro Glu Ser Val Leu
    1700                1705                1710

Arg Glu Ser Gln Arg Glu Arg Glu Ala Val Arg Glu Val Ala Arg
    1715                1720                1725

Glu Asn Leu Leu Gln Glu Arg Leu Gln Gln Met Glu Arg Asp Met
    1730                1735                1740

Val Arg Asp Leu Gln Lys Glu Lys Thr Leu Gly Gly Asp
    1745                1750                1755

<210> SEQ ID NO 13
<211> LENGTH: 726
<212> TYPE: PRT
<213> ORGANISM: Methanococcoides burtonii

<400> SEQUENCE: 13

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
            20                  25                  30

Gln Gln Gln Leu Val Leu Phe Glu Gly Ala Cys Gly Thr Gly Lys Thr
        35                  40                  45

Leu Ser Ala Leu Val Pro Ala Leu His Val Gly Lys Met Leu Gly Lys
    50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
                100                 105                 110

Cys Ser Val Lys Arg Glu Asn Thr Phe Glu Leu Met Glu Thr Glu Arg
            115                 120                 125

Glu Ile Tyr Leu Lys Arg Gln Glu Leu Asn Ser Ala Arg Asp Ser Tyr
```

```
                    130                 135                 140
Lys Lys Ser His Asp Pro Ala Phe Val Thr Leu Arg Asp Glu Leu Ser
145                 150                 155                 160

Lys Glu Ile Asp Ala Val Glu Lys Ala Arg Gly Leu Arg Asp Arg
                    165                 170                 175

Ala Cys Asn Asp Leu Tyr Glu Val Leu Arg Ser Asp Ser Glu Lys Phe
                180                 185                 190

Arg Glu Trp Leu Tyr Lys Glu Val Arg Ser Pro Glu Glu Ile Asn Asp
                195                 200                 205

His Ala Ile Lys Asp Gly Met Cys Gly Tyr Glu Leu Val Lys Arg Glu
                210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                    245                 250                 255

Glu Thr Ile Val Ile Phe Asp Glu Ala His Asn Leu Glu Ser Ala Ala
                260                 265                 270

Arg Ser His Ser Ser Leu Ser Leu Thr Glu His Ser Ile Glu Lys Ala
                275                 280                 285

Ile Thr Glu Leu Glu Ala Asn Leu Asp Leu Leu Ala Asp Asp Asn Ile
                290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Val Arg Lys Asn Trp Tyr
                    325                 330                 335

Asp Ile Arg Ile Ser Asp Pro Tyr Glu Arg Asn Asp Ile Val Arg Gly
                340                 345                 350

Lys Phe Leu Arg Gln Ala Lys Gly Asp Phe Gly Glu Lys Asp Asp Ile
                355                 360                 365

Gln Ile Leu Leu Ser Glu Ala Ser Glu Leu Gly Ala Lys Leu Asp Glu
                370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                    405                 410                 415

Ser His Asn Leu Asn Tyr Tyr Pro Ile Leu Asn Val Arg Arg Asp Met
                    420                 425                 430

Asn Asp Glu Ile Tyr Gly Arg Val Glu Leu Phe Thr Cys Ile Pro Lys
                435                 440                 445

Asn Val Thr Glu Pro Leu Phe Asn Ser Leu Phe Ser Val Ile Leu Met
                450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                    485                 490                 495

Lys Arg Leu Ser Ile Ala Val Ser Ile Pro Pro Leu Phe Ala Lys Asn
                500                 505                 510

Arg Asp Asp Arg His Val Thr Glu Leu Leu Gln Val Leu Leu Asp
                515                 520                 525

Ser Ile Glu Asn Ser Lys Gly Asn Val Ile Leu Phe Phe Gln Ser Ala
                530                 535                 540

Phe Glu Ala Lys Arg Tyr Tyr Ser Lys Ile Glu Pro Leu Val Asn Val
545                 550                 555                 560
```

-continued

Pro Val Phe Leu Asp Glu Val Gly Ile Ser Ser Gln Asp Val Arg Glu
              565                 570                 575

Glu Phe Phe Ser Ile Gly Glu Glu Asn Gly Lys Ala Val Leu Leu Ser
              580                 585                 590

Tyr Leu Trp Gly Thr Leu Ser Glu Gly Ile Asp Tyr Arg Asp Gly Arg
              595                 600                 605

Gly Arg Thr Val Ile Ile Gly Val Gly Tyr Pro Ala Leu Asn Asp
610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
              645                 650                 655

Gln Ala Met Gly Arg Val Val Arg Ser Pro Thr Asp Tyr Gly Ala Arg
              660                 665                 670

Ile Leu Leu Asp Gly Arg Phe Leu Thr Asp Ser Lys Lys Arg Phe Gly
              675                 680                 685

Lys Phe Ser Val Phe Glu Val Phe Pro Pro Ala Glu Arg Ser Glu Phe
              690                 695                 700

Val Asp Val Asp Pro Glu Lys Val Lys Tyr Ser Leu Met Asn Phe Phe
705                 710                 715                 720

Met Asp Asn Asp Glu Gln
              725

<210> SEQ ID NO 14
<211> LENGTH: 439
<212> TYPE: PRT
<213> ORGANISM: Enterobacteria phage T4

<400> SEQUENCE: 14

Met Thr Phe Asp Asp Leu Thr Glu Gly Gln Lys Asn Ala Phe Asn Ile
1               5                   10                  15

Val Met Lys Ala Ile Lys Glu Lys Lys His His Val Thr Ile Asn Gly
              20                  25                  30

Pro Ala Gly Thr Gly Lys Thr Thr Leu Thr Lys Phe Ile Ile Glu Ala
              35                  40                  45

Leu Ile Ser Thr Gly Glu Thr Gly Ile Ile Leu Ala Ala Pro Thr His
      50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
              85                  90                  95

Leu Phe Glu Gln Lys Glu Val Pro Asp Leu Ala Lys Cys Arg Val Leu
              100                 105                 110

Ile Cys Asp Glu Val Ser Met Tyr Asp Arg Lys Leu Phe Lys Ile Leu
              115                 120                 125

Leu Ser Thr Ile Pro Pro Trp Cys Thr Ile Ile Gly Ile Gly Asp Asn
      130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
              165                 170                 175

Lys Arg Ser Asn Ala Pro Ile Ile Asp Val Ala Thr Asp Val Arg Asn
              180                 185                 190

Gly Lys Trp Ile Tyr Asp Lys Val Val Asp Gly His Gly Val Arg Gly

```
        195                 200                 205
Phe Thr Gly Asp Thr Ala Leu Arg Asp Phe Met Val Asn Tyr Phe Ser
210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
                275                 280                 285

Ile Ile Phe Asn Asn Gly Gln Leu Val Arg Ile Ile Glu Ala Glu Tyr
        290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
            435

<210> SEQ ID NO 15
<211> LENGTH: 970
<212> TYPE: PRT
<213> ORGANISM: Clostridium botulinum

<400> SEQUENCE: 15

Met Leu Ser Val Ala Asn Val Arg Ser Pro Ser Ala Ala Ser Tyr
1               5                   10                  15

Phe Ala Ser Asp Asn Tyr Tyr Ala Ser Ala Asp Ala Asp Arg Ser Gly
                20                  25                  30

Gln Trp Ile Gly Asp Gly Ala Lys Arg Leu Gly Leu Glu Gly Lys Val
            35                  40                  45

Glu Ala Arg Ala Phe Asp Ala Leu Leu Arg Gly Glu Leu Pro Asp Gly
        50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
                100                 105                 110

His Trp Ala Glu Lys Asn Ala Ala Glu Thr Arg Val Val Glu Lys Gly
            115                 120                 125
```

```
Met Val Val Thr Gln Ala Thr Gly Asn Leu Ala Ile Gly Leu Phe Gln
            130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
                180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
            275                 280                 285

Ala Arg Thr Lys Ala Leu Gly Gln Gly Met Glu Ala Thr Arg Ile Gly
290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Ser Val Leu Lys
                325                 330                 335

Gln Asp Arg Gln Thr Ile Ala Ala Ala Gln Ala Val Ala Ser Ala Val
            340                 345                 350

Arg His Leu Ser Gln Arg Glu Ala Ala Phe Glu Arg Thr Ala Leu Tyr
            355                 360                 365

Lys Ala Ala Leu Asp Phe Gly Leu Pro Thr Thr Ile Ala Asp Val Glu
            370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Thr Glu
                405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ala Ser Val Gln Ala Ala Ala Leu
            435                 440                 445

Thr Gly Gln Gly Phe Arg Leu Asn Glu Gly Gln Leu Ala Ala Ala Arg
450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
            485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
            515                 520                 525

Phe Leu Gly Gly Trp Asn Lys Leu Leu Asp Asp Pro Gly Asn Val Ala
530                 535                 540

Leu Arg Ala Glu Ala Gln Ala Ser Leu Lys Asp His Val Leu Val Leu
```

-continued

```
            545                 550                 555                 560
Asp Glu Ala Ser Met Val Ser Asn Glu Asp Lys Glu Lys Leu Val Arg
                    565                 570                 575
Leu Ala Asn Leu Ala Gly Val His Arg Leu Val Leu Ile Gly Asp Arg
                580                 585                 590
Lys Gln Leu Gly Ala Val Asp Ala Gly Lys Pro Phe Ala Leu Leu Gln
            595                 600                 605
Arg Ala Gly Ile Ala Arg Ala Glu Met Ala Thr Asn Leu Arg Ala Arg
        610                 615                 620
Asp Pro Val Val Arg Glu Ala Gln Ala Ala Gln Ala Gly Asp Val
625                 630                 635                 640
Arg Lys Ala Leu Arg His Leu Lys Ser His Thr Val Glu Ala Arg Gly
                645                 650                 655
Asp Gly Ala Gln Val Ala Ala Glu Thr Trp Leu Ala Leu Asp Lys Glu
            660                 665                 670
Thr Arg Ala Arg Thr Ser Ile Tyr Ala Ser Gly Arg Ala Ile Arg Ser
        675                 680                 685
Ala Val Asn Ala Ala Val Gln Gln Gly Leu Leu Ala Ser Arg Glu Ile
        690                 695                 700
Gly Pro Ala Lys Met Lys Leu Glu Val Leu Asp Arg Val Asn Thr Thr
705                 710                 715                 720
Arg Glu Glu Leu Arg His Leu Pro Ala Tyr Arg Ala Gly Arg Val Leu
                725                 730                 735
Glu Val Ser Arg Lys Gln Gln Ala Leu Gly Leu Phe Ile Gly Glu Tyr
            740                 745                 750
Arg Val Ile Gly Gln Asp Arg Lys Gly Lys Leu Val Glu Val Glu Asp
        755                 760                 765
Lys Arg Gly Lys Arg Phe Arg Phe Asp Pro Ala Arg Ile Arg Ala Gly
        770                 775                 780
Lys Gly Asp Asp Asn Leu Thr Leu Leu Glu Pro Arg Lys Leu Glu Ile
785                 790                 795                 800
His Glu Gly Asp Arg Ile Arg Trp Thr Arg Asn Asp His Arg Arg Gly
                805                 810                 815
Leu Phe Asn Ala Asp Gln Ala Arg Val Val Glu Ile Ala Asn Gly Lys
            820                 825                 830
Val Thr Phe Glu Thr Ser Lys Gly Asp Leu Val Glu Leu Lys Lys Asp
        835                 840                 845
Asp Pro Met Leu Lys Arg Ile Asp Leu Ala Tyr Ala Leu Asn Val His
        850                 855                 860
Met Ala Gln Gly Leu Thr Ser Asp Arg Gly Ile Ala Val Met Asp Ser
865                 870                 875                 880
Arg Glu Arg Asn Leu Ser Asn Gln Lys Thr Phe Leu Val Thr Val Thr
                885                 890                 895
Arg Leu Arg Asp His Leu Thr Leu Val Val Asp Ser Ala Asp Lys Leu
                900                 905                 910
Gly Ala Ala Val Ala Arg Asn Lys Gly Glu Lys Ala Ser Ala Ile Glu
            915                 920                 925
Val Thr Gly Ser Val Lys Pro Thr Ala Thr Lys Gly Ser Gly Val Asp
        930                 935                 940
Gln Pro Lys Ser Val Glu Ala Asn Lys Ala Glu Lys Glu Leu Thr Arg
945                 950                 955                 960
Ser Lys Ser Lys Thr Leu Asp Phe Gly Ile
                965                 970
```

<210> SEQ ID NO 16
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 16
tttttttttt tttttttttt tttttttttt tttttttttt                           40

<210> SEQ ID NO 17
<211> LENGTH: 40
<212> TYPE: RNA
<213> ORGANISM: Artificial Sequence
<220> FEATURE:
<223> OTHER INFORMATION: Synthetic polynucleotide

<400> SEQUENCE: 17
gguuguuucu guuggugcug auauugcauu uaagagcauu                           40

<210> SEQ ID NO 18
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 18
gcaatatcag caccaacaga aacaacct                                        28

<210> SEQ ID NO 19
<211> LENGTH: 55
<212> TYPE: RNA
<213> ORGANISM: Artificial Sequence
<220> FEATURE:
<223> OTHER INFORMATION: Synthetic polynucleotide

<400> SEQUENCE: 19
gggaaauaag agagaccaca ccacccacac cacccacacc acccacacca cacca          55

<210> SEQ ID NO 20
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 20
tctctcttat ttcccaggtt aaacacccaa gcagacgcc                            39

<210> SEQ ID NO 21
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 21
ggcgtctgct tgggtgttta acct                                            24

<210> SEQ ID NO 22
<211> LENGTH: 40
<212> TYPE: DNA
<213> ORGANISM: Artificial Sequence
<220> FEATURE:

```
<223> OTHER INFORMATION: Synthetic polynucleotide

<400> SEQUENCE: 22 cccccccca cccccccca cccccccca cccccccca                              40

<210> SEQ ID NO 23
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 23
ggttgtttct gttggtgctg atattgcggc gtctgcttgg gtgtttaacc t             51

<210> SEQ ID NO 24
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 24
tctctcttat cccaaacacc caagcagacg cc                                  32

<210> SEQ ID NO 25
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 25
ggcgtctgct tgggtgttta acct                                           24

<210> SEQ ID NO 26
<211> LENGTH: 1653
<212> TYPE: RNA
<213> ORGANISM: Artificial Sequence
<220> FEATURE:
<223> OTHER INFORMATION: Synthetic polynucleotide

<400> SEQUENCE: 26
auggaagacg ccaaaaacau aaagaaaggc ccggcgccau ucuauccgcu ggaagaugga     60
accgcuggag agcaacugca uaaggcuaug aagagauacg cccugguucc uggaacaauu    120
gcuuuuacag augcacauau cgagguggac aucacuuacg cugaguacuu cgaaaugucc    180
guucgguugg cagaagcuau gaaacgauau gggcugaaua caaaucacag aaucgucgua    240
ugcagugaaa acucucuuca auucuuuaug ccgguguugg gcgcguuauu aucggaguu     300 gcaguugcgc ccgcgaacga cauuuauaau gaacgugaau ugcucaacag uaugggcauu    360
ucgcagccua ccgugguguu cguuccaaa aaggggguugc aaaaaauuuu gaacgugcaa    420
aaaaagcucc caaucaucca aaaaauuauu aucauggauu cuaaaacgga uuaccaggga    480
uuucagucga guacacguu cgucacaucu caucuaccuc ccgguuuaa ugaauacgau     540 uuugugccag aguccuucga uagggacaag acaauugcac ugaucaugaa cuccucugga    600 ucuacuggu ugccuaaagg ugucgcucug ccucauagaa cugccugcgu gagauucucg    660
caugccagag auccuauuu uggcaaucaa aucauuccgg auacugcgau uuuaagugu     720 guuccauucc aucacgguuu uggaauguuu acuacacucg gauauuugau augugauuu    780 cgagucgucu uaauguauag auuugaagaa gagcuguuc ugaggagccu ucaggauuuac    840
```

```
aagauucaaa gugcgcugcu ggugccaacc cuauucuccu ucuucgccaa aagcacucug    900
auugacaaau acgauuuauc uaauuuacac gaaauugcuu cugguggcgc uccccucucu    960
aaggaagucg gggaagcggu ugccaagagg uuccaucugc cagguaucag gcaaggauau   1020
gggcucacug agacuacauc agcuauucug auuacacccg aggggauga uaaaccgggc    1080 gcggucggua aaguuguucc auuuuugaa gcgaagguug uggaucugga uaccgggaaa    1140
acgcugggcg uuaaucaaag aggcgaacug ugugugagag guccuaugau uaugccggu    1200 uauguaaaca auccggaagc gaccaacgcc uugauugaca aggauggaug gcuacauucu    1260
ggagacauag cuuacuggga cgaagacgaa cacuucuuca ucguugaccg ccugaagucu    1320
cugauuaagu acaaaggcua ucagguggcu cccgcugaau uggaauccau cuugcuccaa    1380
caccccaaca ucuucgacgc aggugucgca ggucuucccg acgaugacgc cggugaacuu    1440
cccgccgccg uuguuguuuu ggagcacgga aagacgauga cggaaaaaga gaucguggau    1500
uacgucgcca gucaaguaac aaccgcgaaa aaguugcgcg gaggaguugu guuuguggac    1560
gaaguaccga aaggucuuac cggaaaacuc gacgcaagaa aaaucagaga gauccucaua    1620
aaggccaaga agggcggaaa gaucgccgug uaa                                1653

<210> SEQ ID NO 27
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 27
ccccccccca ccccccccca ccccccccca agaaacataa acagaacgtt tttttttt      58

<210> SEQ ID NO 28
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 28
ccccccccca ccccccccca ccccccccca agaaacataa acagaacgtt t              51

<210> SEQ ID NO 29
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 29
cgttctgttt atgtttcttg gacactgatt gacacggttt agtagaac                  48

<210> SEQ ID NO 30
<211> LENGTH: 288
<212> TYPE: RNA
<213> ORGANISM: Artificial Sequence
<220> FEATURE:
<223> OTHER INFORMATION: Synthetic polynucleotide

<400> SEQUENCE: 30 gggaauaag agagaaaaga agaguaagaa gaaauauaag agccaccaug guuuauauug      60
cggccgcuua auuaagcugc cuucugcggg gcuugccuuc uggccaugcc cuucuucucu    120
```
cccuugcacc uguaccucuu ggucuuugaa uaaagccuga guaggaagaa aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaa                 288

<210> SEQ ID NO 31
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 31
ccccccccca                                                            10

<210> SEQ ID NO 32
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 32
ggttgtttct gttggtgctg atattgc                                         27

<210> SEQ ID NO 33
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 33
aaaaaaaaaa aa                                                         12

<210> SEQ ID NO 34
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: n
<222> LOCATION: (4)..(4)
<223> OTHER INFORMATION: Inosine
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: n
<222> LOCATION: (7)..(8)
<223> OTHER INFORMATION: Inosine
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: n
<222> LOCATION: (12)..(12)
<223> OTHER INFORMATION: Inosine
<220> FEATURE:
<221> NAME/KEY: misc_feature
<222> LOCATION: (12)..(12)
<223> OTHER INFORMATION: n is a, c, g, or t

<400> SEQUENCE: 34
tttnttnntt tn                                                         12

```
<210> SEQ ID NO 35
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 35
gcaatatcag caccaacaga aarcrararc rc                                  32

<210> SEQ ID NO 36
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 36
ttctgaatta ggaaccattt tttttttttt atgatgcaag atacgcac                 48

<210> SEQ ID NO 37
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 37
gaggcgagcg gtcaatttgt gcgtatcttg catcat                              36

<210> SEQ ID NO 38
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 38
atggttccta attcagaa                                                  18

<210> SEQ ID NO 39
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 39
ttgaccgctc gcctc                                                     15

<210> SEQ ID NO 40
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 40
ggttgtttct gttggtgctg atattgcttt ttttttt                             37

<210> SEQ ID NO 41
<211> LENGTH: 897
<212> TYPE: DNA
<213> ORGANISM: Eisenia fetida

<400> SEQUENCE: 41
```

-continued

```
atgagtgcga aggctgctga aggttatgaa caaatcgaag ttgatgtggt tgctgtgtgg      60
aaggaaggtt atgtgtatga aaatcgtggt agtacctccg tggatcaaaa aattaccatc     120
acgaaaggca tgaagaacgt taatagcgaa acccgtacgg tcaccgcgac gcattctatt     180
ggcagtacca tctccacggg tgacgccttt gaaatcggct ccgtggaagt ttcatattcg     240
catagccacg aagaatcaca agtttcgatg accgaaacgg aagtctacga atcaaaagtg     300
attgaacaca ccattacgat cccgccgacc tcgaagttca cgcgctggca gctgaacgca     360
gatgtcggcg gtgctgacat tgaatatatg tacctgatcg atgaagttac cccgattggc     420
ggtacgcaga gtattccgca agtgatcacc tcccgtgcaa aaattatcgt tggtcgccag     480
attatcctgg gcaagaccga aattcgtatc aaacatgctg aacgcaagga atatatgacc     540
gtggttagcc gtaaatcttg gccggcggcc acgctgggtc acagtaaact gtttaagttc     600
gtgctgtacg aagattgggg cggttttcgc atcaaaaccc tgaatacgat gtattctggt     660
tatgaatacg cgtatagctc tgaccagggc ggtatctact tcgatcaagg caccgacaac     720
ccgaaacagc gttgggccat taataagagc ctgccgctgc gccatggtga tgtcgtgacc     780
tttatgaaca aatacttcac gcgttctggt ctgtgctatg atgacggccc ggcgaccaat     840
gtgtattgtc tggataaacg cgaagacaag tggattctgg aagttgtcgg ctaatga       897
```

<210> SEQ ID NO 42
<211> LENGTH: 297
<212> TYPE: PRT
<213> ORGANISM: Eisenia fetida

<400> SEQUENCE: 42

```
Met Ser Ala Lys Ala Ala Glu Gly Tyr Glu Gln Ile Glu Val Asp Val
1               5                   10                  15

Val Ala Val Trp Lys Glu Gly Tyr Val Tyr Glu Asn Arg Gly Ser Thr
            20                  25                  30

Ser Val Asp Gln Lys Ile Thr Ile Thr Lys Gly Met Lys Asn Val Asn
        35                  40                  45

Ser Glu Thr Arg Thr Val Thr Ala Thr His Ser Ile Gly Ser Thr Ile
    50                  55                  60

Ser Thr Gly Asp Ala Phe Glu Ile Gly Ser Val Glu Val Ser Tyr Ser
65                  70                  75                  80

His Ser His Glu Glu Ser Gln Val Ser Met Thr Glu Thr Glu Val Tyr
                85                  90                  95

Glu Ser Lys Val Ile Glu His Thr Ile Thr Ile Pro Pro Thr Ser Lys
            100                 105                 110

Phe Thr Arg Trp Gln Leu Asn Ala Asp Val Gly Gly Ala Asp Ile Glu
        115                 120                 125

Tyr Met Tyr Leu Ile Asp Glu Val Thr Pro Ile Gly Gly Thr Gln Ser
    130                 135                 140

Ile Pro Gln Val Ile Thr Ser Arg Ala Lys Ile Ile Val Gly Arg Gln
145                 150                 155                 160

Ile Ile Leu Gly Lys Thr Glu Ile Arg Ile Lys His Ala Glu Arg Lys
                165                 170                 175

Glu Tyr Met Thr Val Val Ser Arg Lys Ser Trp Pro Ala Ala Thr Leu
            180                 185                 190

Gly His Ser Lys Leu Phe Lys Phe Val Leu Tyr Glu Asp Trp Gly Gly
        195                 200                 205

Phe Arg Ile Lys Thr Leu Asn Thr Met Tyr Ser Gly Tyr Glu Tyr Ala
    210                 215                 220
```

Tyr Ser Ser Asp Gln Gly Gly Ile Tyr Phe Asp Gln Gly Thr Asp Asn
225                 230                 235                 240

Pro Lys Gln Arg Trp Ala Ile Asn Lys Ser Leu Pro Leu Arg His Gly
            245                 250                 255

Asp Val Val Thr Phe Met Asn Lys Tyr Phe Thr Arg Ser Gly Leu Cys
        260                 265                 270

Tyr Asp Asp Gly Pro Ala Thr Asn Val Tyr Cys Leu Asp Lys Arg Glu
    275                 280                 285

Asp Lys Trp Ile Leu Glu Val Val Gly
290                 295

<210> SEQ ID NO 43
<211> LENGTH: 786
<212> TYPE: DNA
<213> ORGANISM: Escherichia coli

<400> SEQUENCE: 43
tgtctgaccg caccgccgaa agaagcggca cgtccgaccc tgatgccgcg tgcacagtct      60
tataaagatc tgacccatct gccggctccg acgggcaaaa ttttgttag cgtctataac     120 atccaggacg aaaccggtca atttaaaccg tacccggcga gtaatttctc cacggccgtt     180
ccgcagagtg caaccgctat gctggtcacg gcactgaaag attccgttg gttcattccg     240 ctggaacgcc agggcctgca aaacctgctg aatgaacgta aaattatccg cgcagctcag     300
gaaaacggta ccgtggccat taacaatcgt attccgctgc aaagcctgac cgccgcaaac     360
atcatggttg aaggctctat catcggttac gaatcaaacg tcaaatcggg cggtgtgggc     420
gcacgttatt ttggcattgg tgctgatacc cagtaccaac tggaccagat cgcagttaac     480
ctgcgcgtgg ttaatgtcag caccggcgaa attctgagct ctgtgaatac cagcaaaacg     540
atcctgtctt acgaagtgca ggctggtgtt tttcgtttca ttgattatca acgcctgctg     600
gaaggcgaag tcggttacac ctcaaacgaa ccggtgatgc tgtgtctgat gtcggcgatt     660
gaaacgggtg ttatttttcct gatcaatgat ggcatcgacc gtggtctgtg ggatctgcag     720
aacaaagccg aacgtcaaaa tgacattctg gtgaaatacc gccacatgag tgttccgccg     780
gaatcc                                                                786

<210> SEQ ID NO 44
<211> LENGTH: 262
<212> TYPE: PRT
<213> ORGANISM: Escherichia coli

<400> SEQUENCE: 44

Cys Leu Thr Ala Pro Pro Lys Glu Ala Ala Arg Pro Thr Leu Met Pro
1               5                   10                  15

Arg Ala Gln Ser Tyr Lys Asp Leu Thr His Leu Pro Ala Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Ile Asn Asn Arg Ile Pro

```
            100                 105                 110
Leu Gln Ser Leu Thr Ala Ala Asn Ile Met Val Glu Gly Ser Ile Ile
        115                 120                 125

Gly Tyr Glu Ser Asn Val Lys Ser Gly Val Gly Ala Arg Tyr Phe
    130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Val Gly Tyr Thr Ser
        195                 200                 205

Asn Glu Pro Val Met Leu Cys Leu Met Ser Ala Ile Glu Thr Gly Val
    210                 215                 220

Ile Phe Leu Ile Asn Asp Gly Ile Asp Arg Gly Leu Trp Asp Leu Gln
225                 230                 235                 240

Asn Lys Ala Glu Arg Gln Asn Asp Ile Leu Val Lys Tyr Arg His Met
                245                 250                 255

Ser Val Pro Pro Glu Ser
            260

<210> SEQ ID NO 45
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 45

Ser Ala Trp Ser His Pro Gln Phe Glu Lys
1               5                   10

<210> SEQ ID NO 46
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 46 cccccccca cccccccca cccccccca cccccccca                    40

<210> SEQ ID NO 47
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 47
actcgcagat cattacgatc                                      20

<210> SEQ ID NO 48
<211> LENGTH: 39
<212> TYPE: RNA
<213> ORGANISM: Artificial Sequence
<220> FEATURE:
<223> OTHER INFORMATION: Synthetic polynucleotide

<400> SEQUENCE: 48
```

```
rarcrurcrg rcrargraru rcrarururca rcrgarurc                                39

<210> SEQ ID NO 49
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 49
cgattgacta agctatacgc                                                      20

<210> SEQ ID NO 50
<211> LENGTH: 40
<212> TYPE: RNA
<213> ORGANISM: Artificial Sequence
<220> FEATURE:
<223> OTHER INFORMATION: Synthetic polynucleotide

<400> SEQUENCE: 50
rcrgraruru rgrarcrura rargrcrura rurarcrgrc                                40

<210> SEQ ID NO 51
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 51
tttttttttt                                                                 10

<210> SEQ ID NO 52
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 52
tttttttttt tttttttttt                                                      20

<210> SEQ ID NO 53
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 53 cccccccca cccccccca                                                        20

<210> SEQ ID NO 54
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 54 rararara rararara                                                          20

<210> SEQ ID NO 55
<211> LENGTH: 20
<212> TYPE: RNA
<213> ORGANISM: Artificial Sequence
```

<220> FEATURE:
<223> OTHER INFORMATION: Synthetic polynucleotide

<400> SEQUENCE: 55
rurcrcraru rarcrgrara                                              20

<210> SEQ ID NO 56
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 56
aactactagg atcatcgatg tatctgctca                                   30

<210> SEQ ID NO 57
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 57
agcttaacat acgatactct tagctaacca                                   30

<210> SEQ ID NO 58
<211> LENGTH: 60
<212> TYPE: RNA
<213> ORGANISM: Artificial Sequence
<220> FEATURE:
<223> OTHER INFORMATION: Synthetic polynucleotide

<400> SEQUENCE: 58
rararcrura rcrurargrg rarurcraru rcrgrarurg rurarurcru rgrcrurcra    60

<210> SEQ ID NO 59
<211> LENGTH: 60
<212> TYPE: RNA
<213> ORGANISM: Artificial Sequence
<220> FEATURE:
<223> OTHER INFORMATION: Synthetic polynucleotide

<400> SEQUENCE: 59
rargrcruru rararcraru rarcrgraru rarcrurcru rurargrcru rararcrcra    60

<210> SEQ ID NO 60
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 60
actctgaacc                                                          10

<210> SEQ ID NO 61
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 61
actctrgrar arcrc                                                    15

<210> SEQ ID NO 62
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 62
gcacaatgat                                                              10

<210> SEQ ID NO 63
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 63
gcacarartr grart                                                        15

<210> SEQ ID NO 64
<211> LENGTH: 20
<212> TYPE: RNA
<213> ORGANISM: Artificial Sequence
<220> FEATURE:
<223> OTHER INFORMATION: Synthetic polynucleotide

<400> SEQUENCE: 64
rarararcru rarcrgrcru                                                   20

<210> SEQ ID NO 65
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 65
ttgttctact aaaccgtgtc aatcagtgtc tt                                     32

<210> SEQ ID NO 66
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 66
gcaatatcag caccaacaga aacaacctt                                         29

<210> SEQ ID NO 67
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 67
catatccgtg tcgcccttat tccgatagtg actaca                                 36

<210> SEQ ID NO 68
<211> LENGTH: 36
<212> TYPE: DNA
<213> ORGANISM: Artificial Sequence
<220> FEATURE:
<223> OTHER INFORMATION: Synthetic Polynucleotide

```
<400> SEQUENCE: 68
tgtagtcact atcggaataa gggcgacacg gatatg                                  36

<210> SEQ ID NO 69
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 69
catatccgtg tcgcccctt                                                     18

<210> SEQ ID NO 70
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 70
catatccgtg tcgcccttau uccgauagug acuaca                                  36

<210> SEQ ID NO 71
<211> LENGTH: 34
<212> TYPE: RNA
<213> ORGANISM: Artificial Sequence
<220> FEATURE:
<223> OTHER INFORMATION: Synthetic Polynucleotide

<400> SEQUENCE: 71
gucuuugaau aaagccugag uaggaagaaa aaaa                                    34

<210> SEQ ID NO 72
<211> LENGTH: 34
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: modified_base
<222> LOCATION: (15)..(16)
<223> OTHER INFORMATION: m5c

<400> SEQUENCE: 72
gucuuugaau aaagccugag uaggaagaaa aaaa                                    34
```

METHOD FOR NANOPORE RNA CHARACTERISATION

RELATED APPLICATIONS

This Application is a national stage filing under 35 U.S.C. § 371 of PCT International Application No. PCT/GB2015/053097, which has an international filing date of Oct. 19, 2015; is a continuation-in-part of PCT International Application No. PCT/GB2015/052916, which has an international filing date of Oct. 6, 2015; and claims foreign priority benefits under 35 U.S.C. § 119(a)-(d) or 35 U.S.C. § 365(b) of British application number 1418459.2, filed Oct. 17, 2014, British application number 1508270.4, filed May 14, 2015, and British application number 1517634.0, filed Oct. 6, 2015. The contents of each of the aforementioned applications are herein incorporated by reference in their entireties.

FIELD OF THE INVENTION

The invention relates to a new method of characterising a target RNA polynucleotide by taking one or more measurements as the target RNA polynucleotide moves with respect to a transmembrane pore. The movement of the target RNA polynucleotide with respect to the transmembrane pore is controlled by a DNA helicase enzyme and the target RNA polynucleotide is modified to increase DNA helicase binding thereto. The invention also relates to a modified RNA construct wherein the RNA polynucleotide has been modified to increase DNA helicase binding thereto.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a polynucleotide binding protein to control the movement of the polynucleotide through the pore.

Messenger RNA provides a view of the dynamic state of an organism and the benefits and applications of direct RNA sequencing are vast, including use in health screening; for example metastasis progression in certain cancers and heart disease. Direct RNA sequencing also has applications in investigating disease resistance in crops, determining the response to stresses, for example; drought. UV and salinity and in cellular differentiation and determination during emblyogenesis.

A problem which occurs in direct sequencing of RNA, particularly those of 500 nucleotides or more, is finding a suitable molecular motor which can control translocation of the RNA through a transmembrane pore. To date, a molecular motor that engages with RNA and provides consistent movement has not been shown. Consistent movement of the RNA polymer and the ability to read long segments of the polymer is desirable for characterising or sequencing the polynucleotide.

International Patent Application No. PCT/GB2014/053121 (WO 2015/056028) describes a method of characterising a target ribonucleic acid (RNA) involving forming a complementary polynucleotide and then characterising the complementary polynucleotide using a transmembrane pore. Such indirect RNA characterisation is prone to error and can result in the loss of vital information regarding, for example, methylation status of the RNA. Other important modifications can also be hidden in the conversion of RNA to cDNA.

SUMMARY OF THE INVENTION

The inventors have surprisingly demonstrated that it is possible to characterise a target RNA polynucleotide by taking one or more measurements as the target RNA polynucleotide moves with respect to a transmembrane pore under the control of a DNA helicase enzyme. Accordingly, in one embodiment, a method for increasing the ability or efficiency of an RNA to be sequenced through a pore is provided. In another embodiment, a method of generating a modified RNA capable of being sequenced through a pore with greater efficiency than the RNA in unmodified form is also provided. The invention therefore provides a method of characterising a target RNA polynucleotide comprising:

a) providing (i) an RNA polynucleotide wherein the RNA polynucleotide is modified to comprise a non-RNA polynucleotide and (ii) a DNA helicase enzyme;

b) contacting the RNA polynucleotide and DNA helicase enzyme provided in a) with a transmembrane pore such that the DNA helicase controls the movement of the RNA polynucleotide through the transmembrane pore;

c) taking one or more measurements as the target RNA polynucleotide moves with respect to the transmembrane pore, wherein the measurements are indicative of one or more characteristics of the RNA polynucleotide, and thereby characterising the target RNA polynucleotide.

The modification of the RNA polynucleotide to comprise a non-RNA polynucleotide (such as a polynucleotide region or sequence or construct) results in increased DNA helicase binding thereto. A "non-RNA polynucleotide" as defined herein is a polynucleotide wherein at least one nucleotide of the polynucleotide is not a ribonucleotide, i.e. is not from RNA. The non-RNA polynucleotide may therefore comprise at least one ribonucleotide (or RNA nucleotide) but must also additionally comprise or include a non-RNA nucleotide or sequence i.e., a nucleotide or sequence of nucleotides that is not RNA. In a preferred embodiment of the invention the non-RNA polynucleotide (which may or may not comprise at least one ribonucleotide or RNA nucleotide) comprises DNA or DNA analogue, preferably a DNA helicase binding site or a DNA adaptor. Preferably the non-RNA polynucleotide comprises a leader sequence which preferentially threads into the pore. Accordingly the non-RNA polynucleotide is read first, followed by the target RNA sequence to be characterised.

The invention provides a construct which is a "hybrid" polynucleotide comprising (i) an RNA polynucleotide and (ii) a non-RNA polynucleotide. Preferably the non-RNA polynucleotide comprises a DNA polynucleotide, wherein the DNA polynucleotide comprises or comprises only a DNA helicase binding site. Preferably the non-RNA polynucleotide further comprises a leader sequence which preferentially threads into a nanopore. More preferably the non-RNA polynucleotide further comprises a barcoding section on the polynucleotide strand. The barcoding section is preferably located between the leader sequence and the DNA helicase binding site. The barcoding section enables unambiguous identification of an analyte i.e., informing the user which of several samples is being sequenced.

The modification of a target RNA polynucleotide to comprise a non-RNA polynucleotide may involve the attachment of a non-RNA polynucleotide (possibly comprising an RNA sequence or at least one ribonucleotide) to the target RNA polynucleotide using any suitable attachment method, including one or more of the attachment methods described herein. As described herein, the attachment of a non-RNA polynucleotide to a target RNA is synonymous with the attachment of a target RNA to a non-RNA polynucleotide. Where the non-RNA polynucleotide comprises a ribonucleotide or an RNA sequence, the non-RNA polynucleotide may be attached to the target RNA polynucleotide via the ribonucleotide or RNA which is comprised within the non-RNA polynucleotide.

The non-RNA polynucleotide can be attached to the target RNA polynucleotide by a covalent bond formed between at least one reactive group on each of the target RNA polynucleotide and the non-RNA polynucleotide. The non-RNA polynucleotide can be chemically or enzymatically ligated to the RNA polynucleotide. The non-RNA polynucleotide can additionally or alternatively be attached to the RNA polynucleotide by hybridisation and/or using one or more topoisomerases. Preferably the one or more characteristics to be determined by the method are selected from (i) length of the RNA polynucleotide, (ii) identity of the RNA polynucleotide, (iii) the sequence of the RNA polynucleotide. (iv) the secondary structure of the RNA polynucleotide and (v) whether or not the RNA polynucleotide is modified. The one or more characteristics of the RNA polynucleotide can be measured by electrical and/or optical measurement. Preferably step c) comprises measuring the current passing through the transmembrane pore as the RNA polynucleotide moves with respect to the transmembrane pore wherein the current is indicative of one or more characteristics of the RNA polynucleotide and thereby characterising the RNA polynucleotide.

The target RNA polynucleotide to be characterised may be additionally or further modified by methylation, by oxidation, by damage, with one or more proteins or with one or more labels, tags or spacers. The target RNA may contain base analogues. The RNA polynucleotide can be coupled to the membrane using one or more anchors.

Preferably the DNA helicase comprises a modification to reduce the size of an opening in the polynucleotide binding domain through which in at least one conformational state the RNA polynucleotide can unbind from the helicase. In one embodiment of the invention, the movement of the RNA polynucleotide is controlled by a series of one or more DNA helicases. The one or more helicases are a) Hel308 helicases, RecD helicases, XPD helicases or Dda helicases (b) helicases derived from any of the helicases in (a); or (c) a combination of any of the helicases in (a) and/or (b). The method may further comprise the use of one or more molecular brakes that are derived from helicases and are modified such that they bind the polynucleotide but do not function as a helicase.

The transmembrane pore can by a protein pore or a solid state pore. Preferably the transmembrane protein pore is a protein pore and is derived from a hemolysin, leukocidin, *Mycobacterium smegmatis* porin A (MspA), MspB, MspC, MspD, lysenin, CsgG, outer membrane porin F (OmpF), outer membrane porin G (OmpG), outer membrane phospholipase A, *Neisseria* autotransporter lipoprotein (NalP) and WZA.

The invention also provides a method of moving a target RNA polynucleotide with respect to a transmembrane pore when the movement is controlled by a DNA helicase enzyme, comprising:

a) providing (i) an RNA polynucleotide wherein the RNA polynucleotide is modified to comprise a non-RNA polynucleotide and a (ii) DNA helicase enzyme;

b) contacting the RNA polynucleotide and DNA helicase enzyme provided in a) with a transmembrane pore such that the DNA helicase controls the movement of the RNA polynucleotide with respect to the transmembrane pore.

The modification of the RNA polynucleotide to comprise a non-RNA polynucleotide results in increased DNA helicase binding thereto. In one embodiment of the invention the method comprises pre-binding the DNA helicase to the modified RNA polynucleotide before the contacting step.

The method of the invention provides more consistent movement of the RNA polynucleotide with respect to the transmembrane pore. The invention also provides a "hybrid" polynucleotide comprising (i) an RNA polynucleotide and (ii) a non-RNA polynucleotide. Preferably the non-RNA polynucleotide comprises a DNA polynucleotide, wherein the DNA polynucleotide comprises or comprises only a DNA helicase binding site. Preferably the non-RNA polynucleotide further comprises a leader sequence which preferentially threads into a nanopore. More preferably the non-RNA polynucleotide further comprises a barcoding section on the polynucleotide strand. The barcoding section is preferably located between the leader sequence and the DNA helicase binding site. The barcoding section enables unambiguous identification of an analyte i.e., informing the user which of several samples is being sequenced.

The invention also provides a combination of a target RNA polynucleotide and a DNA helicase in which a part of the RNA polynucleotide has been modified to interact with or bind to the DNA helicase. Preferably the RNA is modified to comprise a non-RNA polynucleotide, most preferably the non-RNA polynucleotide is DNA or a DNA analogue.

The invention also provides a kit for characterising a target RNA polynucleotide. Preferably the kit comprises a non-RNA polynucleotide, which is adapted for attachment to a target RNA to be characterised. The invention also provides an apparatus for characterising a target RNA polynucleotide in a sample.

The modified RNA constructs described herein provide a binding site for the DNA helicase enzyme. The DNA helicase is essentially "tricked" into reading the RNA polynucleotide: Once the DNA helicase has bound to the non-RNA polynucleotide it can transition along the RNA polynucleotide. The helicase may transition along the RNA in solution. The helicase may require the presence of the nanopore to facilitate the movement of the helicase along the RNA polynucleotide. The movement of the helicase along the RNA may be facilitated by a nanopore and via the application of an applied field across the nanopore.

The ability to translocate an entire RNA construct through a nanopore under the control of a DNA helicase allows characteristics of the RNA polynucleotide, such as its sequence, to be estimated with improved accuracy and speed over known methods: The methods of the present invention are free from PCR bias, as compared with prior art methods. Modifications in RNA can be detected and non-coding isoforms and splice-variants can be correctly identified. RNA base analogues can be directly detected in the nanopore. The constructs described herein are particularly effective for achieving translocation of target RNAs of 500 nucleotides or more, for example 1000 nucleotides, 5000, 10000, 20000, 50000, 100000 or more.

In the methods of the invention the DNA helicase is essentially "tricked" into reading the target RNA sequence by virtue of the presence of a non-RNA leader sequence. Once movement of the DNA helicase is initiated by the non-RNA polynucleotide (which may comprise DNA or a DNA analogue), it can continue to move along the RNA. The methods of the invention also provide means to differentiate RNA and DNA from each other as a function of mean amplitude and range, even when the RNA and DNA sequences are the same.

Figure 3:
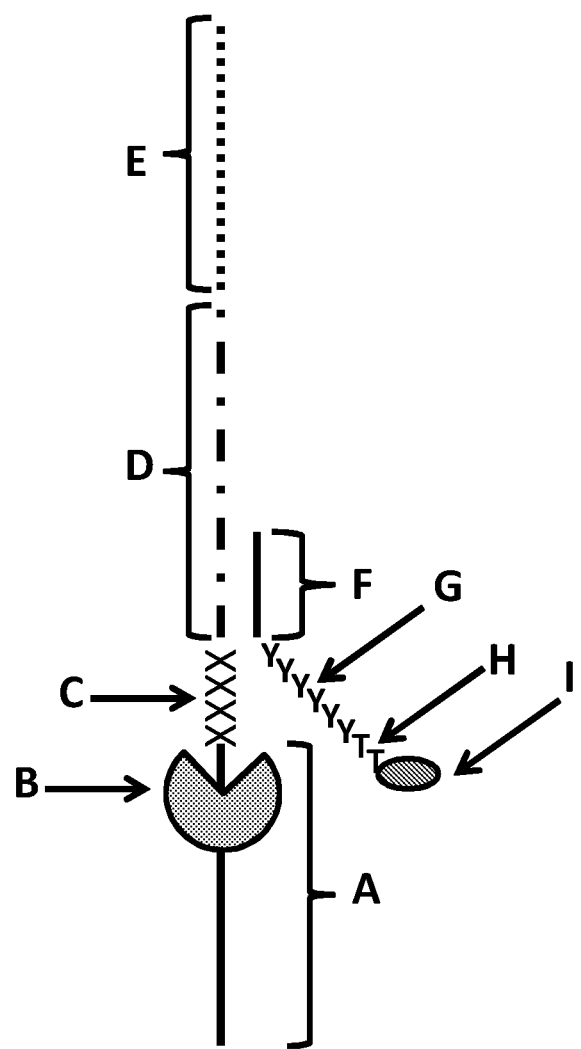
FIG. 3 shows a cartoon representation of the DNA/RNA strand which was translocated through an MspA nanopore using a DNA helicase (T4 Dda-E94C/A360C (SEQ ID NO: 14 with mutations E94C/A360C and then (ΔM1)G1)) in Example 1. Region A corresponds to the 40 nucleotide poly(dT) leader (SEQ ID NO: 16) to which the DNA helicase (labelled B) binds. Region A is attached to four iSpC3 spacers (shown as X's and labelled C). Region D corresponds to the synthetic RNA region (SEQ ID NO: 17). Region E corresponds to the variable length poly(U). Region F is the DNA (SEQ ID NO: 18) which is hybridised to Region D. Attached to the DNA (SEQ ID NO: 18) is six iSp18 spacers (shown as Y's and labelled G) two thymines (shown as T's and labeled H) and a 3' cholesterol TEG (labelled 1).
Figure 11:
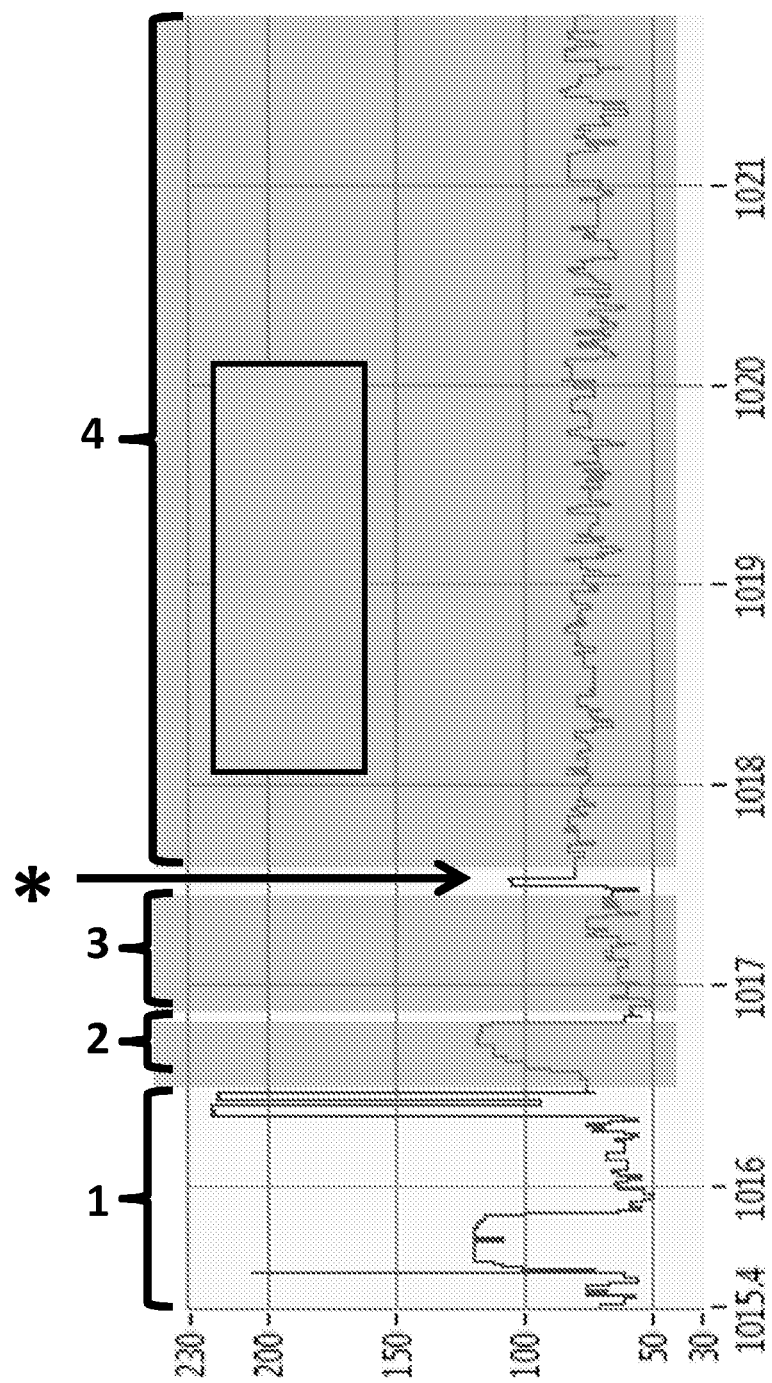

FIG. 11 shows an example trace of a helicase controlled DNA movement (y-axis=current (pA), x-axis=time (s)) where the DNA helicase (T4 Dda-E94C/A360C (SEQ ID NO: 14 with mutations E94C/A360C and then (ΔM1)G1)) controlled the movement of the DNA/RNA product produced by Example 3A (cartoon representation shown in FIG. 3). Region 1 corresponds to the DNA leader that has not ligated onto the RNA (DNA X1), region 2 corresponds to SEQ ID NO: 22 attached to the four iSp18 spacers (the spacers allow a larger amount of current to flow through the nanopore than the DNA or RNA regions), region 3 corresponds to a DNA sequence (SEQ ID NO: 23) and region 4 corresponds to the Firefly luciferase mRNA region (RNA X1, mRNA with an open reading frame of SEQ ID NO: 26 which has a 5'-hexynl-G as the 5' most nucleotide and has a 3' polyA tail). The peak in current labelled with a * corresponds to the translocation of the click linkage which is made when the DNA and RNA are joined.

Figure 12:
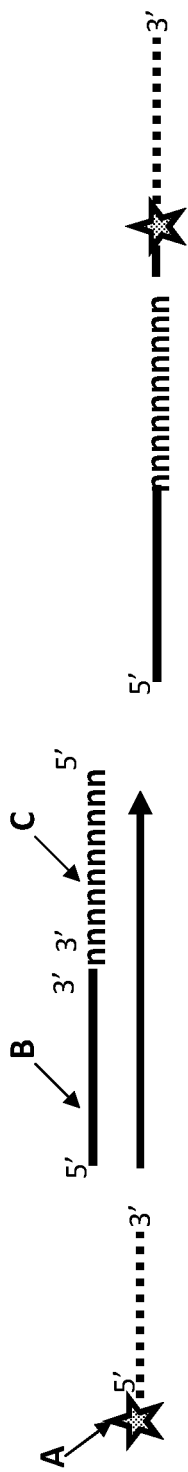

FIG. 12 shows a cartoon representation of a method of attaching a strand of eukaryotic RNA (shown as a dashed line) to a strand of DNA (shown as a solid line). The eukaryotic RNA has a 7-methylguanosine cap which runs in the opposite orientation to the rest of the RNA strand (i.e., the 5' end comprises reversed bases, shown as a star shape and labelled A). The eukaryotic RNA is ligated to a strand of DNA (labelled B) which comprises a region of reversed DNA bases (shown as a random sequence of n's and labelled C). In the region of reversed bases the bases also run in the opposite direction. This illustrates that the two regions of reversed bases on the RNA and DNA can be ligated together.

Figure 13:
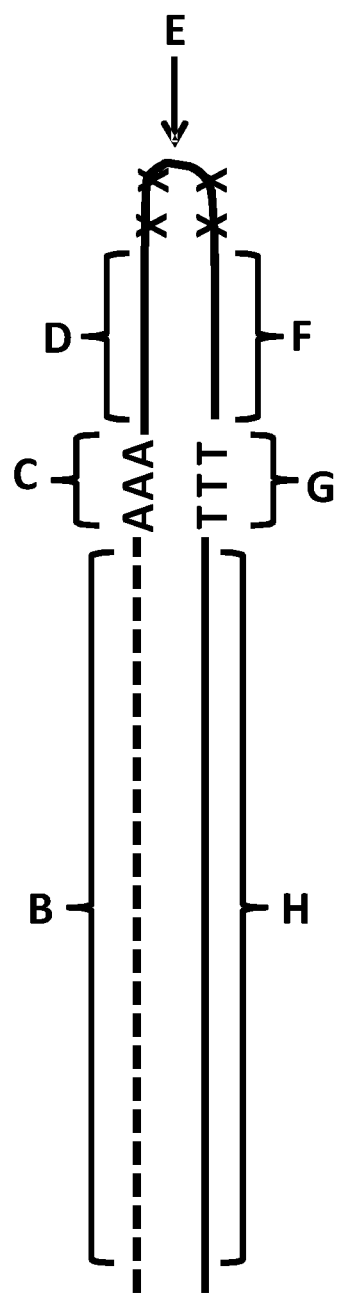

FIG. 13 shows a cartoon representation of the RNA/cDNA construct which was produced in Example 4. Region B corresponds to SEQ ID NO: 30. Region C corresponded to the last three adenines in SEQ ID NO: 30. Region D corresponds to the SEQ ID NO: 29 in both the 3T and 10T hairpins. Region E corresponds to four iSpC3 spacers (shown as X's). Region F corresponds to SEQ ID NO 27 in the 3T hairpin and SEQ ID NO: 28 in the 10T hairpin. Region G corresponds to the last three thymines in SEQ ID NO: 27 or 28. Region H corresponds to the cDNA which was produced during the reverse transcription of RNA strand SEQ ID NO: 30.

Figure 14:
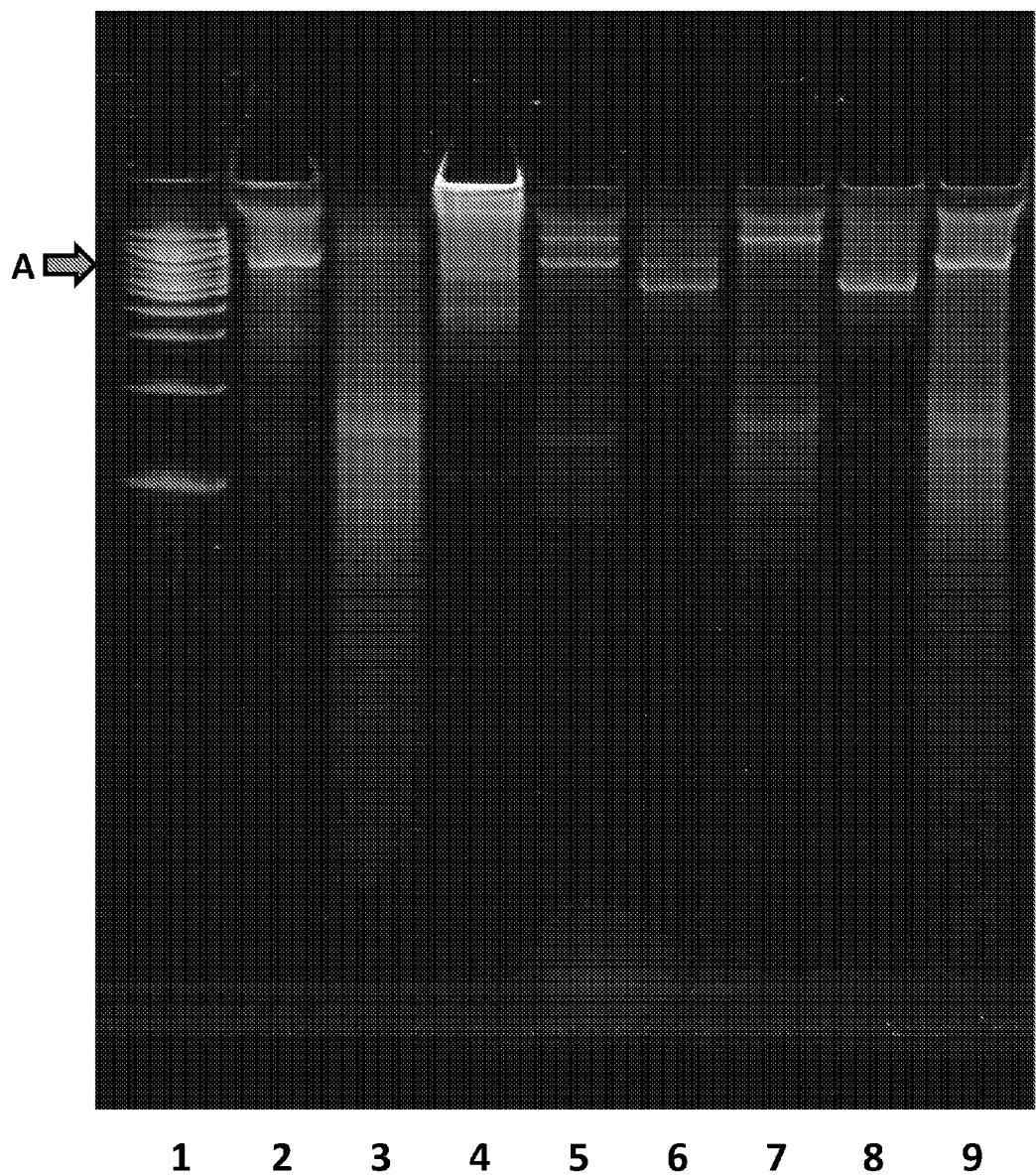

FIG. 14 shows a 10% PAGE TBE-Urea denaturing gel (run at 140 V for 60 minutes) showing various samples from Example 4 before and after hairpin ligation and reverse transcription. Lane 1 shows a TriDye™ ladder. Lane 2 shows the RNA strand used in Example 4 (SEQ ID NO: 30) before ligation or reverse transcription. Lane 3 shows the 10T hairpin control (SEQ ID NO: 29 is attached at its 5' end to a phosphate group and is attached at its 3' end to four iSpC3 spacers which are attached at the opposite end to the 5' end of SEQ ID NO: 28) before ligation or reverse transcription. Lane 4 shows the RNA strand (SEQ ID NO: 30) after reverse transcription using a primer. Lane 5 shows the RNA strand (SEQ ID NO: 30) after ligation to the 3T hairpin (SEQ ID NO: 29 is attached at its 5' end to a phosphate group and is attached at its 3' end to four iSpC3 spacers which are attached at the opposite end to the 5' end of SEQ ID NO: 27). Lane 6 shows the RNA strand (SEQ ID NO: 30) after ligation to the 3T hairpin (SEQ ID NO: 29 is attached at its 5' end to a phosphate group and is attached at its 3' end to four iSpC3 spacers which are attached at the opposite end to the 5' end of SEQ ID NO: 27) and subsequent reverse transcription. Lane 7 shows the RNA strand (SEQ ID NO: 30) after ligation to the 10T hairpin (SEQ ID NO: 29 is attached at its 5' end to a phosphate group and is attached at its 3' end to four iSpC3 spacers which are attached at the opposite end to the 5' end of SEQ ID NO: 28). Lane 8 shows the RNA strand (SEQ ID NO: 30) after ligation to the 10T hairpin (SEQ ID NO: 29 is attached at its 5' end to a phosphate group and is attached at its 3' end to four iSpC3 spacers which are attached at the opposite end to the 5' end of SEQ ID NO: 28) and subsequent reverse transcription. Lane 9 shows a control experiment where the RNA strand and the 10T hairpin were incubated together in the absence of a ligase. Arrow A corresponds to the RNA strand used in Example 4 (SEQ ID NO: 30).

Figure 15:
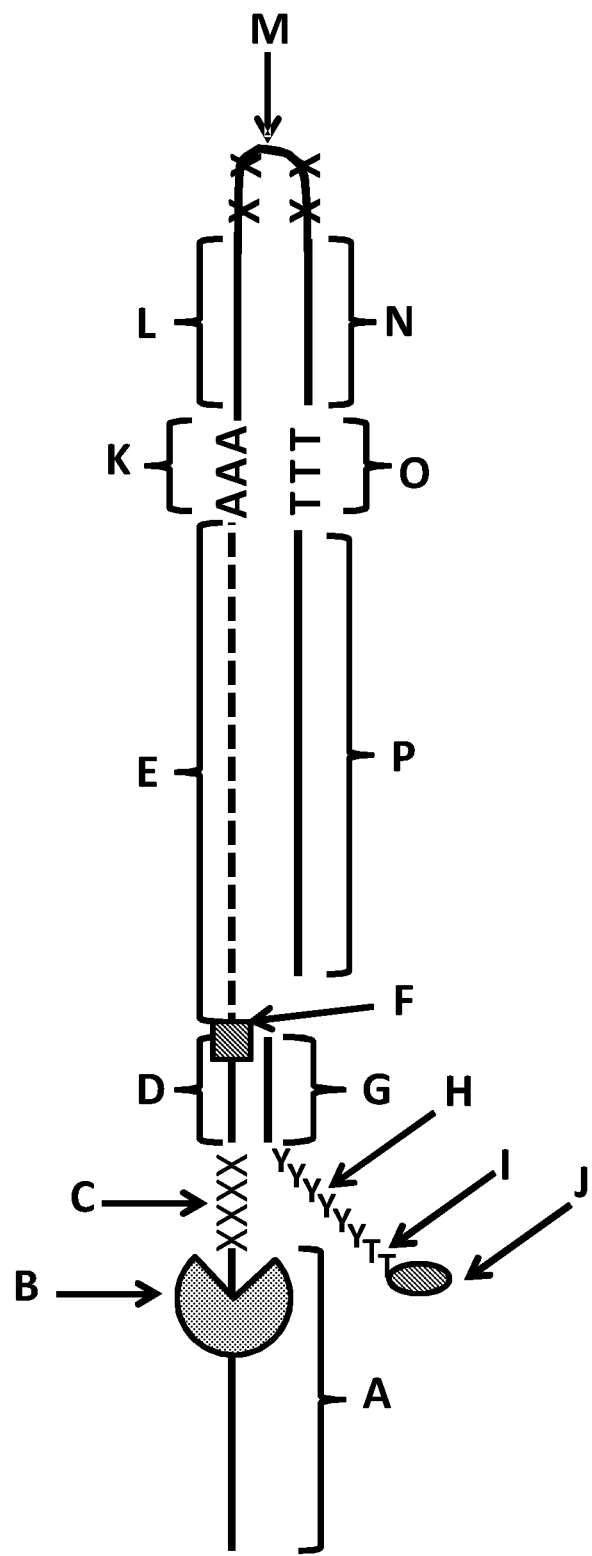

FIG. 15 shows a cartoon representation of the DNA/RNA/cDNA strand produced in Example 5 which was translocated through an MspA nanopore using a DNA helicase (T4 Dda-E94C/C109A/C136A/A360C (SEQ ID NO: 14 with mutations E94C/C109A/C136A/A360C and then (ΔM1) G1)). Region A corresponds to the DNA leader (SEQ ID NO: 22) to which the DNA helicase (labelled B) binds. Region A is attached to four iSp18 spacers (shown as X's and labelled C). Region D corresponds to a second DNA sequence (SEQ ID NO: 23). Region E corresponds to the firefly luciferase mRNA with a 5'-hexynl-G region (RNA X1, mRNA with an open reading frame of SEQ ID NO: 26 which has a 5'-hexynl-G as the 5' most nucleotide and has a 3' polyA tail). Regions D and E are attached by click chemistry. The reacted azide and hexynl groups are represented by a box (labelled F). Region G is the DNA (SEQ ID NO: 18) which is hybridised to Region D. Attached to the DNA (SEQ ID NO: 18) is six iSp18 spacers (shown as Y's and labelled H) two thymines (shown as T's and labeled I) and a 3' cholesterol TEG (labelled J). Region K corresponds to the last three adenines in FLuc mRNA (RNA X1, mRNA with an open reading frame of SEQ ID NO: 26 which has a 5'-hexynl-G as the 5' most nucleotide and has a 3' polyA tail). Region L corresponds to the SEQ ID NO: 29 in the 10T hairpin. Region M corresponds to four iSpC3 spacers (shown as X's). Region N corresponds to SEQ ID NO: 28 in the 10T hairpin. Region O corresponds to the last three thymines in SEQ ID NO: 28. Region P corresponds to the cDNA which was produced during the reverse transcription of the RNA strand RNA X1, mRNA with an open reading frame of SEQ ID NO: 26 which has a 5'-hexynl-G as the 5' most nucleotide and has a 3' polyA tail.

Figure 16:
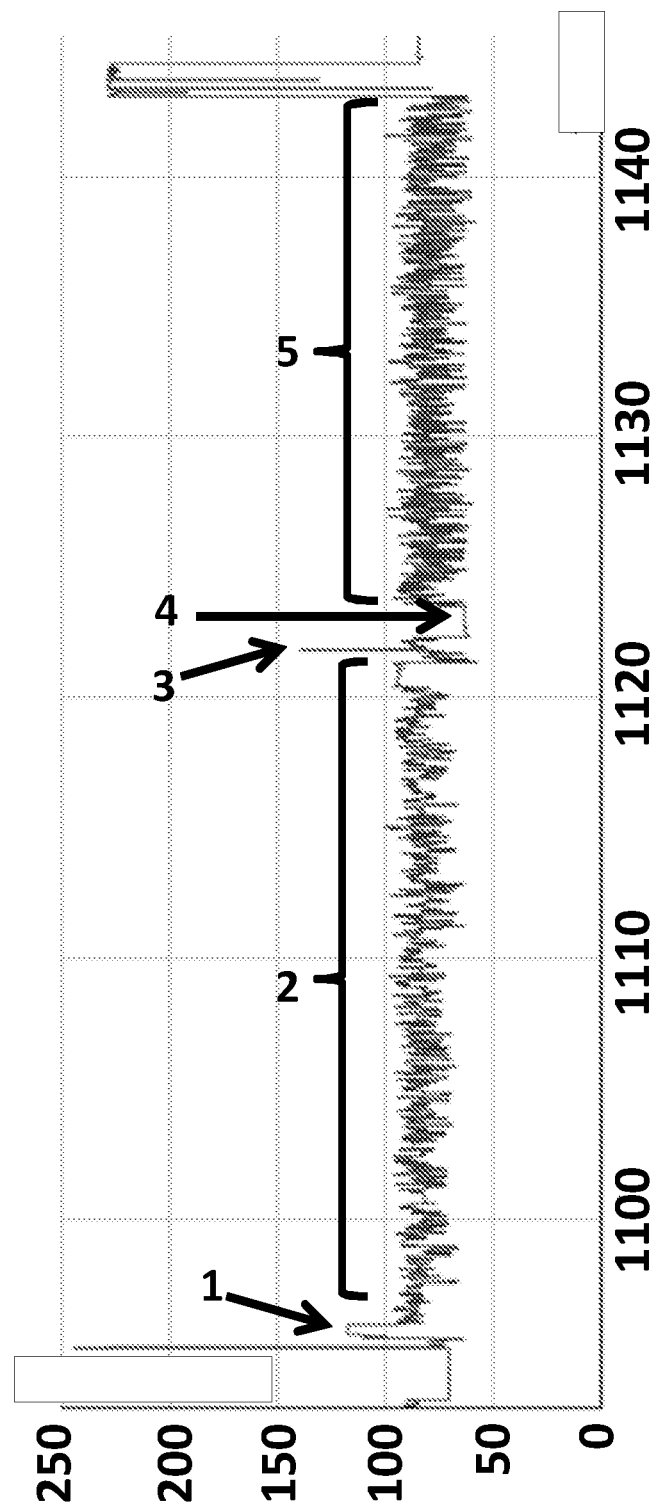

FIG. 16 shows an example trace of a helicase controlled DNA movement (y-axis=current (pA), x-axis=time (s)) where the DNA helicase (T4 Dda-E94C/C109A/C136A/A360C (SEQ ID NO: 14 with mutations E94C/C109A/C136A/A360C and then (ΔM1)G1)) controlled the movement of the DNA/RNA/cDNA product produced by Example 5 (cartoon representation shown in FIG. 15). Region 1 corresponds to the DNA leader (DNA X1), region 2 corresponds to the Firefly luciferase mRNA region (RNA X1, mRNA with an open reading frame of SEQ ID NO: 26 which has a 5'-hexynl-G as the 5' most nucleotide and has a 3' polyA tail), region 3 corresponds to the four iSpC3 spacers, region 4 corresponds to the polyT region of the 10T hairpin, region 5 corresponds to the cDNA which was produced by reverse transcription of the mRNA.

Figure 17:
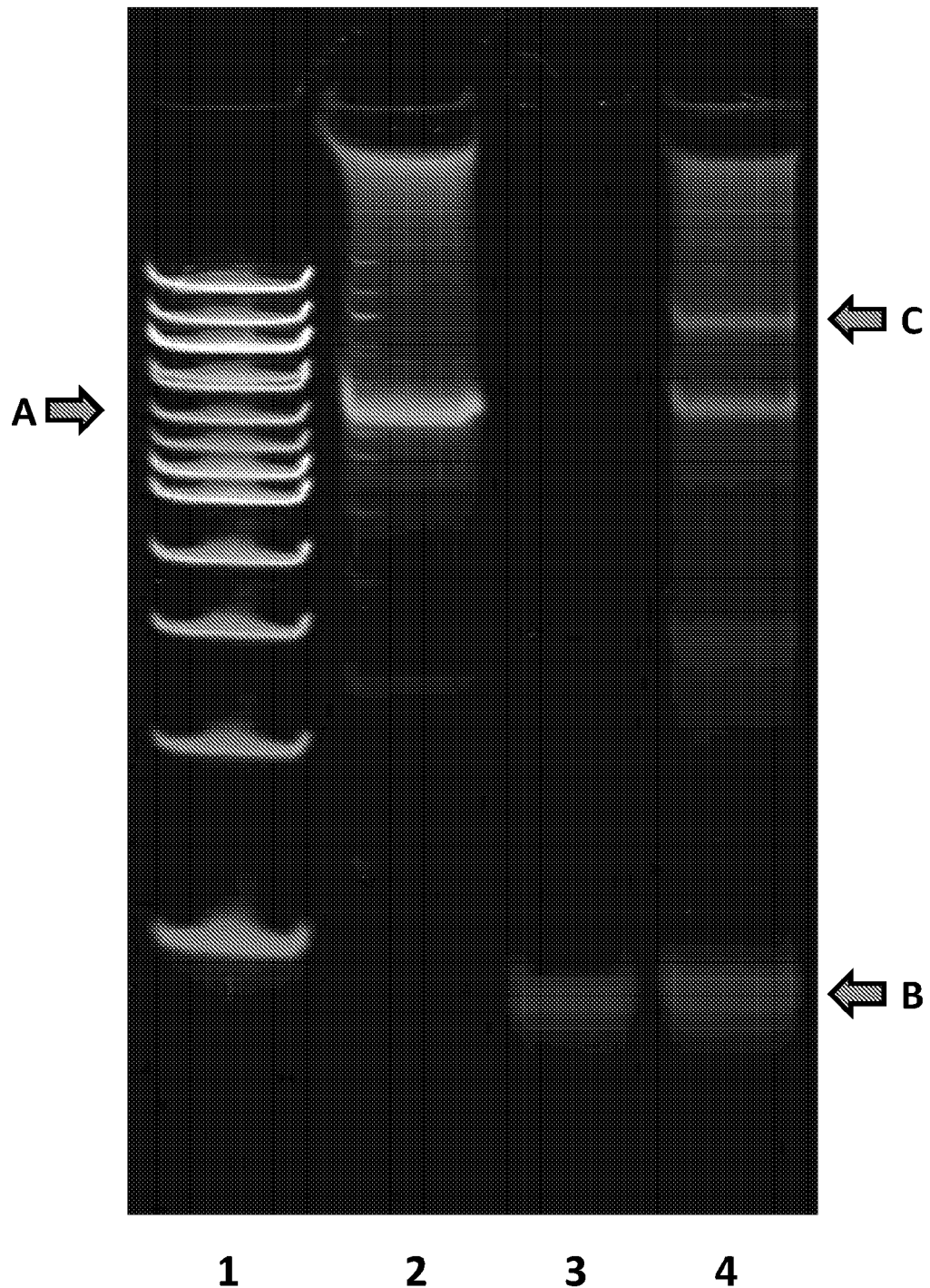

FIG. 17 shows a 5% PAGE TBE-Urea denaturing gel (run at 140 V for 60 minutes) showing various samples from Example 5 before and after decapping and ligation. Lane 1 shows a TriDye™ ladder. Lane 2 shows the capped RNA strand (SEQ ID NO: 30 which has a 7-methylguanosine cap connected to the 5' end of the strand by a 5' to 5' triphosphate linkage). Lane 3 shows the non-RNA polynucleotide (30 SpC3 spacers attached to the 5' end of SEQ ID NO: 31 which was attached at the 3' end to four iSp18 spacers which were attached at the opposite end to the 5' end of SEQ ID NO: 32 which was attached at the 3' end to four 5-nitroindoles which were attached at the opposite end to the RNA sequence CAAGGG). Lane 4 shows the RNA strand (SEQ ID NO: 30) after ligation to the non-RNA polynucleotide (30 SpC3 spacers attached to the 5' end of SEQ ID NO: 31 which was attached at the 3' end to four iSp18 spacers which were attached at the opposite end to the 5' end of SEQ ID NO: 32 which was attached at the 3' end to four 5-nitroindoles which were attached at the opposite end to the RNA sequence CAAGGG). Arrow A corresponds to the RNA strand (SEQ ID NO: 30). Arrow B corresponds to the non-RNA polynucleotide. Arrow C corresponds to the ligated product where the RNA strand has been ligated to the non-RNA polynucleotide.

Figure 18:
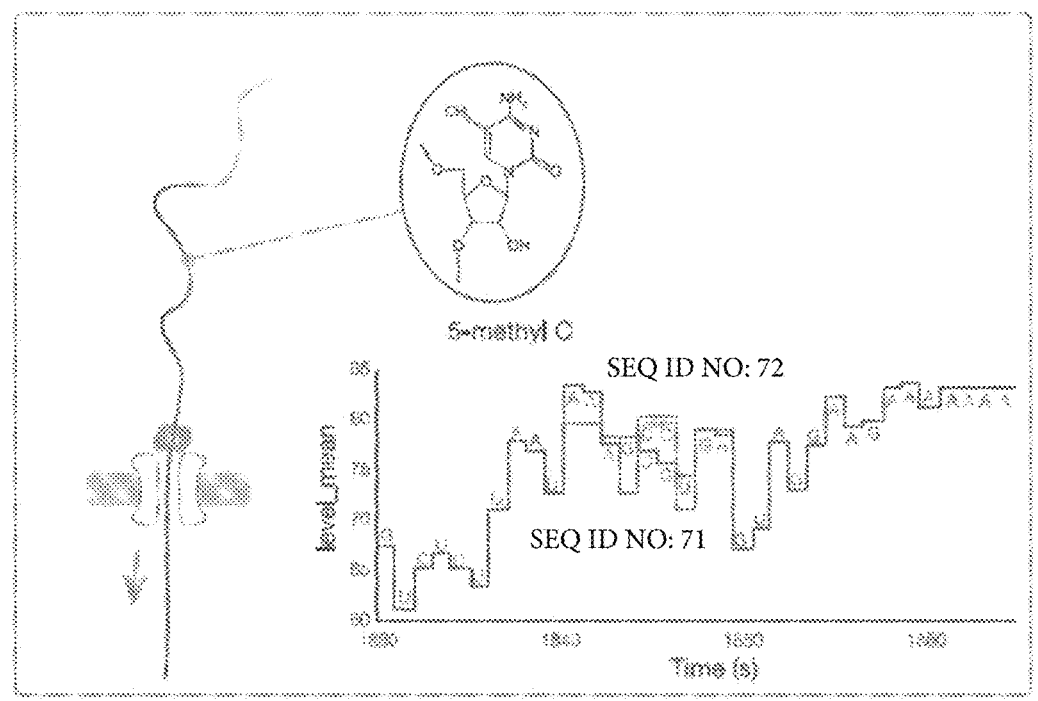

FIG. 18 illustrates consensus current levels from RNA with and without modified bases. This figure shows that modified bases affect several consecutive current levels.

Figure 19:
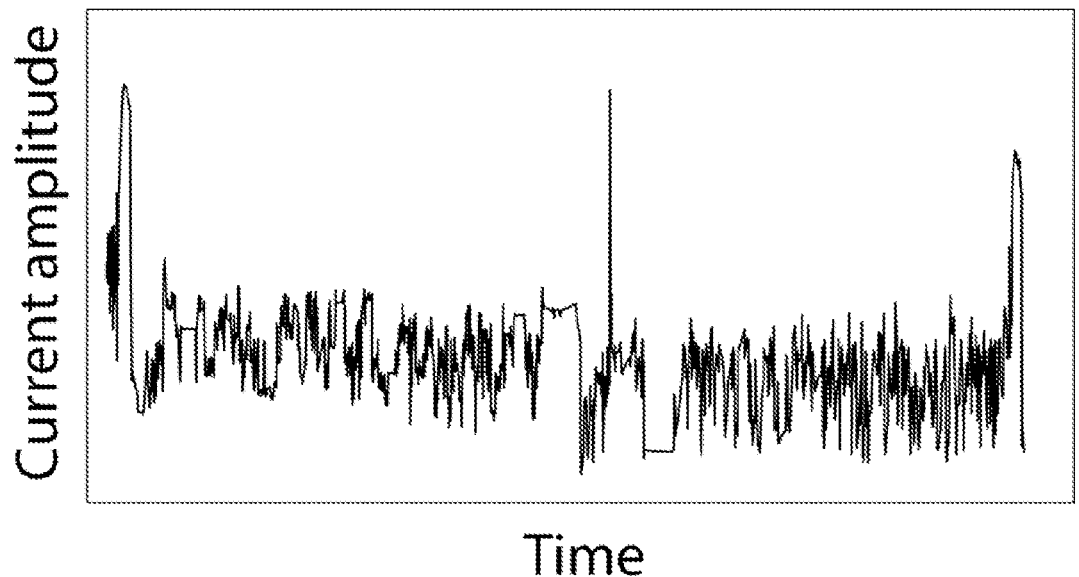

FIG. 19 shows a DNA helicase controlled translocation of an RNA-DNA 2D strand (RNA-sense and DNA-antisense) through the nanopore. FIG. 19 demonstrates the different mean amplitude and range observed for RNA versus DNA.

Figure 20:
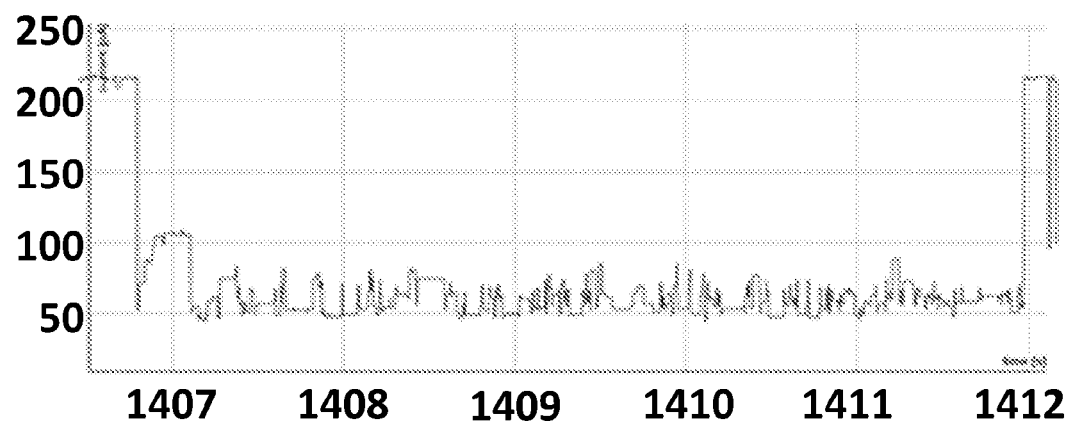

FIG. 20 shows an example trace of a helicase controlled DNA movement (y-axis=current (pA), x-axis=time (s)) where the DNA helicase (Hel308Mbu-E284C/S615C (SEQ ID NO: 8 with mutations E284C/S615C)) controlled the movement of the DNA/RNA product produced by Example 8.

Figure 21:
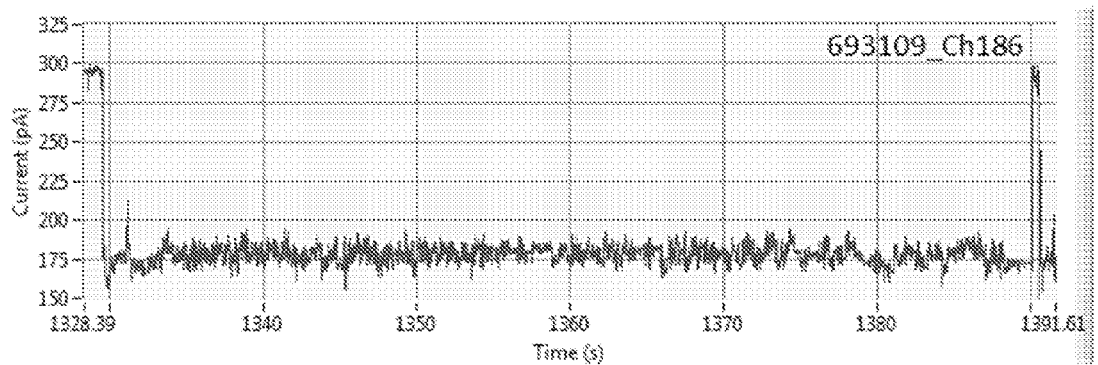

FIG. 21 shows an example trace of a helicase controlled DNA movement (y-axis=current (pA), x-axis=time (s)) through a lysenin mutant where the DNA helicase (and T4 Dda-E94C/A360C (0.36 µl, 3.8 µM), SEQ ID NO: 14 with mutations E94C/A360C and then (ΔM1)G1) controlled the movement of the DNA/RNA product produced by Example 3.

Figure 22:
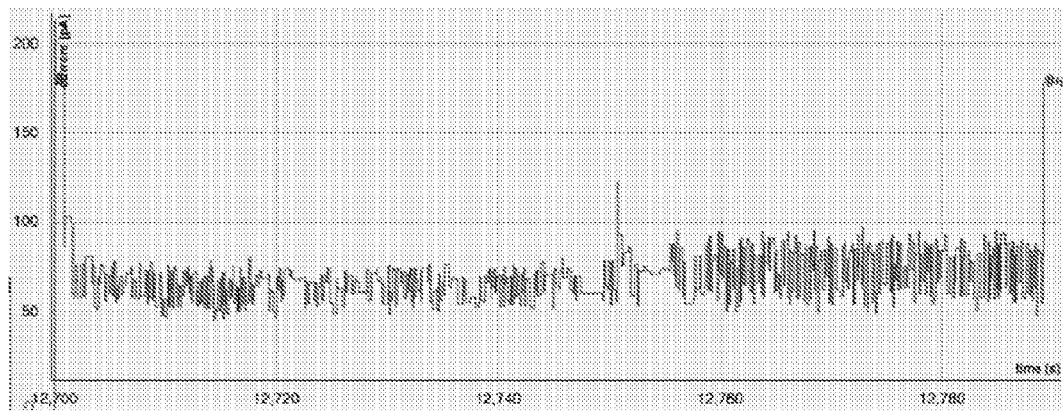

FIG. 22 shows an example trace of a helicase controlled DNA movement (y-axis=current (pA), x-axis=time (s)) through a CsgG mutant pore (CsgG-Eco-(Y51T/F56Q)-StrepII(C))9 (SEQ ID NO: 44 with mutations Y51T/F56Q where StepII(C) is SEQ ID NO: 45 and is attached at the C-terminus)) where the DNA helicase (Hel308Mbu-E284C/S615C (SEQ ID NO: 8 with mutations E284C/S615C)) controlled the movement of the DNA/RNA product produced by Example 5.

DESCRIPTION OF THE SEQUENCE LISTING

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the amino acid sequence of Hel308 Mbu.

SEQ ID NO: 9 shows the amino acid sequence of Hel308 Csy.

SEQ ID NO: 10 shows the amino acid sequence of Hel308 Tga.

SEQ ID NO: 11 shows the amino acid sequence of Hel308 Mhu.

SEQ ID NO: 12 shows the amino acid sequence of TraI Eco.

SEQ ID NO: 13 shows the amino acid sequence of XPD Mbu.

SEQ ID NO: 14 shows the amino acid sequence of Dda 1993.

SEQ ID NO: 15 shows the amino acid sequence of Trwc Cba.

SEQ ID NO: 16 shows a polynucleotide sequence used in Example 1.

SEQ ID NO: 17 shows a polynucleotide sequence used in Example 1.

SEQ ID NO: 18 shows a polynucleotide sequence used in Example 1 and 3.

SEQ ID NO: 19 shows a polynucleotide sequence used in Example 2. This sequence has a 5' phosphate group.

SEQ ID NO: 20 shows a polynucleotide sequence used in Example 2.

SEQ ID NO: 21 shows a polynucleotide sequence used in Example 2. This sequence has a 5' CY®3 group.

SEQ ID NO: 22 shows a polynucleotide sequence used in Example 3.

SEQ ID NO: 23 shows a polynucleotide sequence used in Example 3. This sequence has a 3' AzideN group.

SEQ ID NO: 24 shows a polynucleotide sequence used in Example 3.

SEQ ID NO: 25 shows a polynucleotide sequence used in Example 3. This sequence has a 3' AzideN group and a 5' CY®3 group.

SEQ ID NO: 26 shows the open reading frame of a polynucleotide sequence used in Examples 3 and 5. This sequence has 5'-hexynl group attached to the first G in the sequence.

SEQ ID NO: 27 shows a polynucleotide sequence used in Examples 4 and 5.

SEQ ID NO: 28 shows a polynucleotide sequence used in Example 4.

SEQ ID NO: 29 shows a polynucleotide sequence used in Examples 4 and 5.

SEQ ID NO: 30 shows a polynucleotide sequence used in Examples 4 and 6.

SEQ ID NO: 31 shows a polynucleotide sequence used in Example 6.

SEQ ID NO: 32 shows a polynucleotide sequence used in Example 6.

SEQ ID NO: 33 shows a sequence used to illustrate homopolymer read.

SEQ ID NO: 34 shows a sequence used to illustrate homopolymer read.

SEQ ID NO: 35 shows a polynucleotide sequence used in Example 8.

SEQ ID NO: 36 shows a polynucleotide sequence used in Example 8.

SEQ ID NO: 37 shows a polynucleotide sequence used in Example 8.

SEQ ID NO: 38 shows a polynucleotide sequence used in Example 8.

SEQ ID NO: 39 shows a polynucleotide sequence used in Example 8.

SEQ ID NO: 40 shows a polynucleotide sequence used in Example 8.

SEQ ID NO: 41 shows the polynucleotide sequence encoding the lysenin monomer.

SEQ ID NO: 42 shows the amino acid sequence of the the lysenin monomer.

SEQ ID NO: 43 shows the codon optimised polynucleotide sequence encoding the wild-type CsgG monomer from *Escherichia coli* Str. K-12 substr. MC4100. This monomer lacks the signal sequence.

SEQ ID NO: 44 shows the amino acid sequence of the mature form of the wild-type CsgG monomer from *Escherichia coli* Str. K-12 substr. MC4100. This monomer lacks the signal sequence. The abbreviation used for this CsgG=CsgG-Eco.

SEQ ID NO: 45 shows the amino acid sequence of StepII(C).

SEQ ID NOs: 46 to 64 are polynucleotide sequences described in the description.

SEQ ID NOs: 65 and 66 are polynucleotide sequences used in the Examples.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a". "an", and "the" include plural referents unless the content clearly dictates otherwise. Thus, for example, reference to "a polynucleotide" includes two or more polynucleotides, reference to "a polynucleotide binding protein includes two or more such proteins, reference to "a helicase" includes two or more helicases, reference to "a monomer" refers to two or more monomers, reference to "a pore" includes two or more pores and the like.

All publications, patents and patent applications cited herein, whether supra or infra, are hereby incorporated by reference in their entirety.

Characterising a Target RNA Polynucleotide

The method of the invention involves characterising a target RNA polynucleotide. The RNA polynucleotide is delivered to a transmembrane pore and the pore is used to characterise the RNA polynucleotide. The invention provides a method of characterising a target ribonucleic acid (RNA) polynucleotide by taking one or more measurements as the target RNA polynucleotide moves with respect to a transmembrane pore under the control of a DNA helicase enzyme.

Since the transmembrane pore is capable of detecting a single molecule of the target polynucleotide, there is no need for amplification of the target RNA polynucleotide. The method typically does not comprise polymerase chain reaction (PCR) or reverse transcription PCR (RT-PCR). This considerably reduces the amount of workflow needed to characterise a target RNA polynucleotide. It also avoids any biases and artifacts introduced by PCR.

The method of the invention may concern determining or measuring one or more characteristics of the RNA polynucleotide. The method may involve determining or measuring one, two, three, four or five or more characteristics of the RNA polynucleotide. The one or more characteristics are preferably selected from (i) the length or size of the RNA polynucleotide, (ii) the identity of the RNA polynucleotide (iii) the sequence of the RNA polynucleotide (iv) the secondary structure of the RNA polynucleotide and (v) whether or not the RNA polynucleotide is modified. Any combination of (i) to (v) may be measured in accordance with the invention, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}. Different combinations of (i) to (v) may be measured including any of those combinations listed above. The method of the invention preferably comprises estimating the sequence of or sequencing the RNA polynucleotide.

For (i), the length of the RNA polynucleotide may be measured for example by determining the number of interactions between the RNA polynucleotide and the pore or the duration of interaction between the RNA polynucleotide and the pore.

For (ii), the identity of the RNA polynucleotide may be measured in a number of ways. The identity of the RNA polynucleotide may be measured in conjunction with measurement of the sequence of the RNA polynucleotide or without measurement of the sequence of the RNA polynucleotide. The former is straightforward; the RNA polynucleotide is sequenced and thereby identified. The latter may be done in several ways. For instance, the presence of a particular motif in the RNA polynucleotide may be measured (without measuring the remaining sequence of the RNA polynucleotide). Alternatively, the measurement of a particular electrical and/or optical signal in the method may identify the RNA polynucleotide as coming from a particular source.

For (iii), the sequence of the RNA polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50): 17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded RNA polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each ribonucleotide. The methods of the invention can be used to distinguish between RNA and DNA even in a single sample: RNA and DNA can be differentiated from each other as a function of mean amplitude and range even when the RNA and DNA sequences are the same.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the RNA polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the RNA polynucleotide moves with respect to the pore. The current passing through the pore as the polynucleotide moves with respect to the pore is used to determine the sequence of the target RNA polynucleotide. This is Strand Sequencing. Suitable conditions for measuring ionic currents through transmembrane protein pores are known in the art and disclosed in the Examples. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different ribonucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a ribonucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method may be carried out in the presence of free nucleotides or free nucleotide analogues and/or an enzyme cofactor that facilitates the action of the helicase or construct. The method may also be carried out in the absence of free nucleotides or free nucleotide analogues and in the absence of an enzyme cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxyvthymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase or construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Target RNA

RNA is a macromolecule comprising two or more ribonucleotides. The target RNA polynucleotide may be eukaryotic or prokaryotic RNA. The target RNA polynucleotide may comprise any combination of any ribonucleotides. The ribonucleotides can be naturally occurring or artificial. One or more ribonucleotides in the target RNA polynucleotide can be oxidized or methylated. One or more ribonucleotides in the target RNA may be damaged. For instance, the target RNA may comprise a pyrimidine dimer, such as a uracil dimer. Such dimers are typically associated with damage by ultraviolet light and are the primary cause of skin melanomas. One or more ribonucleotides in the target RNA polynucleotide may be modified, for instance with a label or a tag. Suitable labels are described below. The target RNA may comprise one or more spacers.

A ribonucleotide typically contains a nucleobase, a ribose sugar and at least one phosphate group. The nucleobase is typically heterocyclic. Nucleobases include, but are not limited to, purines and pyrimidines and more specifically adenine, guanine, thymine, uracil and cytosine. The nucleotide typically contains a monophosphate, diphosphate or triphosphate. Phosphates may be attached on the 5' or 3' side of a nucleotide.

Ribonucleotides include, but are not limited to, adenosine monophosphate (AMP), guanosine monophosphate (GMP), thymidine monophosphate (TMP), uridine monophosphate (UMP), cytidine monophosphate (CMP), 5-methylcytidine monophosphate, 5-methylcytidine diphosphate, 5-methylcytidine triphosphate, 5-hydroxymethylcytidine monophosphate, 5-hydroxymethylcytidine diphosphate and 5-hydroxymethylcytidine triphosphate. The nucleotides are preferably selected from AMP, TMP, GMP, CMP and UMP.

A ribonucleotide may be abasic (i.e. lack a nucleobase). A ribonucleotide may also lack a nucleobase and a sugar (i.e. is a C3 spacer).

The ribonucleotides in the target RNA polynucleotide may be attached to each other in any manner. The ribonucleotides are typically attached by their sugar and phosphate groups as in nucleic acids. The ribonucleotides may be connected via their nucleobases as in pyrimidine dimers.

RNA is an extremely diverse molecule. The target RNA polynucleotide may be any naturally occurring or synthetic ribonucleotide molecule, e.g., RNA, messenger RNA (mRNA), Ribosomal RNA (rRNA), Heterogenous nuclear RNA (hnRNA), Transfer RNA (tRNA), Transfer-messenger RNA (tmRNA), Micro RNA (miRNA), Small nuclear RNA (snRNA), Small nucleolar RNA (snoRNA), Signal recognition particle (SRP RNA), SmY RNA, Small Cajal body-speicifc RNA (scaRNA), Guide RNA (gRNA), Spliced Leader RNA (SL RNA), Antisense RNA (asRNA), Long noncoding RNA (lncRNA), Piwi-interacting RNA (piRNA), Small interfering RNA (siRNA), Trans-acting siRNA (ta-siRNA), Repeat associated siRNA (rasiRNA), Y RNA, viral RNA or chromosomal RNA, all of which where appropriate may be single, double or triple stranded.

The target RNA polynucleotide is preferably messenger RNA (mRNA). The target mRNA may be an alternate splice variant. Altered amounts (or levels) of mRNA and/or alternate mRNA splice variants may be associated with diseases or conditions.

Alternatively the target RNA polynucleotide is a micro-RNA (or miRNA). One group of RNAs which are difficult to detect in low concentrations are micro-ribonucleic acids (micro-RNA or miRNAs). miRNAs are highly stable RNA oligomers, which can regulate protein production post-transcriptionally. They act by one of two mechanisms. In plants, miRNAs have been shown to act chiefly by directing the cleavage of messenger RNA, whereas in animals, gene regulation by miRNAs typically involves hybridisation of miRNAs to the 3' UTRs of messenger RNAs, which hinders translation (Lee et al., Cell 75, 843-54 (1993); Wightman et al., Cell 75, 855-62 (1993); and Esquela-Kerscher et al., Cancer 6, 259-69 (2006)). miRNAs frequently bind to their targets with imperfect complementarity. They have been predicted to bind to as many as 200 or more gene targets each and to regulate more than a third of all human genes (Lewis et al., Cell 120, 15-20 (2005)).

Suitable miRNAs for use in the invention are well known in the art. For instance, suitable miRNAs are stored on publically available databases (Jiang Q., Wang Y., Hao Y., Juan L., Teng M., Zhang X., Li M., Wang G., Liu Y., (2009) miR2Disease: a manually curated database for microRNA deregulation in human disease. Nucleic Acids Res.). The expression level of certain microRNAs is known to change in tumours, giving different tumour types characteristic patterns of microRNA expression (Rosenfeld, N. et al., Nature Biotechnology 26, 462-9 (2008)). In addition, miRNA profiles have been shown to be able to reveal the stage of tumour development with greater accuracy than messenger RNA profiles (Lu et al., Nature 435, 834-8 (2005) and Barshack et al., The International Journal of Biochemistry & Cell Biology 42, 1355-62 (2010)). These findings, together with the high stability of miRNAs, and the ability to detect circulating miRNAs in serum and plasma (Wang et al., Biochemical and Biophysical Research Communications 394, 184-8 (2010); Gilad et al., PloS One 3, e3148 (2008); and Keller et al., Nature Methods 8, 841-3 (2011)), have led to a considerable amount of interest in the potential use of microRNAs as cancer biomarkers. For treatment to be effective, cancers need to be classified accurately and treated differently, but the efficacy of tumour morphology evaluation as a means of classification is compromised by the fact that many different types of cancer share morphological features. miRNAs offer a potentially more reliable and less invasive solution.

The use of mRNAs and miRNAs to diagnose or prognose diseases or conditions are discussed in more detail below.

Any number of RNA's can be investigated. For instance, the method of the invention may concern determining the presence, absence or one or more characteristics of 3, 4, 5, 6, 7, 8, 9, 10, 20, 30, 50, 100 or more RNA molecules.

The polynucleotides can be naturally occurring or artificial. For instance, the method may be used to verify the sequence of two or more manufactured oligonucleotides. The methods are typically carried out in vitro.

The target RNA polynucleotide can be any length. For example, the RNA polynucleotide can be at least 10, at least 50, at least 100, at least 150, at least 200, at least 250, at least 300, at least 400 or at least 500 ribonucleotides in length. The target RNA can be 1000 or more ribonucleotides, 5000 or more ribonucleotides in length or 100000 or more ribonucleotides in length. The whole or only part of the target RNA may be characterised using this method. The part of the RNA to be sequenced preferably comprises all of the target molecule, but may for example be less than the entire molecule, e.g., between 4 bases and 1 kb, e.g., 4 to 100 bases.

The target RNA polynucleotide is typically present in or derived from any suitable sample. The invention is typically carried out on a sample that is known to contain or suspected to contain the target RNA polynucleotide. Alternatively, the invention may be carried out on a sample to confirm the identity of one or more target RNAs whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The target RNA polynucleotide may be derived from a eukaryotic cell or may be derived from a virus using a eukaryotic cell's transcription machinery. The invention may be carried out in vitro on a sample obtained from or extracted from any virus.

The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa or cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C. The target RNA polynucleotide is typically extracted from the sample before it is used in the method of the invention. RNA extraction kits are commercially available from, for instance, New England Biolabs® and Invitrogen®.

Modification of the Target RNA

The modification to the RNA polynucleotide may be any modification that facilitates DNA helicase binding and/or causes or has the effect of increased DNA helicase binding to the modified RNA polynucleotide. The term "binding" as used herein refers to affinity, or probability that the DNA helicase and substrate polynucleotide will be bound at any given time. Biochemically, this increase in affinity could be caused by an increase of the "on rate" or rate of binding, or a decrease of the "off rate" or rate of unbinding, or both an increase in "on rate" and a decrease in "off rate."

The modification of the RNA polynucleotide may increase the affinity of the DNA helicase for the modified RNA by at least 10%, preferably at least 20%, at least 30%, at least 40%, at least 50%, at least 60%, at least 70%, at least 80% or at least 90% Most preferably the modification of the RNA polynucleotide increases the affinity of the DNA helicase by 95% or more. Facilitated DNA helicase binding to the modified RNA is defined as a situation where DNA helicase binds more easily to the modified RNA polynucleotide as compared to non-modified or unmodified RNA polynucleotide. Increased DNA helicase binding to the modified RNA polynucleotide is defined as an amount or level of DNA helicase binding that is greater than, or more than, the amount or level of DNA helicase binding that is observed for non-modified or unmodified RNA polynucleotide i.e., an RNA that has not been modified in accordance with the modification methods of the invention. The level of binding of DNA helicase to a target RNA polynucleotide can be easily tested using routine methods which are known and routine to one of skill in the art.

The target RNA polynucleotide is modified to comprise a non-RNA polynucleotide, such as a polynucleotide region or sequence or construct. At least one nucleotide of the non-RNA polynucleotide is not RNA. The non-RNA polynucleotide may therefore comprise a ribonucleotide or RNA nucleotide but must also comprise or include a non-RNA nucleotide or sequence i.e., a nucleotide or sequence that is not RNA. The target RNA polynucleotide is modified by the addition or attachment of the target RNA to a non-RNA polynucleotide (which may or may not comprise a ribonucleotide or an RNA nucleotide) to form a construct of the invention. The addition or attachment of the non-RNA polynucleotide to the RNA polynucleotide means that the interaction between the DNA helicase and the modified RNA construct is increased i.e., as compared with interaction that occurs between DNA helicase and RNA polynucleotide in un-modified form, without the attached non-RNA polynucleotide. Additionally or alternatively, the addition or attachment of the non-RNA polynucleotide to the RNA polynucleotide means that the specificity of DNA helicase for the modified RNA construct is increased i.e., as compared to the specificity of the DNA helicase for the RNA polynucleotide in un-modified form, without the attached non-RNA polynucleotide. Additionally or alternatively, the addition or attachment of the non-RNA polynucleotide to the RNA polynucleotide means that DNA helicase binding to the modified RNA construct is facilitated and/or DNA helicase binding to the modified RNA construct is increased i.e., as compared with binding that occurs between DNA helicase and RNA polynucleotide in un-modified form, without the attached non-RNA polynucleotide. Additionally or alternatively, the addition or attachment of the non-RNA polynucleotide to the RNA polynucleotide means that the DNA helicase binds more efficiently or more strongly to the modified RNA construct and is less likely to disengage from the modified construct i.e., as compared with binding that occurs between DNA helicase and RNA polynucleotide in un-modified form, without the attached non-RNA polynucleotide.

Preferably the modification of the RNA polynucleotide decreases the unbinding of the DNA helicase from the RNA polynucleotide by at least 10%, preferably at least 20%, at least 30%, at least 40%, at least 50%, at least 60%, at least 70%, at least 80% or at least 90%. Most preferably the modification of the RNA polynucleotide decreases the unbinding of the DNA helicase from the RNA polynucleotide by 95% or more.

Non-RNA Polynucleotide

The target RNA polynucleotide sequence is modified to comprise a non-RNA polynucleotide. The target RNA is attached to a non-RNA polynucleotide. The target RNA is preferably covalently attached to a non-RNA polynucleotide. The non-RNA polynucleotide must comprise at least one nucleotide which is not a ribonucleotide, i.e. which is not from RNA. The non-RNA polynucleotide may additionally comprise a ribonucleotide or RNA but it must also comprise or include at least one non-RNA nucleotide i.e., a nucleotide that is not RNA. Typically the non-RNA polynucleotide which comprises RNA comprises less than 20 RNA nucleotides such as 1, 2, 3, 4, 5, 6, 7, 8, 9, 10, 11, 12, 13, 14, 15, 16, 17, 18, or 19 RNA nucleotides. The non-RNA polynucleotide may therefore be a "hybrid" polynucleotide comprising, for example, RNA and another polynucleotide such as DNA or a DNA analogue. The non-RNA may also include DNA spacers etc. The skilled person will be aware that any of the attachment methods described as suitable for making a modified RNA construct of the invention are equally suitable for making the non-RNA polynucleotide, wherein two or more types of nucleic acid sequence may be combined.

Preferably the non-RNA polynucleotide comprises a leader sequence. The leader sequence preferentially threads into the pore.

Preferably the target RNA polynucleotide is modified by attachment of a non-RNA leader sequence to the RNA. The leader sequence facilitates the characterisation method of the invention. The leader sequence is designed to preferentially thread into the pore and thereby facilitate the movement of polynucleotide through the pore. The leader sequence can also be used to link the target RNA polynucleotide to the one or more anchors as discussed below. The leader sequence may be linked to the target RNA polynucleotide.

The leader sequence typically comprises a polymer region. The polymer region is preferably negatively charged. The polymer is preferably a polynucleotide, such as DNA, a modified polynucleotide (such as abasic DNA), PNA, LNA, polyethylene glycol (PEG) or a polypeptide. The leader sequence preferably comprises a single stranded polynucleotide.

The single stranded leader sequence may comprise a single strand of DNA, iSpC3, a poly dT section or a poly dC section. The leader sequence preferably comprises one or more spacers. The leader sequence is preferably part of a Y adaptor as defined below.

The leader sequence can be any length, but is typically 10 to 200 nucleotides in length. In one embodiment of the invention the non-RNA leader sequence comprises iSpC3. Most preferably the non-RNA leader sequence is an iSpC3 or repeating sequences of C and A (e.g., 4× (9C's and 1A)) of approx 40 nucleotides in length. The length of the leader typically depends on the transmembrane pore used in the method.

Preferably the non-RNA polynucleotide comprises a region to which a DNA helicase is capable of binding (a DNA helicase binding site) or a DNA adaptor. The target RNA polynucleotide may be modified to comprise a DNA binding site for the DNA helicase which controls movement of the target RNA through a transmembrane pore. As used herein the terms "DNA helicase binding site" includes a DNA or DNA analogue sequence of sufficient size/length to allow one or more DNA helicases to bind thereto. The length of the binding site depends on the number of helicases that should bind thereto. The region to which a DNA helicase is capable of binding is preferably a polynucleotide such as DNA, a modified polynucleotide (such as abasic DNA), PNA, LNA, polyethylene glycol (PEG). Preferably the DNA helicase binding site is a single stranded, non hybridised region. The region may correspond to the leader sequence. Alternatively, the region may be distinct from the leader sequence. The DNA helicase may help to control the movement of the RNA polynucleotide through the pore as discussed in more detail below.

Preferably the non-RNA polynucleotide is further provided with a blocking site or blocking molecule, which may be located adjacent or in close proximity to the DNA binding site, at the end opposite to that which the one or more helicases are to be moved. The blocking molecule prevents backward movement of the helicase and prevents it slipping off the construct.

The non-RNA polynucleotide construct for attachment to the target RNA sequence preferably comprises: portion (i) a polymer of 5 or more charged units which preferably provides for capture of the target polynucleotide by a pore; and/or portion (ii) a blocking-strand hybridisation site of approximately 20 nucleotides in length which; and/or portion (iii) a DNA-helicase binding site of 1 or more non-RNA nucleotides, e.g., 1, 2, 3, 4, 5, 6, 7, 8, 9, 10, 11, 12, 13, 14, 15, 16, 17, 18, 19, 20, 30, 40, or 50 non-RNA nucleotides; and/or portion (iv) a stalling chemistry of 1 or more units e.g., 1, 2, 3, 4, 5, 6, 7, 8, 9, 10 or more units, such as Sp18, as described in WO2014/135838 which is incorporated by reference herein; and/or portion (v) a tether hybridisation site of approximately 30 nucleotides in length; and/or portion (vi) a sequence that facilitates ligation of the non-RNA polynucleotide to the RNA polynucleotide. The total length of the non-RNA polynucleotide for attachment to a target RNA sequence may therefore comprise approximately 50 to 200 nucleotides.

For example, in one embodiment, a non-RNA polynucleotide may comprise at least one of: (i) a polymer of 5 or more charged units; (ii) a blocking-strand hybridisation site of approximately 20 nucleotides in length; (iii) a DNA-helicase binding site of 1 or more non-RNA nucleotides. e.g., 1, 2, 3, 4, 5, 6, 7, 8, 9, 10, 11, 12, 13, 14, 15, 16, 17, 18, 19, 20, 30, 40, or 50 nucleotides; (iv) a stalling chemistry of 1 or more units e.g., 1, 2, 3, 4, 5, 6, 7, 8, 9, 10 or more units, such as Sp18, as described in WO2014/135838 which is incorporated by reference herein; (v) a tether hybridisation site of approximately 30 nucleotides in length; and/or (vi) a sequence that facilitates ligation of the non-RNA polynucleotide to the RNA polynucleotide, as described in the preceding sections.

Each of (i) to (vi) is discussed in more detail below:

Portion (i)

Portion (i) of the non-RNA polynucleotide is preferably a polymer with net negative charge. The polymer may be any of those discussed above for the leader sequence. Preferably the polymer lacks nucleobases or lacks nucleosides. The polymer may be any of the spacers discussed below. Representative examples of sequences that meet these criteria are:

```
                                          (SEQ ID NO: 16)
TTTTTTTTTTTTTTTTTTTTTTTTTTTTTTTTTTTTTTTT (SEQ ID NO: 46)
CCCCCCCCCACCCCCCCCCACCCCCCCCCACCCCCCCCCA

6666666666666666666666666666666666666666

7777777777777777777777777777777777777777

8888888888888888888888888888888888888888
``` where 6=1,2-dedeoxy nucleotide monophosphate
where 7=n-propylene phosphate (Spacer 3 groups)
where 8=PEG3 phosphate (Spacer 9 groups)

Portion (ii)

Portion (ii) of the non-RNA polynucleotide is any polynucleotide sequence which allows hybridisation of a blocking strand and can include DNA or RNA or analogues like PNA, GNA, TNA, BNA, LNA or morpholino. Representative examples of sequences that meet these criteria are:

```
                              (SEQ ID NO: 47)
        ACTCGCAGATCATTACGATC (SEQ ID NO: 48)
        rArCrUrCrGrCrArGrArUrCrArUrUrArCrGArUrC
```

PNA with the sequence of SEQ ID NO: 47
BNA with the sequence of SEQ ID NO: 47

```
                              (SEQ ID NO: 49)
        CGATTGACTAAGCTATACGC (SEQ ID NO: 50)
        rCrGrArUrUrGrArCrUrArArGrCrUrArUrArCrGrC
```

PNA with the sequence of SEQ ID NO: 49
BNA with the sequence of SEQ ID NO: 49

Portion (iii)

Portion (iii) of the non-RNA polynucleotide should be of sufficient length to allow binding of the specific DNA helicase of use and should be composed of non-RNA nucleotides including analogues such as PNA, GNA, TNA, BNA, LNA or morpholino. In a preferred embodiment of the invention, portion (iii) is DNA. Representative examples of sequences that meet these criteria are:

```
                                        (SEQ ID NO: 51)
TTTTTTTTTT (SEQ ID NO: 52)
TTTTTTTTTTTTTTTTTTTT (SEQ ID NO: 31)
CCCCCCCCCA (SEQ ID NO: 53)
CCCCCCCCCACCCCCCCCCA

XXXXXXXXX
(where X is independently selected from A,
T, G or C).
```

Portion (iv)

Portion (iv) of the non-RNA polynucleotide should prevent or slow ATP-mediated translocation of the DNA helicase without the force of the pore. Representative examples of sequences that meet these criteria are:

```
                                        (SEQ ID NO: 54)
rArArArArArArArArArA (SEQ ID NO: 55)
rUrCrCrArUrArCrGrArA

9999
``` where 9=PEG6 phosphate (Spacer 9 (iSp9) groups)

Portion (v)

Portion (v) of the non-RNA polynucleotide should allow hybridisation of a tethering oligo with a TM high enough to form a stable hybrid. Representative examples of sequences that meet these criteria are:

```
                                        (SEQ ID NO: 56)
AACTACTAGGATCATCGATGTATCTGCTCA (SEQ ID NO: 57)
AGCTTAACATACGATACTCTTAGCTAACCA (SEQ ID NO: 58)
rArArCrUrArCrUrArGrGrArUrCrArUrCrGrArUrGrUrArU rCrUrGrCrUrCrA (SEQ ID NO: 59)
rArGrCrUrUrArArCrArUrArCrGrArUrArCrUrCrUrUrArG rCrUrArArCrCrA
```

PNA with the sequence of SEQ ID NO: 56
PNA with the sequence of SEQ ID NO: 57

Portion (vi)

Portion (vi) of the non-RNA polynucleotide should facilitate ligation of the non-RNA polynucleotide to the RNA polynucleotide. Representative examples of sequences that meet these criteria are:

```
                                        (SEQ ID NO: 60)
ACTCTGAACC (SEQ ID NO: 61)
ACTCTrGrArArCrC (SEQ ID NO: 62)
GCACAATGAT (SEQ ID NO: 63)
GCACArArTrGrArT
```

Any combination of (i) to (vi) may be made in accordance with the invention: Preferably the non-RNA polynucleotide comprises (iii) and (vi) in combination with {i}, {ii}, {iv}, {v}, {i,ii}, {i,iv}, {i,v}, {ii,iv}, {ii,v}, {iv,v}, {i,ii,iv}, {i,ii,v}, {i,iv,v}, {ii,iv,v}, {i,ii,iv,v}.

Any of the different representative examples given above for each of portions (i) to (vi) can be used interchangeably to form a non-RNA polynucleotide for attachment to a target RNA sequence.

Seven different representative example of a non-RNA polynucleotide are as follows:

```
Construct 1:
(40x SpC3)(ACTCGCAGATCATTACGATC)(10x dT)(4x Sp18)
(AACTACTAGGATCATCGATGTATCTGCTCA)(ACTCTGAACC)
i.e.,
(40x SpC3)(SEQ ID NO: 47)(SEQ ID NO: 51)(4x Sp18)
(SEQ ID NO: 56)(SEQ ID NO: 60)

Construct 2:
(40x SpC3)(ACTCGCAGATCATTACGATC)(20x dT)(4x Sp18)
(AACTACTAGGATCATCGATGTATCTGCTCA)(ACTCTGAACC)
i.e.,
(40x SpC3)(SEQ ID NO: 47)(SEQ ID NO: 52)(4x Sp18)
(SEQ ID NO: 56)(SEQ ID NO: 60)

Construct 3:
(40x rU)(ACTCGCAGATCATTACGATC)(10x dT(4x Sp18)
(AACTACTAGGATCATCGATGTATCTGCTCA)(ACTCTGAACC)
i.e.,
(40x rU)(SEQ ID NO: 47)(SEQ ID NO: 51)(4x Sp18)
(SEQ ID NO: 56)(SEQ ID NO: 60)

Construct 4:
(40x SpC3)(ACTCGCAGATCATTACGATC)(10x dT)(4x Sp18)
(AACTACTAGGATCATCGATGTATCTGCTCA)(ACTCTrGrArArCrC)
i.e.,
(40x SpC3)(SEQ ID NO: 47)(SEQ ID NO: 51)(4x Sp18)
(SEQ ID NO: 56)(SEQ ID NO: 61)

Construct 5:
(40x SpC3)(ACTCGCAGATCATTACGATC)(10x dT)
(rArArArCrUrArCrGrCrU)(AACTACTAGGATCATCGATGTATCT
GCTCA)(ACTCTGAACC)
i.e.,
(40x SpC3)(SEQ ID NO: 47)(SEQ ID NO: 51)
(SEQ ID NO: 64)(SEQ ID NO: 56)(SEQ ID NO: 60)

Construct 6:
(40x SpC3)(ACTCGCAGATCATTACGATC)(10x dT)(4x Sp18)
(AGCTTAACATACGATACTCTTAGCTAACCA)(ACTCTGAACC)
i.e.,
(40x SpC3)(SEQ ID NO: 47)(SEQ ID NO: 51)(4x Sp18)
(SEQ ID NO: 57)(SEQ ID NO: 60)
```

```
Construct 7:
(40x SpC3)(PNA with the sequence of SEQ ID NO: 47)

(10x dT)(4x Sp18)(AACTACTAGGATCATCGATGTATCTGCTCA)

(ACTCTGAACC)
i..e,
(40x SpC3)(PNA with the sequence of SEQ ID NO: 47)
(SEQ ID NO: 51)(4x Sp18)(SEQ ID NO: 56)
(SEQ ID NO: 60)
```

Attachment

The target RNA polynucleotide is attached to a non-RNA polynucleotide and/or the non-RNA polynucleotide is attached to the target RNA polynucleotide to form a modified RNA polynucleotide. Where the non-RNA polynucleotide comprises an ribonucleotide or an RNA sequence, the non-RNA polynucleotide may be attached to the target RNA polynucleotide via the ribonucleotide or RNA sequence which is comprised within the non-RNA polynucleotide.

The method comprises in step (a) providing the modified RNA polynucleotide and a DNA helicase enzyme. The method may further comprise, before step (a), attaching the RNA polynucleotide to the non-RNA polynucleotide and/or attaching the non-RNA polynucleotide to the RNA polynucleotide to form a modified RNA polynucleotide.

The target RNA polynucleotide and the non-RNA polynucleotide (which may be DNA or a DNA analogue) can be attached to each other in any manner using any method or methods known in the art. Preferably the target RNA polynucleotide and the non-RNA polynucleotide are attached using one or more of the various methods described below. The target RNA polynucleotide may be chemically attached to the non-RNA polynucleotide, for example by a covalent bond. The target RNA polynucleotide may be attached to the non-RNA polynucleotide by chemical or enzymatic ligation. The target RNA polynucleotide may be attached to the non-RNA polynucleotide by hybridisation and/or synthetic methods. The RNA polynucleotide may be attached to the non-RNA polynucleotide using a topoisomerase. The RNA polynucleotide may be attached to the non-RNA polynucleotide at more than one, such as two or three, points. The method of attachment may involve one, two, three, four, five or more different methods of attachment. Any combination of the attachment methods described below may be used in accordance with the invention.

The RNA polynucleotide and non-RNA polynucleotide (which may or may not comprise a ribonucleotide or RNA) may be produced separately and then attached together. The two components may be attached in any configuration. For instance, they may be attached via their terminal (i.e. 5' or 3') ends. Suitable configurations include, but are not limited to, the 5' end of the RNA polynucleotide being attached to the 3' end of the non-RNA polynucleotide and vice versa. Alternatively, the two components may be attached via nucleotides within their sequences.

Polynucleotides may be attached via their naturally occurring nucleotides. Naturally occurring nucleotides may be modified to facilitate attachment. For instance, the naturally occurring nucleic acids may be modified by, for example, Trimethyl guanosine synthase for the mRNA cap. Other suitable modifications are known in the art. Modifications may be introduced by substitution. The RNA polynucleotide may be attached to the non-RNA polynucleotide via a linker molecule. The RNA polynucleotide may be attached to the non-RNA polynucleotide using one or more, such as two or three, linkers. Linkers can comprise any molecule that stretches across the distance required. Linkers can vary in length from one carbon (phosgene-type linkers) to many Angstroms. Examples of linear molecules that are suitable for use as linkers, include but are not limited to, are polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, polyamides. These linkers may be inert or reactive, in particular they may be chemically cleavable at a defined position, or may be themselves modified with a fluorophore or ligand. The linker is preferably resistant to dithiothreitol (DTT). Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$, $(SG)_8$, $(SG)_{10}$, $(SG)_{15}$ or $(SG)_{20}$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The RNA polynucleotide may be attached to the non-RNA polynucleotide using one or more chemical crosslinkers or one or more peptide linkers. Suitable chemical crosslinkers are well-known in the art. Suitable chemical crosslinkers include, but are not limited to, those including the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide), phosgene type reagents, sulphonyl chloride reagents, isothiocyanates, acyl halides, hydrazines, disulphides, vinyl sulfones, aziridines and photoreactive reagents (such as aryl azides, diaziridines).

Reactions between the RNA polynucleotide and non-RNA polynucleotide may be spontaneous, such as cysteine/maleimide, or may require external reagents, such as Cu(I) for linking azide and linear alkynes.

Preferred crosslinkers include 2,5-dioxopyrrolidin-1-yl 3-(pyridin-2-yldisulfanyl)propanoate, 2,5-dioxopyrrolidin-1-yl 4-(pyridin-2-yldisulfanyl)butanoate, 2,5-dioxopyrrolidin-1-yl 8-(pyridin-2-yldisulfanyl)octananoate, di-maleimide PEG 1 k, di-maleimide PEG 3.4 k, di-maleimide PEG 5 k, di-maleimide PEG 10 k, bis(maleimido)ethane (BMOE), bis-maleimidohexane (BMH), 1,4-bis-maleimidobutane (BMB), 1,4 bis-maleimidyl-2,3-dihydroxybutane (BMDB), BM[PEO]2 (1,8-bis-maleimidodiethyleneglycol), BM[PEO]3 (1,11-bis-maleimidotriethylene glycol), tris[2-maleimidoethyl]amine (TMEA), DTME dithiobismaleimidoethane, bis-maleimide PEG3, bis-maleimide PEG11, DBCO-maleimide, DBCO-PEG4-maleimide, DBCO-PEG4-NH2, DBCO-PEG4-NHS, DBCO-NHS, DBCO-PEG-DBCO 2.8 kDa, DBCO-PEG-DBCO 4.0 kDa, DBCO-15 atoms-DBCO, DBCO-26 atoms-DBCO, DBCO-35 atoms-DBCO, DBCO-PEG4-S-S-PEG3-biotin, DBCO-S-S-PEG3-biotin and DBCO-S-S-PEG11-biotin. The most preferred crosslinkers are succinimidyl 3-(2-pyridyldithio)propionate (SPDP) and maleimide-PEG(2 kDa)-maleimide (alpha,omega-bis-maleimido poly(ethylene glycol)).

The linkers may be labeled. Suitable labels include, but are not limited to, fluorescent molecules (such as Cy®3 or AlexaFluor®555), radioisotopes, e.g. $^{125}I$, $^{35}S$, enzymes, antibodies, antigens, polynucleotides and ligands such as biotin. Such labels allow the amount of linker to be quantified. The label could also be a cleavable purification tag, such as biotin, or a specific sequence to show up in an identification method.

Cross-linkage of RNA polynucleotide or non-RNA polynucleotide to themselves may be prevented by keeping the concentration of linker in a vast excess of the RNA polynucleotide and/or non-RNA polynucleotide. Alternatively, a "lock and key" arrangement may be used in which two linkers are used. Only one end of each linker may react together to form a longer linker and the other ends of the linker each react with a different part of the construct (i.e. RNA polynucleotide or non-RNA polynucleotide).

The attachment of the RNA polynucleotide to the non-RNA polynucleotide may be permanent or stable (i.e. the RNA polynucleotide does not become detached from the non-RNA polynucleotide in the method of the invention). A preferred permanent or stable attachment is covalent attachment.

Alternatively the attachment is transient, i.e. the RNA polynucleotide may detach from the non-RNA polynucleotide. It will be understood by one of skill in the art that any of the methods described herein are equally suitable for attaching a non-RNA polynucleotide to a target RNA and also in constructing the non-RNA polynucleotide itself which may, as described above, be a hybrid of two or more types of nucleic acid e.g., DNA and RNA.

Click Chemistry

The target RNA polynucleotide can be covalently attached to the non-RNA polynucleotide. The non-RNA polynucleotide may or may not comprise a pre-bound DNA helicase enzyme. In a preferred embodiment, the covalent bond between the RNA polynucleotide and non-RNA polynucleotide, e.g., a DNA leader sequence, can be made using copper free click chemistry or copper catalysed click chemistry. Click chemistry has been used in these applications because of its desirable properties and its scope for creating covalent links between diverse building blocks. For example, it is fast, clean and not poisonous, generating only inoffensive byproducts. Click chemistry is a term first introduced by Kolb et al. in 2001 to describe an expanding set of powerful, selective, and modular building blocks that work reliably in both small- and large-scale applications (Kolb H C, Finn, M G, Sharpless K B, Click chemistry: diverse chemical function from a few good reactions, Angew. Chem. Int. Ed. 40 (2001) 2004-2021). They have defined the set of stringent criteria for click chemistry as follows: "The reaction must be modular, wide in scope, give very high yields, generate only inoffensive byproducts that can be removed by nonchromatographic methods, and be stereospecific (but not necessarily enantioselective). The required process characteristics include simple reaction conditions (ideally, the process should be insensitive to oxygen and water), readily available starting materials and reagents, the use of no solvent or a solvent that is benign (such as water) or easily removed, and simple product isolation. Purification if required must be by nonchromatographic methods, such as crystallization or distillation, and the product must be stable under physiological conditions".

Suitable examples of click chemistry include, but are not limited to, the following:

(a) copper-free variant of the 1,3 dipolar cycloaddition reaction, where an azide reacts with an alkyne under strain, for example in a cyclooctane ring;
(b) the reaction of an oxygen nucleophile on one linker with an epoxide or aziridine reactive moiety on the other; and
(c) the Staudinger ligation, where the alkyne moiety can be replaced by an aryl phosphine, resulting in a specific reaction with the azide to give an amide bond.

Preferably the click chemistry reaction is the Cu (I) catalysed 1,3 dipolar cycloaddition reaction between an alkyne and an azide. In a preferred embodiment, the first group is an azide group and the second group is an alkyne group. Nucleic acid bases have already been synthesized incorporating azide and alkyne groups in preferred positions (for example Kocalka P, El-Sagheer A H, Brown T, Rapid and efficient DNA strand cross-linking by click chemistry, Chembiochem. 2008. 9(8):1280-5). Alkyne groups are available commercially from Berry Associates (Michigan, USA) and azide groups are synthesized by ATDBio or IDT bio.

If nucleotides within the linkers' nucleic acid acid regions are modified to include groups that can form covalent bonds, the modified nucleotides are preferably offset from one another by one nucleotide in order to achieve the link. This follows the published work of Tom Brown (Kocalka et al. (2008) ChemBiochem 9 8 1280-1285).

A click-reactive base may be added to the target RNA polynucleotide when the RNA transcript is formed. Alternatively a click group may be added to a target RNA polynucleotide by hypermethylase enzyme (for capped mRNA).

Preferably the reactive groups are azide and hexynl groups such as 3AzideN and 5'-hexynl-G. Preferably the azide group is attached to the non-RNA polynucleotide which is preferably DNA (and may or may not comprise a ribonucleotide or RNA sequence) and the hexynl group is attached to the target RNA polynucleotide.

Examples 3 and 5 illustrate the use of a click reaction to join a non-RNA polynucleotide (comprising for example DNA) to a target RNA polynucleotide. Example 5 further describes the use of a bridging moiety to obtain a 2 dimensional (2D) RNA-cDNA construct. The construct of Example 5 which is illustrated in FIG. 15 can be compared to the construct of Example 3 (1D construct illustrated in FIG. 10) which does not comprise a bridging moiety.

Ligation

The target RNA polynucleotide may be ligated to the non-RNA polynucleotide (which RNA polynucleotide may or may not comprise a ribonucleotide or RNA sequence). Ligation is the joining of two nucleic acid fragments most commonly through the action of an enzyme or by chemical means. The ends of RNA and DNA fragments are joined together by the formation of phosphodiester bonds between the 3'-hydroxyl of one RNA or DNA terminus with the 5'-phosphoryl of another. A co-factor is generally involved in the reaction, and this is usually ATP or $NAD^+$. A splint of RNA or non-RNA polynucleotide, such as a DNA, PNA, glycerol nucleic acid (GNA), threose nucleic acid (TNA) or locked nucleic acid (LNA) may be used in the ligation reaction to facilitate ligation by holding the RNA polynucleotide and the non-RNA polynucleotide adjacent to each other by hybridisation to the splint. The non-RNA polynucleotide to be attached to the RNA polynucleotide may or may not comprise a pre-bound DNA helicase enzyme.

The non-RNA polynucleotide may be ligated to either end of the RNA polynucleotide, i.e. the 5' or the 3' end. The non-RNA polynucleotide may be ligated to both ends of the target RNA polynucleotide. Preferably the non-RNA polynucleotide is ligated to the 5' end of the target RNA polynucleotide. The non-RNA polynucleotide may be ligated to the RNA polynucleotide using any method known in the art. The one or more non-RNA polynucleotide may be ligated using a ligase, such as T4 DNA ligase, *E. coli* DNA ligase, Taq DNA ligase, Tma DNA ligase, 9° N DNA ligase, T4 Polymerase I, T4 Polymerase 2, Thermostable 5' App DNA/RNA ligase. SplintR, circ Ligase, T4 RNA ligase 1 or T4 RNA ligase 2. The one or more non-RNA polynucleotides may be ligated to the RNA polynucleotide (or vice versa) in the absence of ATP or using gamma-S-ATP (ATPγS) instead of ATP.

The method preferably further comprises removing the ligase from the method conditions.

Example 2 illustrates the ligation of RNA polynucleotide to DNA using T4 DNA ligase.

Synthetic Methods

An oligonucleotide or primer can be used to hybridise to any region of the target RNA polynucleotide and act as a starting point for DNA synthesis. The oligonucleotide or primer may or may not comprise a pre-bound DNA helicase enzyme.

Eukaryotic RNA typically comprises polyA tail, i.e. a stretch of consecutive adenosine monophosphates. The polyA tail is typically at the 3' end of the RNA. The Poly A Polymerase or Terminal Transferase enzyme can be utilised to add a poly(dA) tail onto the 3' end of a prokaryotic RNA strand if necessary. A primer can be hybridised to the polyA tail of the target RNA and used as a starting point for synthesis. The primer preferably comprises a polyT region, i.e. a region containing only nucleotides based on thymine, or a polyU region, i.e. a region containing only nucleotides based on uracil. The polyU region may contain UMP or dUMP. The polyU region may be any length, such as at least 10, at least 15, at least 20, at least 25 or more.

In one embodiment of the invention the non-RNA polynucleotide comprises a DNA primer with a leader sequence which is hybridised to an RNA strand at the poly(dA) region. One or more DNA helicase enzymes may be pre-bound to the DNA primer that is to be hybridised to the RNA strand. Alternatively the DNA primer that is to be hybridised to the RNA does not contain or comprise pre-bound DNA helicase enzyme. Reverse transcription of the RNA strand from the DNA primer is allowed to occur and a bridging moiety such as a DNA hairpin can then be ligated to the double-stranded DNA/RNA. Such a bridging moiety, for example a hairpin loop adaptor, can be added to any double-stranded target RNA polynucleotide (RNA/RNA or RNA/DNA) or modified construct of the invention. A bridging moiety permits contiguous sequencing of both template and complement strands by connection into a single strand. Preferably an adaptor (e.g., a Y adaptor) containing a leader sequence is attached to one end of the RNA and a bridging moiety adaptor is attached to the other end. The leader sequence preferentially threads into the nanopore and the bridging moiety connecting the two strands (which may be RNA/RNA or RNA/DNA) allows both strands to be characterised as the polynucleotide unzips and both strands (connected via the bridging moiety) move through the pore. This is advantageous because it doubles the amount of information obtained from a double-stranded polynucleotide. Moreover, because the sequences in the two strands are complementary, the information from the two strands can be combined informatically. This mechanism provides a proof-reading capability that provides higher confidence observations.

Alternatively the bridging moiety can be added to a target RNA polynucleotide prior to synthesis of the complement and used as a primer for complement synthesis, as discussed in more detail below.

In one embodiment of the invention, the strands of a double stranded RNA polynucleotide or an RNA/DNA duplex (e.g., RNA and cDNA) are linked using a bridging moiety. The method of characterising a target RNA polynucleotide according to the invention then preferably comprises contacting (i) the linked construct comprising the target RNA polynucleotide, wherein the RNA polynucleotide is modified to comprise a non-RNA polynucleotide, and (ii) a DNA helicase enzyme with a transmembrane pore such that the target RNA moves through the pore. The method preferably comprises taking one or more measurements as the target RNA moves with respect to the pore wherein the measurements are indicative of one or more characteristics of the complementary polynucleotide (RNA or cDNA) and the target RNA and thereby characterising the target double stranded polynucleotide.

Linking and interrogating both strands of a target dsRNA or RNA/DNA duplex in this way increases the efficiency and accuracy of characterization.

The bridging moiety is capable of linking the two strands of a target dsRNA polynucleotide or RNA/DNA duplex. The bridging moiety typically covalently links the two strands of a target dsRNA polynucleotide or RNA/DNA duplex. The bridging moiety can be anything that is capable of linking the two strands of a target dsRNA polynucleotide or RNA/DNA duplex, provided that the bridging moiety does not interfere with movement of the RNA polynucleotide through the transmembrane pore.

The bridging moiety may be linked to the target polynucleotide by any suitable means known in the art. The bridging moiety may be synthesized separately and chemically attached or enzymatically ligated to the RNA target polynucleotide. Alternatively, the bridging moiety may be generated in the processing of the target polynucleotide.

The bridging moiety is linked to the target polynucleotide at or near one end of the target polynucleotide. The bridging moiety is preferably linked to the target polynucleotide within 10 nucleotides of the end of the target polynucleotide Suitable bridging moieties include, but are not limited to a polymeric linker, a chemical linker, a polynucleotide or a polypeptide. Preferably, the bridging moiety comprises DNA, RNA, modified DNA (such as abasic DNA), RNA, PNA, LNA or PEG. The bridging moiety is more preferably DNA or RNA.

The bridging moiety is most preferably a hairpin loop or a hairpin loop adaptor. Suitable hairpin adaptors can be designed using methods known in the art. The hairpin loop may be any length. The hairpin loop is typically 110 or fewer nucleotides, such as 100) or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding.

The hairpin adaptor may be ligated to either end of the target polynucleotide, i.e. the 5' or the 3' end. The hairpin adaptor may be ligated using any method known in the art. The hairpin adaptor may be ligated using a ligase, such as T4 DNA ligase, E coli DNA ligase, Taq DNA ligase, Tma DNA ligase and 9° N DNA ligase.

The complementary polynucleotide (RNA or cDNA) and the target RNA may be separated after or before the linked construct is contacted with the pore in accordance with the invention. They may be separated as the polynucleotide movement through the pore is controlled by a polynucleotide binding protein, such as a helicase, or molecular brake.

The complementary polynucleotide (RNA or cDNA) and the target RNA may be separated using any method known in the art. For instance, they may be separated by a polynucleotide binding protein or using conditions which favour dehybridsation (examples of conditions which favour dehybridisation include, but are not limited to, high temperature, high pH and the addition of agents that can disrupt hydrogen bonding or base pairing, such as formamide and urea).

The hairpin adaptor preferably comprises a selectable binding moiety. This allows the linked construct to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologus sequences. Alternatively, selectable polynucleotide sequences specifically bind to a surface coated with polynucleotide binding proteins.

The hairpin adaptor and/or the selectable binding moiety may comprise a region that can be cut, nicked, cleaved or hydrolysed. Such a region can be designed to allow the complementary polynucleotide and/or target RNA to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

The linked construct preferably comprises a leader sequence at the opposite end from the bridging moiety, such as a hairpin loop or hairpin loop adaptor.

In one embodiment of the invention, a bridging moiety such as a hairpin-forming oligonucleotide is attached to the target RNA strand. Prior to the attachment of the bridging moiety, the target RNA strand may have been modified to comprise a non-RNA polynucleotide. For example the target RNA strand may have been attached to a non-RNA polynucleotide using chemical attachment, for example by a covalent bond, click chemistry, chemical or enzymatic ligation, by hybridisation and/or synthetic methods. The RNA polynucleotide may have been attached to the non-RNA polynucleotide using a topoisomerase. Alternatively the bridging moiety may be attached to the target RNA strand prior to the modification of the RNA strand to comprise a non-RNA polynucleotide. Similarly, the bridging moiety, such as a hairpin-forming oligonucleotide, may be attached to the target RNA strand by any of the attachment methods described herein. Preferably the bridging moiety is attached to the target RNA strand by ligation. Any suitable ligase described above may be used for the ligation of the bridging moiety to the target RNA strand e.g., T4 DNA ligase, E. coli DNA ligase, Taq DNA ligase, Tma DNA ligase, 9° N DNA ligase, T4 Polymerase I, T4 Polymerase 2, Thermostable 5' App DNA/RNA ligase, SplintR, circ Ligase, T4 RNA ligase 1 or T4 RNA ligase 2.

Preferably the bridging moiety is attached to the 3' or 5'end of the target RNA strand, most preferably the bridging moiety is attached to the the 3' end of the target RNA strand. Reverse transcription from the bridging moiety, such as a hairpin-forming oligonucleotide, results in the formation of a RNA-cDNA construct that is joined by a hairpin. In this embodiment the bridging moiety acts as a primer for reverse transcription: The bridging moiety, such as hairpin forming oligonucleotide, is itself used as a primer for reverse-transcription to generate an RNA-cDNA construct and enable a 2D read. Preferably reverse transcription is initiated at the 3' end of the bridging moiety. A poly-T overhang on the bridging moiety hybridizes to the poly A-tail of the RNA. The polyA-tail of the RNA is typically from 50 to 300 nucleotides in length. Preferably the poly-T overhang of the bridging moiety comprises less than 100 nucleotides, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 90, 91, 92, 93, 94, 95, 96, 97, 98, or 99 nucleotides. Preferably the poly T overhang is on the 3' end of the bridging moiety. In this embodiment of the invention, where a bridging moiety is attached to a target RNA, (which target RNA has already been or is yet to be modified to comprise a non-RNA polynucleotide; preferably a DNA polynucleotide) and wherein the bridging moiety serves as a primer for reverse transcription, a DNA/RNA/cDNA construct is created (see Example 5 and FIG. 15). This construct allows for a 2D read wherein both the target RNA and its complementary DNA sequence (formed by reverse transcription) can be sequenced by the transmembrane pore due to the presence of the bridging moiety. This method is advantageous because it doubles the amount of information obtained from a single double stranded target polynucleotide construct. Moreover, because the sequence in the complementary (cDNA) strand is necessarily orthogonal to the sequence of the template RNA strand, the information from the two strands can be combined informatically. Thus, this mechanism provides an orthogonal proof-reading capability that provides higher confidence observations.

Furthermore, the other major advantages of the method of the invention are:

1) Coverage of missed nucleotides: the method substantially minimises issues of any missed nucleotides or groups of nucleotides (e.g. due to movement issues such as the RNA strand slipping through the pore), since any states that might be missed in one strand are likely to be covered by the orthogonal information obtained from its complement region.

2) Coverage of problematic sequence motifs: any difficult to sequence motifs are covered by the orthogonal and opposite information in the complementary strand, which having a different sequence will not have the same sequence dependent issues. For example, this is particularly relevant for sequence motifs that produce only small changes in current, or have similar current levels—i.e. consecutive base motifs that when moved through the nanopore produce the same current block, and are therefore not observed as there is no step change in current. Any similar current levels from one sequence motif will be covered by the entirely different current levels obtained from its orthogonal sequence in the complement strand.

In addition to the advantages discussed above there are a number of special cases where the concept of reading both strands of the double stranded polynucleotide can be utilized to provide further benefits:

1. Epigenetic Information

Being able to identify epigenetic information (such as 5-methylcytosine or 5-hydroxymenthylcytosine nucleotides) or damaged bases within a natural RNA strand is desirable in a wide range of applications. Using the method of the present invention this information is obtained without chemical treatment or amplification, both of which can introduce errors. During nanopore sequencing, changes in current levels are measured as nucleotides pass through the nanopore. The current level is dictated by several bases rather than by a single nucleotide. When a modified nucleotide passes through the nanopore it affects several consecutive levels: This increases the confidence we can have in its detection (See FIG. 18).

Nanopore sequencing is also a single molecule sequencing technology and therefore can be performed without the need for amplification. It has been shown that nanopores can detect modifications to the standard four RNA nucleotides. Reading both strands of the polynucleotide can be useful in detecting RNA modifications in situations where a modified base behaves in a similar way (generates a similar current signal) to another base. For example if methylcytosine (mC) behaves in a similar way to uracil there is an error associated with assigning a mC to a U. In the template strand, there is a probability of the base being called a mC or a U. However, in the complement strand, the corresponding base may appear as a G with a high probability. Thus by "proof reading" the complement strand, it is highly likely that the base in the template strand was a mC rather than a U.

Reading the template and the complement strand can be performed without the need of amplification or replication. However, amplification or replication may be added as part of the sample preparation to aid the detection of epigenetic information.

The linked strands comprising the target RNA polynucleotide can be separated and duplicated at any stage before sequencing is carried out and as many times as necessary. For example, after separating the two linked strands of a first RNA/cDNA polynucleotide construct as described above, a complementary strand to the resulting single stranded polynucleotide can be generated to form another double stranded polynucleotide. The two strands of this double stranded polynucleotide can then be linked using a bridging moiety to form a second construct. This may be referred to herein as the "DUO" method. This construct may then be used in the invention. In such an embodiment, one strand of the double stranded polynucleotide in the resulting construct contains both strands of the original target double stranded polynucleotide (in the first construct) linked by a bridging moiety. The sequence of the original target double stranded polynucleotide or the complement strand can be estimated or determined. This process of replication can be repeated as many times as necessary and provides additional proofreading as the target polynucleotide is in effect being read multiple times.

A nucleotide strand may be constructed where the following information is read through the nanopore in the following order: template RNA (original), complement cDNA (original),—bridging moiety—, template RNA (complement), complement cDNA (complement)

In this scheme, information on the methylated base will be obtained four times. If the epigenetic base is in the original template strand (in this case, mC), the following information will be obtained with a high probability: template (original)-mC, complement (original)-G, template (complement)-C, and complement (complement)-G. It is clear that the original template read and the replicated template read will give different results, while the both complementary reads will yield the same base call. This information can be used to indicate the position of the epigenetic base in the original template strand.

2. Homopolymer Reads

Homopolymer reads may be a problem for single molecule nanopore sequencing. If the homopolymer region is longer than the reading section of the pore, the length of the homopolymer section will be difficult to determine.

To overcome the problem of homopolymer reads, the cDNA strand can be synthesised with the addition of a different/modified base in combination with the original dTTP, dGTP, dATP, dCTP. This could be a natural base analogue such as inosine (I). The base will have a random chance of incorporating compared to the correct natural base and the insertion rates can be controlled by varying the concentration of the triphosphate species.

Through the addition of the alternative base, there will be a probability of an alternative base being inserted into the reverse complement of a homopolymer region. The result of this is that the homopolymer run will be reduced in length to a point where it can be read by the reading section of the nanopore. For example, a homopolymer group of AAAAAAAAAAAA (SEQ ID NO: 33) will have random insertions of the alternative base and may give TTTIT-TIITTTI (SEQ ID NO: 34) (where I is inosine).

The homopolymer stretch is reduced to allow individual nucleotides or groups of nucleotides to be estimated or determined. The template strand will be a natural RNA strand, while the complementary/cDNA strand will contain a mixture of natural bases and base analogues. The combination of data from the template and the complementary reads can be used to estimate the length of the homopolymer run in the original RNA section.

Topoisomerases

Figure 6:
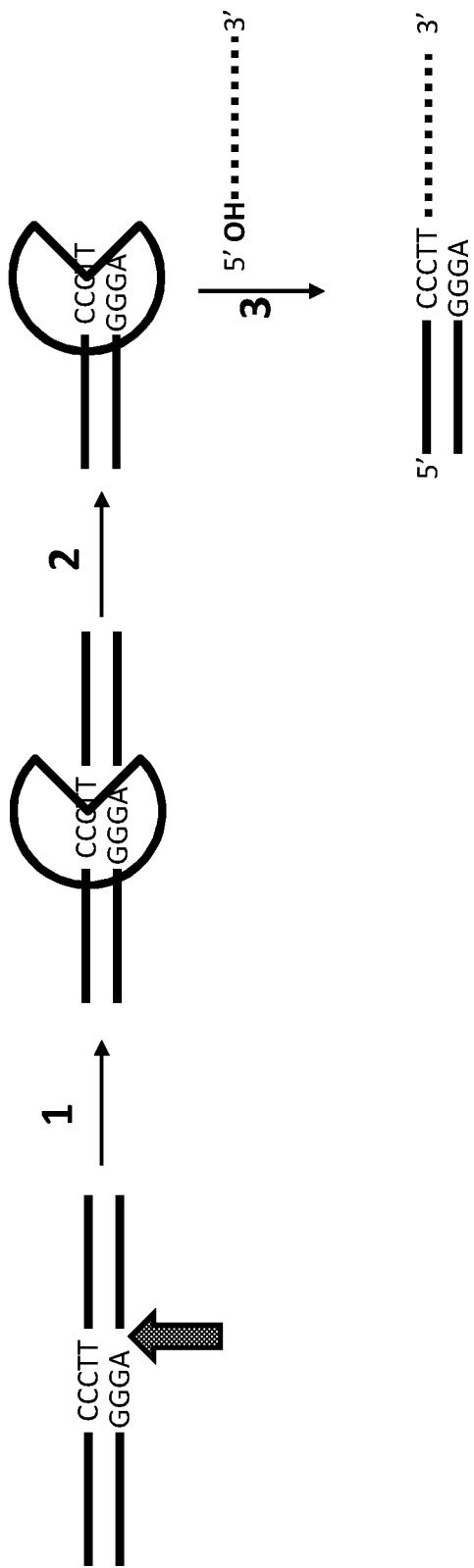
FIG. 6 shows a possible method of attaching dsDNA onto a strand of RNA using a topoisomerase. In this cartoon figure, dsDNA is attached to a strand of RNA which has a free hydroxyl at its 5' end (the 7-methylguanosine cap and 5'phosphate present at the 5' end of eukaryotic RNA would need to be removed with, for example a phosphatase such as antarctic phosphatase or alkaline phosphatase). The vaccinia topoisomerase binds onto the dsDNA at the sequence shown (step 1). The red arrow highlights that there is a nick in the lower strand of the dsDNA opposite the second thymine. Once the topoisomerase has bound it cuts the upper strand of the DNA, after the second thymine, and remains bound to the dsDNA (step 2). The topoisomerase which is bound to the dsDNA was then incubated with RNA which has a free 5' hydroxyl (step 3). The topoisomerase then joins the RNA to the dsDNA.
Figure 7:
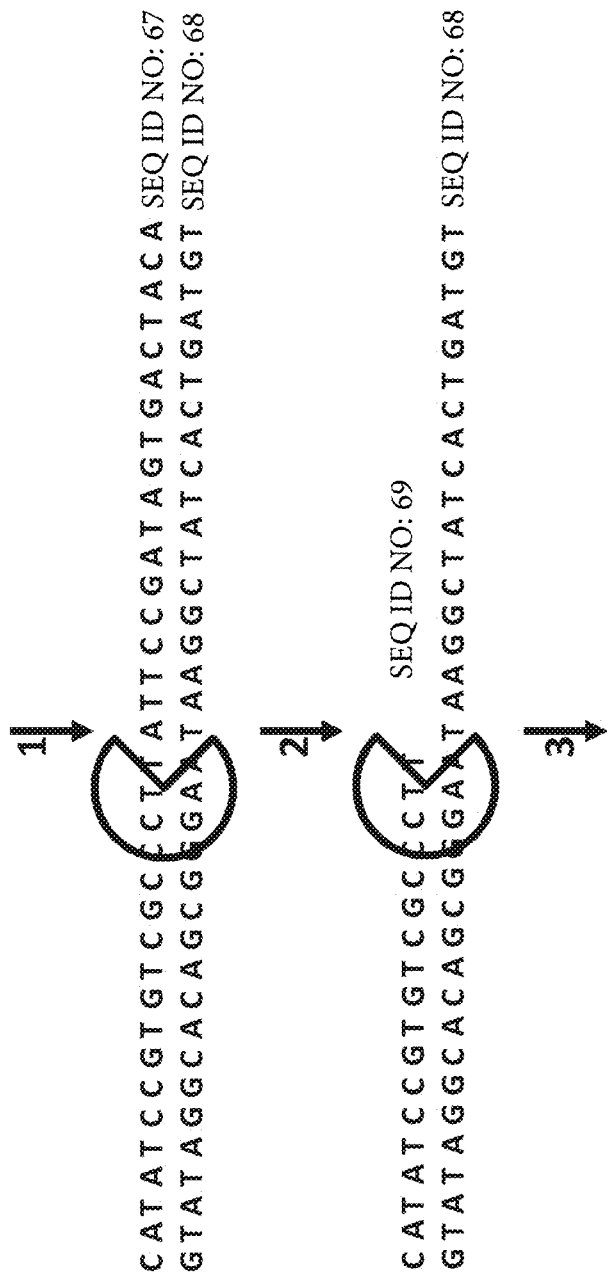
FIG. 7 shows another possible method of attaching dsDNA onto a strand of RNA using a topoisomerase. In this cartoon figure, the dsDNA is attached to a strand of RNA using a single-stranded region of DNA to hybridise to the RNA and assist in the RNA attachment. The vaccinia topoisomerase binds onto the dsDNA at the sequence shown (step 1). The lower strand of DNA does not have a nick in it. Once the topoisomerase has bound it cuts the upper strand of the DNA only, after the second thymine, and remains bound to the dsDNA/ssDNA (step 2). The topoisomerase which is bound to the dsDNA was then incubated with RNA which has a free 5' hydroxyl (step 3). The topoisomerase then joins the RNA to the dsDNA. The ssDNA region assists in attracting the complementary RNA sequence to the point of attachment to the DNA.

Topoisomerases bind to either single-stranded or double-stranded DNA and cut the phosphate backbone of the DNA. This intermediate break allows the DNA to be untangled or unwound, and, at the end of these processes, the DNA backbone is resealed again. Suitable topoisomerase binding strategies are illustrated in FIGS. 6 and 7.

Other Methods

An alternative method of attaching the RNA target polynucleotide to a non-RNA polynucleotide comprises exploiting the 5' ends of eukaryotic RNA which are modified by the addition of a 7 methyl guanosine cap in the opposite orientation. The 5' ends of eukaryotic RNA therefore contains or comprises reversed bases i.e., at the 5' end of the RNA strand the individual base has its 3' end free, as opposed the 5' end. The target RNA polynucleotide can be ligated to a non-RNA polynucleotide (which may or may not comprise a ribonucleotide or RNA sequence) which also has a region with reversed bases such that it runs in the opposite direction, as illustrated by FIG. 12 wherein the non-RNA polynucleotide is DNA. Alternatively non-RNA polynucleotide may have a section of RNA with reversed bases at one end. This section of reversed RNA bases can be attached to the reversed bases at the 5' end of eukaryotic RNA by ligation.

The non-RNA polynucleotide may or may not comprise a pre-bound DNA helicase enzyme.

Eukaryotic RNA

In eukaryotes the primary RNA transcript produced in the nucleus is processed in several ways before transport to the cytoplasm where it is used to program the translation machinery. First, a cap consisting of a 7-methyl guanosine residue linked to the 5' end of the transcript by a triphosphate bond is added during transcription (capping). Capping involves a 5'-5' triphosphate linkage. The caps are recognised by the translation machinery and protect the growing RNA chain from degradation by nucleases. Then stretches of adenosine residues are added at the 3' ends (polyadenylation). These polyA tails are 150 to 200 residues long. After these modifications, RNA splicing removes intervening sequences (i.e., the introns).

In one embodiment of the invention the 5' cap is left in place and at least one chemically reactive group is added to the 5' end of the target RNA polynucleotide. Any methods of chemical attachment may be used in the methods of the invention so long as a) the chemical reaction does not damage the RNA or DNA structure and b) the reactive linkage that is produced is not so bulky that the DNA helicase enzyme cannot move along it or past it. The at least one reactive group may be added to the target RNA polynucleotide using a hypermethylase enzyme. In one embodiment of the invention the at least one reactive group added to the RNA polynucleotide is a click reactive group although this is not essential. The at least one reactive group added to the RNA polynucleotide may alternatively be any suitable reactive group such as Thiol. At least one reactive group is also attached to the end of a non-RNA polynucleotide (which may or may not comprise a ribonucleotide or RNA sequence). Preferably the at least one reactive group is attached to the 3' end of the non-RNA polynucleotide. Preferably the non-RNA polynucleotide is a DNA strand. The at least one reactive group added to the non-RNA polynucleotide may be added using a hypermethylase enzyme. In one embodiment of the invention the at least one reactive group added to the non-RNA polynucleotide is a click reactive group although this is not essential. The one or more reactive groups on each of the RNA polynucleotide and non-RNA polynucleotide are then contacted under suitable conditions to form a covalent bond. ATP gamma S and enzyme can be used to add a thiophosphate to DNA which could then be attached to RNA which has a maleimide attached.

In an alternative embodiment of the invention the 7-methylguanosine cap is removed, preferably using Tobacco Acid Pyrophosphatase to form a de-capped RNA strand. The de-capped target RNA polynucleotide can then be treated in a number of different ways in order to produce a strand of RNA polynucleotide attached to a non-RNA polynucleotide. In one embodiment, at least one reactive group can be added to the 5' end of the de-capped RNA polynucleotide. The at least one reactive group may be added to the RNA polynucleotide using a hypermethylase enzyme. In one embodiment of the invention the at least one reactive group added to the RNA polynucleotide is a click reactive group although this is not essential. The reactive group added to the RNA polynucleotide may alternatively be any suitable reactive group such as Thiol. At least one reactive group is also attached to the end of a non-RNA polynucleotide. Preferably the at least one reactive group is attached to the 3' end of the non-RNA polynucleotide. Preferably the non-RNA polynucleotide is a DNA strand. The at least one reactive group added to the non-RNA polynucleotide may be added using a hypermethylase enzyme. In one embodiment of the invention the at least one reactive group added to the non-RNA polynucleotide is a click reactive group although this is not essential. The one or more reactive groups on each of the RNA polynucleotide and non-RNA polynucleotide are then contacted under suitable conditions to form a covalent bond.

Alternatively, a strand of non-RNA polynucleotide can be ligated directly onto the target RNA polynucleotide using a ligase, such as T4 DNA ligase, E. coli DNA ligase. Taq DNA ligase. Tma DNA ligase, 9° N DNA ligase, T4 Polymerase 1, T4 Polymerase 2, Thermostable 5' App DNA/RNA ligase, SplintR, circ Ligase. T4 RNA ligase 1, T4 RNA ligase 2. Preferably the non-RNA polynucleotide is a DNA strand. In one embodiment of the invention, one or more enzymes may be pre-bound to the non-RNA polynucleotide that is to be ligated to the RNA. Pre-loading the enzymes on the non-RNA polynucleotide speeds up the sample preparation process and means that fewer tubes are used. Alternatively the non-RNA polynucleotide that is to be ligated to the RNA polynucleotide does not contain or comprise pre-bound enzyme.

In an alternative embodiment of the invention, the non-RNA polynucleotide is a DNA primer with a leader sequence that is hybridised to an RNA polynucleotide. One or more enzymes may be pre-bound to the DNA primer that is to be hybridised to the RNA polynucleotide. Alternatively the DNA primer that is to be hybridised to the RNA polynucleotide does not contain or comprise pre-bound enzyme. Reverse transcription of the RNA polynucleotide from the DNA primer results in a 3' overhang of one to three C's, depending on the reverse transcriptase enzyme used. A DNA hairpin can then be ligated to the double-stranded DNA/RNA. Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). Hybridisation can be carried out under low stringency conditions, for example in the presence of a buffered solution of 30 to 35% formamide, 1 M NaCl and 1% SDS (sodium dodecyl sulfate) at 37° C. followed by a wash in from 1× (0.1650 M Na+) to 2× (0.33 M Na+) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M Na+) to 1× (0.1650 M Na+) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M Na+) SSC at 60° C. In particular, the conditions are preferably 10 uM oligomers in 10 mM Tris-HCl, 50 mM NaCl, pH 7 and heat to 98C before cooling to 18° C. at 2° C. per minute.

Figure 1:
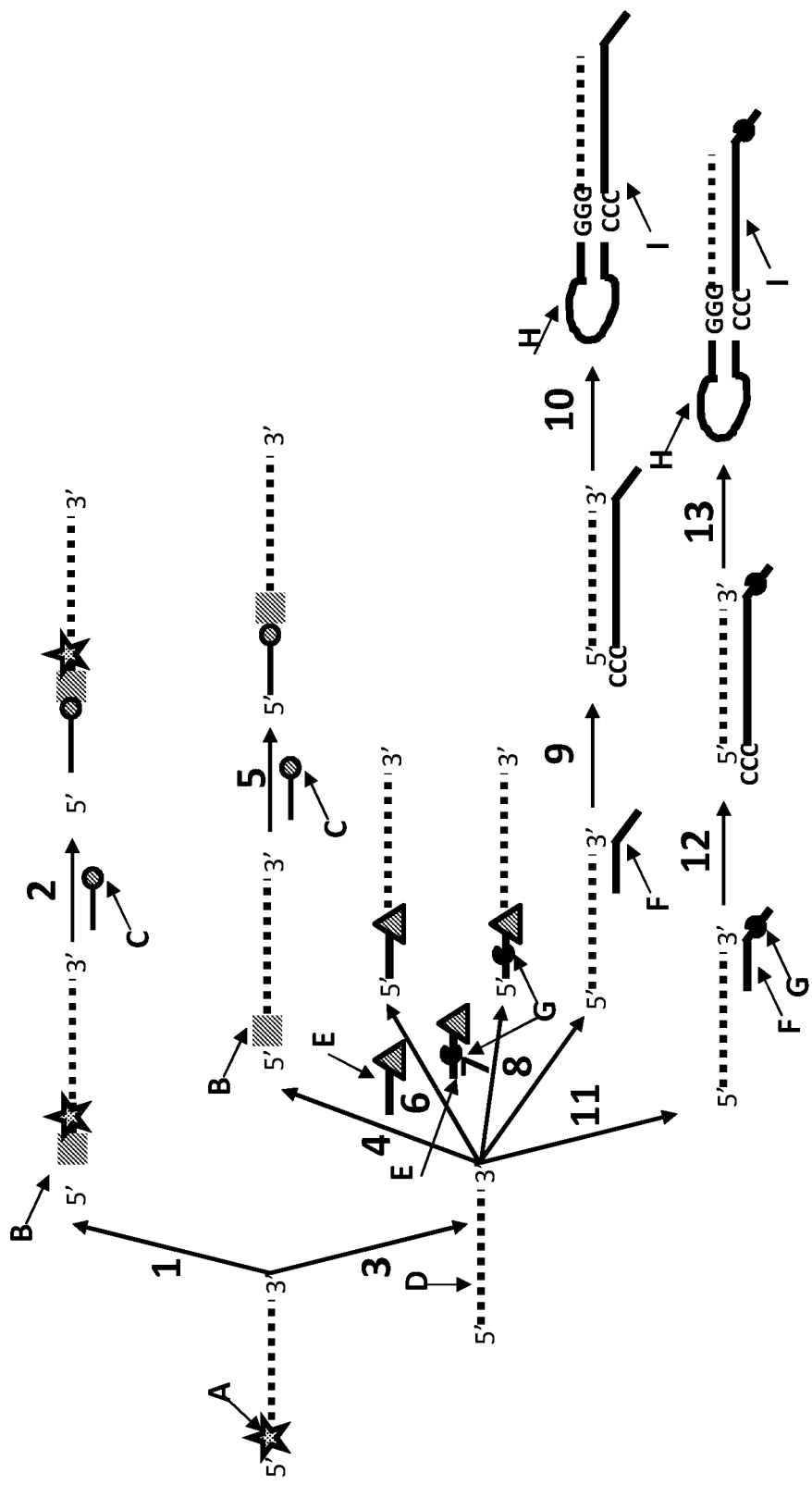
FIG. 1 shows a cartoon representation of methods of attaching a strand of eukaryotic RNA (shown as a dashed line) to a strand of DNA (shown as a solid line). Eukaryotic RNA has 7-methylguanosine cap at the 5' end (shown as a star shape and labelled A). Reaction Step 1 leaves the 7-methylguanosine cap in place and adds a reactive group (labelled B and shown as a square) to the 5' end of the eukaryotic RNA. The reactive group is added using a hypermethylase enzyme, for example Trimethyl guanosine synthase with modified SAdenosyl Methiamine. Step 2 shows a chemical reaction step where the DNA strand, which also has a reactive group labelled C attached and shown as a circle, is reacted with the other reactive group (B) to form a covalent bond. Step 3 removes the 7-methylguanosine cap using Tobacco acid phosphatase which results in the RNA strand labelled D. It is then possible to treat the RNA (with the 7-methylguanosine cap removed, labelled D) in a number of different ways in order to produce a strand of RNA attached to a strand of DNA (steps 4, 6, 7, 8 or 11). In step 4 a reactive group (labelled B and shown as a square) is added to the 5' end of RNA strand D. Step 5 shows a chemical reaction step where the DNA strand which also has a reactive group labelled C attached and the reactive group is shown as a circle is reacted with the other reactive group (B) to form a covalent bond. Steps 6 and 7 show that a strand of DNA (labelled E) can be ligated directly onto the RNA using, for example, T4 RNA Polymerase 1, T4 RNA Polymerase 2, Thermostable 5' App DNA/RNA ligase etc. In step 7 an enzyme (labelled G) is pre-bound to the DNA whereas in step 6 no enzyme is pre-bound. Steps 8 and 11 show the hybridisation of a DNA primer, with a leader (labelled F), to the RNA strand D. In step 11 an enzyme (labelled G) is pre-bound to the DNA primer whereas in step 8 no enzyme is pre-bound. Steps 9 and 12 show the reverse transcription of RNA strand D which results in a 3' overhang of three C's. Steps 10 and 13 show the ligation of a DNA hairpin (labelled H) to the double-stranded DNA/RNA (labelled 1).

Eukaryotic RNA typically comprises polyA tail, i.e. a stretch of consecutive adenosine monophosphates. The polyA tail is typically at the 3' end of the RNA. In such embodiments, a primer can be hybridised to the polyA tail of the target RNA. The primer preferably comprises a polyU region. i.e. region containing only nucleotides based on uracil. The polyU region may contain UMP or dUMP. The polyU region may be any length, such as at least 10, at least 15, at least 20, at least 25 or more. Alternatively the primer comprises a polyT region. The polyT region may be any length, such as at least 10, at least 15, at least 20, at least 25 or more. Methods of attaching a strand of eukaryotic RNA to a strand of DNA are illustrated in FIG. 1.

In an alternative embodiment of the invention, a non-RNA polynucleotide can be attached to the target RNA polynucleotide using a topoisomerase-based strategy (Cheng and Shuman, 2000, Nucleic Acids Research, Vol. 28, No. 9 1893-1898, incorporated by reference herein). DNA topoisomerase binds to duplex DNA and incises the phosphodiester backbone of one strand at a specific target site. The other strand of the duplex DNA comprises a nick or break in the sequence at a corresponding position. Once the topoisomerase has bound and cut the upper strand of the DNA it remains bound to the dsDNA. The topoisomerase which is bound to the dsDNA can transfer the DNA strand to a 5' OH terminated RNA strand to form a tandem DNA-RNA copolymer if it is then incubated with RNA which has a free 5' hydroxyl. The target RNA must have a free 5' hydroxyl: Eukaryotic RNA must be de-capped to produce RNA with a free 5' hydroxyl whereas microRNA has a free 5' hydroxyl group (See FIG. 6).

In an alternative topoisomerase-based strategy, the dsDNA is attached to a strand of RNA using a single-stranded region of DNA to hybridise to the RNA and assist in the RNA attachment (Sekiguchi et al., 1997, The Journal of Biological Chemistry, Vol 272, No. 25, 15721-15728, incorporated by reference herein). The topoisomerase binds onto the dsDNA at the specific target sequence. The lower strand of DNA does not have a nick in it. Once the topoisomerase has bound it cuts the upper strand of the DNA only and remains bound to the dsDNA/ssDNA hybrid. The topoisomerase, which is bound to the dsDNA, is then incubated with RNA that has a free 5' hydroxyl and joins the RNA to the dsDNA. The ssDNA region assists in attracting the complementary RNA sequence to the point of attachment to the DNA (See FIG. 7).

An alternative method of attaching an RNA polynucleotide to a non-RNA polynucleotide comprises exploiting the 5' ends of eukaryotic RNA which are modified by the addition of a 7-methylguanosine cap which runs in the opposite orientation. The 5' ends of eukaryotic RNA therefore contains or comprises a guanine base which has been reversed i.e., it is at the 5' end of the RNA strand but the individual base has its 3' end free, as opposed the 5' end. The target RNA can be ligated to a DNA (or RNA) sequence which also has a region with reversed bases such that it runs in the opposite direction (See FIG. 12).

Prokaryotic RNA

The Poly A Polymerase enzyme can be utilised to add a poly(dA) tail onto the 3' end of the RNA polynucleotide. In one embodiment of the invention, the non-RNA polynucleotide is a DNA primer with a leader sequence which is hybridised to an RNA polynucleotide. A DNA primer with a leader sequence can be hybridised to the poly(dA) region. One or more enzymes may be pre-bound to the DNA primer that is to be hybridised to the RNA polynucleotide. Alternatively the DNA primer that is to be hybridised to the RNA polynucleotide does not contain or comprise pre-bound enzyme. Reverse transcription of the RNA polynucleotide from the DNA primer results in a 3' overhang of one to three C's depending on the reverse transcriptase enzyme used (three to four for SuperScript II (MMLV) (see p 1192 Biotechniques Vol 29 No 6 (2000). A DNA hairpin can then be ligated to the double-stranded DNA/RNA.

In an alternative embodiment of the invention, a poly (dA) region is not added to the RNA polynucleotide and the prokaryotic RNA polynucleotide is used directly in the reaction steps. A reactive group can be added to the 5' or 3' end of the RNA polynucleotide. Preferably at least one reactive group is added to the 5' end of RNA polynucleotide.

The at least one reactive group added to the RNA polynucleotide may be a click reactive group although this is not essential. The at least one reactive group added to the RNA polynucleotide may alternatively be any suitable reactive group such as Thiol. At least one reactive group is also attached to the end of a non-RNA polynucleotide. Preferably the at least one reactive group is attached to the 3' end of the non-RNA polynucleotide. Preferably the non-RNA polynucleotide comprises a DNA strand. The at least one reactive group added to the non-RNA polynucleotide may be added using a hypermethylase enzyme. In one embodiment of the invention the at least one reactive group added to the non-RNA polynucleotide is a click reactive group although this is not essential. The one or more reactive groups on each of the RNA and non-RNA polynucleotide are then contacted under suitable conditions to form a covalent bond.

Figure 2:
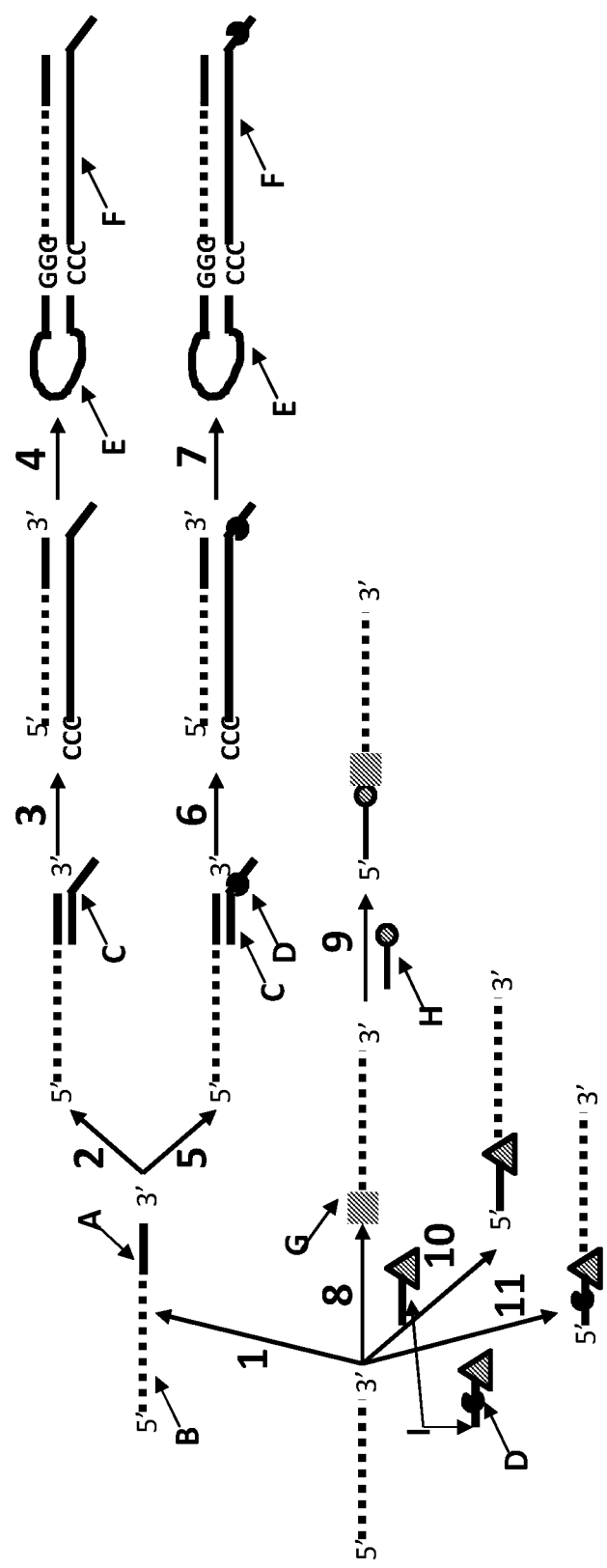
FIG. 2 shows a cartoon representation of methods of attaching a strand of prokaryotic RNA (shown as a dashed line) to a strand of DNA (shown as a solid line). Reaction Step 1 uses, for example the PolyA Polymerase enzyme to add a poly(dA) tail (labelled A) onto the 3' end of the RNA strand resulting in strand B. Steps 2 and 5 show the hybridisation of a DNA primer with a leader (labelled C) to the poly(dA) region (labelled A). In step 5 an enzyme (labelled D) is pre-bound to the DNA primer whereas in Step 2 no enzyme is pre-bound. Steps 3 and 6 show the reverse transcription of RNA strand B which results in a 3' overhang of one to three C's. Steps 4 and 7 show the ligation of a DNA hairpin (labelled E) to the double-stranded DNA/RNA (labelled F). Reaction steps 8, 10 and 11 occur directly on prokaryotic RNA rather than by adding the poly(dA) region to the RNA. In step 8 a reactive group (labelled G and shown as a square) is added to the 5' end of RNA strand. Step 9 shows a chemical reaction step where the DNA strand which also has a reactive group attached (labelled H and the reactive group is shown as a circle) is reacted with the other reactive group (G) to form a covalent bond. Steps 10 and 11 show that a strand of DNA (labelled I) can be ligated directly onto the RNA using, for example, T4 RNA Polymerase 1, T4 RNA Polymerase 2, Thermostable 5' App DNA/RNA ligase etc. In step 11 an enzyme (labelled D) is pre-bound to the DNA whereas in step 10 no enzyme is pre-bound.

In an alternative embodiment of the invention, a strand of non-RNA polynucleotide can be ligated directly onto the target RNA polynucleotide using a ligase, such as T4 DNA ligase, E. coli DNA ligase, Taq DNA ligase, Tma DNA ligase, 9° N DNA ligase, T4 Polymerase I, T4 Polymerase 2, Thermostable 5' App DNA/RNA ligase, SplintR, circ Ligase, T4 RNA ligase 1 and T4 RNA ligase 2. Preferably the non-RNA polynucleotide comprises a DNA strand. In one embodiment of the invention, one or more enzymes may be pre-bound to the non-RNA polynucleotide that is to be ligated to the RNA polynucleotide. Alternatively the non-RNA polynucleotide that is to be ligated to the RNA polynucleotide does not contain or comprise pre-bound enzyme. Methods of attaching prokaryotic RNA polynucleotide to a non-RNA (e.g., DNA) polynucleotide are illustrated in FIG. 2.

In an alternative embodiment of the invention, a non-RNA polynucleotide can be attached to the target RNA polynucleotide using a topoisomerase-based strategy (Cheng and Shuman, 2000, Nucleic Acids Research, Vol. 28, No. 9 1893-1898, incorporated by reference herein). DNA topoisomerase binds to duplex DNA and incises the phosphodiester backbone of one strand at a specific target site. The other strand of the duplex DNA comprises a nick or break in the sequence at a corresponding position. Once the topoisomerase has bound and cut the upper strand of the DNA it remains bound to the dsDNA. The topoisomerase which is bound to the dsDNA can transfer the DNA strand to a 5' OH terminated RNA strand to form a tandem DNA-RNA copolymer if it is then incubated with RNA which has a free 5' hydroxyl. The target RNA must have a free 5' hydroxyl. In an alternative topoisomerase-based strategy, the dsDNA is attached to a strand of RNA using a single-stranded region of DNA to hybridise to the RNA and assist in the RNA attachment (Sekiguchi et al., 1997, The Journal of Biological Chemistry, Vol 272, No. 25, 15721-15728, incorporated by reference herein). The topoisomerase binds onto the dsDNA at the specific target sequence. The lower strand of DNA does not have a nick in it. Once the topoisomerase has bound it cuts the upper strand of the DNA only and remains bound to the dsDNA/ssDNA hybrid. The topoisomerase which is bound to the dsDNA is then incubated with RNA which has a free 5' hydroxyl and joins the RNA to the dsDNA. The ssDNA region assists in attracting the complementary RNA sequence to the point of attachment to the DNA (See FIG. 7).

No Amplification

The target RNA polynucleotide is typically not amplified in the method of the invention. The method typically does not comprise making multiple copies of the target RNA.

The method preferably does not comprise polymerase chain reaction (PCR) or reverse transcription PCR (RT-PCR).

As discussed above, in one embodiment of the invention the RNA polynucleotide comprises a DNA complement that has been generated using a DNA primer and a reverse transcriptase. Linking of the RNA and DNA strands using a bridging moiety enables a 2D read.

In an alternative embodiment of the invention, a hairpin forming oligonucleotide is itself used as a primer for reverse-transcription to generate an RNA-cDNA construct and enable a 2 dimensional read (i.e., RNA and cDNA strand).

DNA Helicase(s) and Molecular Brake(s)

DNA helicases are used to control the movement of RNA polynucleotide through the pore. The DNA helicase enzyme does not need to display enzymatic activity as long as it is capable of binding the target RNA polynucleotide and controlling its movement through the pore. For instance, the enzyme may be modified to remove its enzymatic activity or may be used under conditions which prevent it from acting as an enzyme.

The helicase may be or be derived from a Hel308 helicase, a RecD helicase, such as TraI helicase or a TrwC helicase, a XPD helicase or a Dda helicase. The DNA helicase may be derived from Hel308 Mbu (SEQ ID NO: 8), Hel308 Csy (SEQ ID NO: 9), Hel308 Tga (SEQ ID NO: 10), Hel308 Mhu (SEQ ID NO: 11), TraI Eco (SEQ ID NO: 12), XPD Mbu (SEQ ID NO: 13), Dda 1993 (SEQ ID NO: 14) or a variant thereof.

The helicase may be any of the DNA helicases, modified DNA helicases or DNA helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736.

Helicases may work in two modes with respect to the pore. First, the method is preferably carried out using a DNA helicase such that it controls movement of the RNA polynucleotide through the pore with the field resulting from the applied voltage. In this mode the 5' end of the RNA polynucleotide is first captured in the pore, and the enzyme controls movement of the RNA polynucleotide into the pore such that the RNA polynucleotide is passed through the pore with the field until it finally translocates through to the trans side of the membrane. Alternatively, the method is preferably carried out such that a DNA helicase enzyme controls movement of the RNA polynucleotide through the pore against the field resulting from the applied voltage. In this mode the 3' end of the RNA polynucleotide is first captured in the pore, and the enzyme controls movement of the RNA polynucleotide through the pore such that the RNA polynucleotide is pulled out of the pore against the applied field until finally ejected back to the cis side of the membrane.

The DNA helicase preferably comprises the sequence shown in SEQ ID NO: 15 (Trwc Cba) or a variant thereof, the sequence shown in SEQ ID NO: 8 (Hel308 Mbu) or a variant thereof or the sequence shown in SEQ ID NO: 14 (Dda) or a variant thereof. Variants may differ from the native sequences in any of the ways discussed below for transmembrane pores. A preferred variant of SEQ ID NO: 14 comprises (a) E94C and A360C or (b) E94C, A360C, C109A and C136A and then optionally (ΔM1)G1 (i.e. deletion of M1 and then addition of G1).

Any number of helicases may be used in accordance with the invention. For instance, 1, 2, 3, 4, 5, 6, 7, 8, 9, 10 or more helicases may be used. In some embodiments, different numbers of helicases may be used. In one embodiment of the invention the DNA helicase is pre-bound to the non-RNA polynucleotide.

The method of the invention preferably comprises contacting the polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

A variant of SEQ ID NO: 8, 9, 10, 11, 12, 13, 14 or 15 is an enzyme that has an amino acid sequence which varies from that of SEQ ID NO: 8, 9, 10, 11, 12, 13, 14 or 15 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

Over the entire length of the amino acid sequence of SEQ ID NO: 8, 9, 10, 11, 12, 13, 14 or 15, a variant will preferably be at least 50% homologous to that sequence based on amino acid similarity or identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 8, 9, 10, 11, 12, 13, 14 or 15 over the entire sequence. There may be at least 80%, for example at least 85%, 90% or 95%, amino acid similarity or identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

In a preferred embodiment, the method comprises:
(a) providing RNA polynucleotide with one or more DNA helicases and one or more molecular brakes, wherein the RNA polynucleotide is modified to comprise a non-RNA polynucleotide and increase DNA helicase binding thereto;

(b) contacting the RNA polynucleotide with a transmembrane pore and applying a potential across the pore such that the one or more DNA helicases and the one or more molecular brakes are brought together and both control the movement of the RNA polynucleotide through the pore;

(c) taking one or more measurements as the RNA polynucleotide moves with respect to the pore wherein the measurements are indicative of one or more characteristics of the RNA polynucleotide and thereby characterising the RNA polynucleotide.

This type of method is discussed in detail in UK Application No. 1406151.9. A preferred molecular brake is TrwC Cba-Q594A (SEQ ID NO: 15 with the mutation Q594A). This variant does not function as a helicase (i.e. binds polynucleotides but does not move along them when provided with all the necessary components to facilitate movement, e.g. ATP and $Mg^{2+}$).

The one or more helicases may be any of those discussed above. The one or more molecular brakes may be any compound or molecule which binds to the RNA polynucleotide and slows the movement of the RNA polynucleotide through the pore. The one or more molecular brakes preferably comprise one or more compounds which bind to the RNA polynucleotide. The one or more compounds are preferably one or more macrocycles. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodextrin ($am_7$-βCD), 6-monodeoxy-6-mono-amino-β-cyclodextrin ($am_1$-βCD) or heptakis-(6-deoxy-6-guanidino)-cyclodextrin ($gu_7$-βCD).

The one or more molecular brakes are preferably not one or more single stranded binding proteins (SSB). The one or more molecular brakes are more preferably not a single-stranded binding protein (SSB) comprising a carboxy-terminal (C-terminal) region which does not have a net negative charge or (ii) a modified SSB comprising one or more modifications in its C-terminal region which decreases the net negative charge of the C-terminal region. The one or more molecular brakes are most preferably not any of the SSBs disclosed in International Application No. PCT/GB2013/051924 (published as WO 2014/013259).

The one or more molecular brakes are preferably one or more polynucleotide binding proteins. The polynucleotide binding protein may be any protein that is capable of binding to the RNA polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. The one or more molecular brakes may be derived from any of the polynucleotide handling enzymes discussed above. Modified versions of Phi29 polymerase (SEQ ID NO: 8) which act as molecular brakes are disclosed in U.S. Pat. No. 5,576,204. The one or more molecular brakes are preferably derived from a helicase.

Any number of molecular brakes derived from a helicase may be used. For instance, 1, 2, 3, 4, 5, 6, 7, 8, 9, 10 or more helicases may be used as molecular brakes. If two or more helicases are be used as molecular brakes, the two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. The one or more molecular brakes derived from helicases are preferably modified to reduce the size of an opening in the polynucleotide binding domain through which in at least one conformational state the polynucleotide can unbind from the helicase. This is disclosed in WO 2014/013260.

Preferred helicase constructs for use in the invention are described in International Application Nos. PCT/GB2013/051925 (published as WO 2014/013260); PCT/GB2013/051924 (published as WO 2014/013259) and PCT/GB2013/051928 (published as WO 2014/013262); and in UK Application No. 1318464.3 filed on 18 Oct. 2013.

If the one or more helicases are used in the active mode (i.e. when the one or more helicases are provided with all the necessary components to facilitate movement, e.g. ATP and $Mg^{2+}$), the one or more molecular brakes are preferably (a) used in an inactive mode (i.e. are used in the absence of the necessary components to facilitate movement or are incapable of active movement), (b) used in an active mode where the one or more molecular brakes move in the opposite direction to the one or more helicases or (c) used in an active mode where the one or more molecular brakes move in the same direction as the one or more helicases and more slowly than the one or more helicases.

If the one or more helicases are used in the inactive mode (i.e. when the one or more helicases are not provided with all the necessary components to facilitate movement, e.g. ATP and $Mg^{2+}$ or are incapable of active movement), the one or more molecular brakes are preferably (a) used in an inactive mode (i.e. are used in the absence of the necessary components to facilitate movement or are incapable of active movement) or (b) used in an active mode where the one or more molecular brakes move along the polynucleotide in the same direction as the polynucleotide through the pore.

The one or more helicases and one or more molecular brakes may be attached to the RNA at any positions so that they are brought together and both control the movement of the RNA through the pore. The one or more helicases and one or more molecular brakes are at least one nucleotide apart, such as at least 5, at least 10, at least 50, at least 100, at least 500, at least 1000, at least 5000, at least 10,000, at least 50,000 nucleotides or more apart. If the method concerns characterising a double stranded RNA polynucleotide provided with a Y adaptor at one end and a hairpin loop adaptor at the other end, the one or more helicases are preferably attached to the Y adaptor and the one or more molecular brakes are preferably attached to the hairpin loop adaptor. In this embodiment, the one or more molecular brakes are preferably one or more helicases that are modified such that they bind the RNA polynucleotide but do not function as a helicase. The one or more DNA helicases attached to the Y adaptor are preferably stalled at a spacer as discussed in more detail below. The one or more molecular brakes attached to the hairpin loop adaptor are preferably not stalled at a spacer. The one or more DNA helicases and the one or more molecular brakes are preferably brought together when the one or more DNA helicases reach the hairpin loop. The one or more DNA helicases may be attached to the Y adaptor before the Y adaptor is attached to the polynucleotide or after the Y adaptor is attached to the polynucleotide. The one or more molecular brakes may be attached to the hairpin loop adaptor before the hairpin loop adaptor is attached to the polynucleotide or after the hairpin loop adaptor is attached to the polynucleotide.

The one or more helicases and the one or more molecular brakes are preferably not attached to one another. The one or more helicases and the one or more molecular brakes are more preferably not covalently attached to one another. The one or more helicases and the one or more molecular brakes are preferably not attached as described in International Application Nos. PCT/GB2013/051925 (published as WO 2014/013260); PCT/GB2013/051924 (published as WO 2014/013259) and PCT/GB2013/051928 (published as WO 2014/013262), and in UK Application No. 1318464.3 filed on 18 Oct. 2013.

Spacer(s)

One or more spacers can be included in the constructs of the invention. When a part of the RNA polynucleotide enters the pore and moves through the pore along the field resulting from the applied potential, the one or more helicases are moved past the spacer by the pore as the RNA polynucleotide moves through the pore. This is because the RNA polynucleotide (including the one or more spacers) moves through the pore and the one or more helicases remain on top of the pore. The one or more DNA helicases may be stalled at the one or more spacers as discussed in International Application No. PCT/GB2014/050175 (published as WO 2014/135838). Any configuration of one or more helicases and one or more spacers disclosed in the International Application may be used in this invention.

The one or more spacers can be part of the target RNA polynucleotide, for instance it/they interrupt(s) the polynucleotide sequence. The one or more spacers are preferably not part of one or more blocking molecules, such as speed bumps, hybridised to the target RNA. The one or more spacers can be part of the non-RNA polynucleotide (e.g., a DNA polynucleotide), for instance it/they interrupt(s) the polynucleotide sequence. The one or more spacers can be part of the RNA polynucleotide. The one or more spacers can be attached to the target RNA polynucleotide and/or the non-RNA polynucleotide. The one or more spacers may be positioned at the ends or the RNA polynucleotide or non-RNA polynucleotide and/or the one or more spacers may be positioned within the RNA polynucleotide or non-RNA polynucleotide.

There may be any number of spacers in the target RNA polynucleotide or non-RNA polynucleotide such as 1, 2, 3, 4, 5, 6, 7, 8, 9, 10 or more spacers. There are preferably two, four or six spacers in a construct of the invention. There may be one or more spacers in different regions of the construct, such as a spacer in the leader sequence and a spacer in the hairpin loop.

The one or more spacers each provides an energy barrier which the one or more helicases cannot overcome even in the active mode. The one or more spacers may stall the one or more helicases by reducing the traction of the helicase (for instance by removing the bases from the nucleotides in the target RNA polynucleotide or non-RNA polynucleotide) or physically blocking movement of the one or more helicases (for instance using a bulky chemical group).

The one or more spacers may comprise any molecule or combination of molecules that stalls the one or more helicases. The one or more spacers may comprise any molecule or combination of molecules that prevents the one or more helicases from moving along the target RNA polynucleotide. It is straightforward to determine whether or not the one or more helicases are stalled at one or more spacers in the absence of a transmembrane pore and an applied potential. For instance, the ability of a helicase to move past a spacer can be measured by PAGE.

The one or more spacers typically comprise a linear molecule, such as a polymer. The one or more spacers typically have a different structure from the target RNA polynucleotide or non-RNA polynucleotide. For instance, the one or more spacers are typically not RNA. In particular, the one or more spacers preferably comprise peptide nucleic acid (PNA), glycerol nucleic acid (GNA), threose nucleic acid (TNA), locked nucleic acid (LNA) or a synthetic polymer with nucleotide side chains. The one or more spacers may comprise one or more nucleotides in the opposite direction from the polynucleotide. For instance, the one or more spacers may comprise one or more nucleotides in the 3' to 5' direction when the polynucleotide is in the 5' to 3' direction. The nucleotides may be any of those discussed above.

The one or more spacers preferably comprises one or more nitroindoles, such as one or more 5-nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more iso-deoxycytidines (Iso-dCs), one or more Iso-deoxyguanosines (Iso-dGs), one or more iSpC3 groups (i.e. nucleotides which lack sugar and a base), one or more photo-cleavable (PC) groups, one or more hexandiol groups, one or more spacer 9 (iSp9) groups, one or more spacer 18 (iSp18) groups, a polymer or one or more thiol connections. The one or more spacers may comprise any combination of these groups. Many of these groups are commercially available from IDT, (Integrated DNA Technologies®).

The one or more spacers may contain any number of these groups. For instance, for 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections, the one or more spacers preferably comprise 2, 3, 4, 5, 6, 7, 8, 9, 10, 11, 12 or more. The one or more spacers preferably comprise 2, 3, 4, 5, 6, 7, 8 or more iSp9 groups. The one or more spacers preferably comprise 2, 3, 4, 5 or 6 or more iSp18 groups. The most preferred spacer is four iSpC3 groups.

The polymer is preferably a polypeptide or a polyethylene glycol (PEG). The polypeptide preferably comprises 2, 3, 4, 5, 6, 7, 8, 9, 10, 11, 12 or more amino acids. The PEG preferably comprises 2, 3, 4, 5, 6, 7, 8, 9, 10, 11, 12 or more monomer units.

The one or more spacers preferably comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide. Abasic spacers can be inserted into target polynucleotides by removing the nucleobases from one or more adjacent nucleotides. For instance, polynucleotides may be modified to include 3-methyladenine, 7-methylguanine, 1,N6-ethenoadenine inosine or hypoxanthine and the nucleobases may be removed from these nucleotides using Human Alkyladenine DNA Glycosylase (hAAG). Alternatively, polunucleotides may be modified to include uracil and the nucleobases removed with Uracil-DNA Glycosylase (UDG). In one embodiment, the one or more spacers do not comprise any abasic nucleotides.

The one or more DNA helicases may be stalled by (i.e. before) or on each linear molecule spacers. If linear molecule spacers are used, the construct is preferably provided with a double stranded region of polynucleotide adjacent to the end of each spacer past which the one or more helicases are to be moved. The double stranded region typically helps to stall the one or more helicases on the adjacent spacer. The presence of the double stranded region(s) is particularly preferred if the method is carried out at at a salt concentration of about 100 mM or lower. Each double stranded region is typically at least 10, such as at least 12, nucleotides in length. If the target polynucleotide used in the invention is single stranded, a double stranded region may formed by hybridising a shorter polynucleotide to a region adjacent to a spacer. The shorter polynucleotide is typically formed from the same nucleotides as the target polynucleotide, but may be formed from different nucleotides. For instance, the shorter polynucleotide may be formed from LNA.

If linear molecule spacers are used, the construct is preferably provided with a blocking molecule at the end of each spacer opposite to the end past which the one or more helicases are to be moved. This can help to ensure that the one or more helicases remain stalled on each spacer. It may also help retain the one or more helicases on the construct in the case that it/they diffuse(s) off in solution. The blocking molecule may be any of the chemical groups discussed below which physically cause the one or more helicases to stall. The blocking molecule may be a double stranded region of polynucleotide.

The one or more spacers preferably comprise one or more chemical groups which physically cause the one or more helicases to stall. The one or more chemical groups are preferably one or more pendant chemical groups. The one or more chemical groups may be attached to one or more nucleobases in the target polynucleotide. The one or more chemical groups may be attached to the target polynucleotide backbone. Any number of these chemical groups may be present, such as 2, 3, 4, 5, 6, 7, 8, 9, 10, 11, 12 or more. Suitable groups include, but are not limited to, fluorophores, streptavidin and/or biotin, cholesterol, methylene blue, dinitrophenols (DNPs), digoxigenin and/or anti-digoxigenin and dibenzylcyclooctyne groups.

Different spacers in the target polynucleotide may comprise different stalling molecules. For instance, one spacer may comprise one of the linear molecules discussed above and another spacer may comprise one or more chemical groups which physically cause the one or more helicases to stall. A spacer may comprise any of the linear molecules discussed above and one or more chemical groups which physically cause the one or more helicases to stall, such as one or more abasics and a fluorophore.

Suitable spacers can be designed depending on the type of target polynucleotide and the conditions under which the method of the invention is carried out. Most helicases bind and move along DNA and so may be stalled using anything that is not DNA. Suitable molecules are discussed above.

The method of the invention is preferably carried out in the presence of free nucleotides and/or the presence of a helicase cofactor. This is discussed in more detail below. In the absence of the transmembrane pore and an applied potential, the one or more spacers are preferably capable of stalling the one or more helicases in the presence of free nucleotides and/or the presence of a helicase cofactor.

If the method of the invention is carried out in the presence of free nucleotides and a helicase cofactor as discussed below (such that the one of more helicases are in the active mode), one or more longer spacers are typically used to ensure that the one or more helicases are stalled on the target polynucleotide before they are contacted with the transmembrane pore and a potential is applied. One or more shorter spacers may be used in the absence of free nucleotides and a helicase cofactor (such that the one or more helicases are in the inactive mode).

The salt concentration also affects the ability of the one or more spacers to stall the one or more helicases. In the absence of the transmembrane pore and an applied potential, the one or more spacers are preferably capable of stalling the one or more helicases at a salt concentration of about 100 mM or lower. The higher the salt concentration used in the method of the invention, the shorter the one or more spacers that are typically used and vice versa.

Preferred combinations of features are shown in the Table 1 below.

TABLE 1

| Polynucleotide | Spacer composition* | Spacer length (i.e. number of*) | Salt [ ] | Free nucleotides? | Helicase cofactor? |
|---|---|---|---|---|---|
| DNA | iSpC3 | 4 | 1M | Yes | Yes |
| DNA | iSp18 | 4 | 100-1000 mM | Yes | Yes |
| DNA | iSp18 | 6 | <100-1000 mM | Yes | Yes |
| DNA | iSp18 | 2 | 1M | Yes | Yes |
| DNA | iSpC3 | 12 | <100-1000 mM | Yes | Yes |
| DNA | iSpC3 | 20 | <100-1000 mM | Yes | Yes |
| DNA | iSp9 | 6 | 100-1000 mM | Yes | Yes |
| DNA | idSp | 4 | 1M | Yes | Yes |

The method may concern moving two or more helicases past a spacer. In such instances, the length of the spacer is typically increased to prevent the trailing helicase from pushing the leading helicase past the spacer in the absence of the pore and applied potential. If the method concerns moving two or more helicases past one or more spacers, the spacer lengths discussed above may be increased at least 1.5 fold, such 2 fold, 2.5 fold or 3 fold. For instance, if the method concerns moving two or more helicases past one or more spacers, the spacer lengths in the third column of Table 4 above may be increased 1.5 fold, 2 fold, 2.5 fold or 3 fold.

Transmembrane Pore

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936).

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide or nucleic acid, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel.

The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 2 over the entire sequence. There may be at least 80%, for example at least 85%, 90% or 95%, amino acid similarity or identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul. S. F et al (1990) J Mol Biol 215:403-10. Software for performing BLAST analyses is publicly available through the National Center for Biotechnology Information (http://www.ncbi.nlm.nih.gov/).

Similarity can be measured using pairwise identity or by applying a scoring matrix such as BLOSUM62 and converting to an equivalent identity. Since they represent functional rather than evolved changes, deliberately mutated positions would be masked when determining homology. Similarity may be determined more sensitively by the application of position-specific scoring matrices using, for example, PSIBLAST on a comprehensive database of protein sequences. A different scoring matrix could be used that reflect amino acid chemico-physical properties rather than frequency of substitution over evolutionary time scales (e.g. charge).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-(B1)8 and is called MS-(B2)8. The pore used in the invention is preferably MS-(B2)8. The further preferred variant comprises the mutations G75S/G77S/L88N/Q126R. The variant of SEQ ID NO: 2 has the mutations G75S/G77S/L88N/Q126R in addition to all the mutations of MS-(B1)8 and is called MS-(B2C)8. The pore used in the invention is preferably MS-(B2)8 or MS-(B2C)8.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are also discussed therein.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

The variant may include modifications that facilitate covalent attachment to or interaction with the helicase or construct. The variant preferably comprises one or more reactive cysteine residues that facilitate attachment to the helicase or construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a Staphylococcus bacterium. Alternatively, the variant may be expressed in vitro or recombinantly by a bacterium such as Escherichia coli. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135, 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

Membrane

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units t are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

Coupling

The target RNA polynucleotide is preferably coupled to the membrane comprising the transmembrane pore. This may be done using any known method. The method may comprise coupling the target RNA polynucleotide to the membrane comprising the transmembrane pore. The RNA polynucleotide is preferably coupled to the membrane using one or more anchors. The RNA polynucleotide may be coupled to the membrane using any known method.

Each anchor comprises a group which couples (or binds) to the RNA polynucleotide and a group that couples (or binds) to the membrane. Each anchor may covalently couple (or bind) to the RNA polynucleotide and/or the membrane. If a Y adaptor and/or a hairpin loop adaptors are used, the RNA is preferably coupled to the membrane using the adaptor(s).

The RNA polynucleotide may be coupled to the membrane using any number of anchors, such as 2, 3, 4 or more anchors. For instance, an RNA polynucleotide may be coupled to the membrane using two anchors each of which separately couples (or binds) to both the RNA polynucleotide and membrane.

The one or more anchors may comprise the one or more DNA helicases and/or the one or more molecular brakes discussed above.

If the membrane is an amphiphilic layer, such as a lipid bilayer (as discussed in detail above), the RNA is preferably coupled to the membrane via a polypeptide present in the membrane or a hydrophobic anchor present in the membrane. The hydrophobic anchor is preferably a lipid, fatty acid, sterol, carbon nanotube or amino acid.

The RNA polynucleotide may be coupled directly to the membrane. The RNA polynucleotide may be coupled to the membrane using any of the methods disclosed in International Application Number No. PCT/GB2012/051191 (published as WO 2012/164270). The RNA polynucleotide is preferably coupled to the membrane via a linker. Preferred linkers include, but are not limited to, polymers, such as polynucleotides, polyethylene glycols (PEGs) and polypeptides. If an RNA is coupled directly to the membrane, then some data will be lost as the characterising run cannot continue to the end of the RNA due to the distance between the membrane and the pore and/or polynucleotide binding protein. If a linker is used, then the RNA can be processed to completion. If a linker is used, the linker may be attached to the RNA at any position. The linker is typically attached to the RNA at the tail polymer.

The coupling may be stable or transient. For certain applications, the transient nature of the coupling is preferred. If a stable coupling molecule were attached directly to either the 5' or 3' end of an RNA, then some data will be lost as the characterising run cannot continue to the end of the complementary polynucleotide due to the distance between the membrane and the pore and/or polynucleotide binding protein. If the coupling is transient, then when the coupled end randomly becomes free of the membrane, then the RNA polynucleotide can be processed to completion. Chemical groups that form stable or transient links with the membrane are discussed in more detail below. The RNA polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

Coupling of polynucleotides to synthetic lipid bilayers has been carried out previously with various different tethering strategies. These are summarised in Table 2 below.

TABLE 2

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides may be functionalized using a modified phosphoramidite in the synthesis reaction, which is easily compatible for the addition of suitable anchoring groups, such as thiol, cholesterol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane. The advantages of transient coupling are discussed above.

Coupling of RNA polynucleotides can also be achieved by a number of other means provided that a reactive group can be added to the RNA polynucleotide.

Alternatively, the reactive group could be considered to be a short region in the RNA polynucleotide complementary to one already coupled to the membrane, so that attachment can be achieved via hybridisation. The region could be part of the RNA polynucleotide or ligated to it. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5).

Most preferably, the RNA is coupled to the membrane using a cholesterol-tagged polynucleotide which hybridises to the RNA polynucleotide or non-RNA polynucleotide attached thereto.

Diagnosing or Prognosing Diseases or Conditions mRNA is preferably used in the invention to diagnose or prognose a disease or condition. Some diseases or conditions are associated with an altered amount (or level) of mRNA. The mRNA may be normal or wild-type mRNA. i.e. not alternately spliced. The amount (or level) of the mRNA may be increased or decreased in the disease or condition compared with the amount (or level) in a patient without the disease or condition. Such diseases or conditions may be diagnosed or prognosed by determining the amount of the mRNA in a sample from the patient using a method of the invention.

Many genetic diseases or conditions are caused by mutations that cause alternate mRNA splicing, such as mRNA splicing defects. A number of diseases or conditions are associated with alternate mRNA splicing which are not attributed to overt mutations. The presence or absence of alternate splicing can be identified by determining the presence or absence of an alternately spliced mRNA in a sample from the patient using the method of the invention. In some instances, alternate mRNA splicing may be the normal function of a cell. In such instances, an increased or decreased amount (or level) of the alternately spliced mRNA compared with the normal amount (i.e. the amount in a patient without the disease or condition) may be used to diagnose or prognose the disease or condition.

The invention provides a method of diagnosing or prognosing a disease or condition associated with an altered amount and/or alternate splicing of messenger RNA (mRNA) in a patient. The invention provides a method of determining whether or not a patient has or is at risk of developing a disease or condition associated with an altered amount and/or alternate splicing of messenger RNA (mRNA). In each instance, the method comprises determining the amount and/or identity of the mRNA in a sample from the patient using a method of the invention. The disease or condition may be any of those discussed below. The disease or condition is preferably cystic fibrosis, familial dysautonomia, frontotemporal lobar dementia, amyotrophic lateral sclerosis, Hutchinson-Gilford progeria syndrome, medium-chain acyl-CoA dehydrogenase (MCAD) deficiency, myotonic dystrophy, Prader-Willi syndrome, spinal muscular atrophy, tauopathy, hypercholesterolemia or cancer. These diseases, their causes and possible treatments are discussed in Tazi et al. (Biochimica et Biophysica Acta (BBA)—Molecular Basis of Disease, Volume 1792, Issue 1, January 2009, Pages 14-26).

The presence of an altered (i.e. increased or decreased) amount (or level) of the mRNA in the sample from the patient typically diagnoses or prognoses the disease or condition, i.e. indicates that the patient has or is at risk of developing the disease or condition. The absence of an altered (i.e. increased or decreased) amount (or level) of the mRNA in the sample from the patient typically indicates that the patient does not have or is not at risk of developing the disease or condition. The amount of mRNA can be determined as discussed above.

The presence of the alternately spliced mRNA in the sample from the patient typically diagnoses or prognoses the disease or condition, i.e. indicates that the patient has or is at risk of developing the disease or condition. The absence of the alternately spliced mRNA in the sample from the patient typically indicates that the patient does not have or is not at risk of developing the disease or condition. The presence or absence of the alternately spliced mRNA can be determined by identifying RNA in the sample as discussed above.

An increased or decreased amount (or level) of the alternately spliced mRNA in the sample from the patient typically diagnoses or prognoses the disease or condition, i.e. indicates that the patient has or is at risk of developing the disease or condition. No change in the amount of the alternately spliced mRNA in the sample from the patient (compared with the amount or level in a patient without the disease or condition) typically indicates that the patient does not have or is not at risk of developing the disease or condition. The amount of the alternately spliced mRNA can be determined as discussed above.

miRNA is preferably used in the invention to diagnose or prognose a disease or condition. The invention provides a method of diagnosing or prognosing a disease or condition associated with a miRNA. The invention provides a method of determining whether or not a patient has or is at risk of developing a disease or condition associated with a miRNA. The method comprises determining the presence or absence of the miRNA in a sample from the patient using a method of the invention. The disease or condition may be any of those discussed below.

The presence of the miRNA in the sample from the patient typically indicates that the patient has or is at risk of developing the disease or condition. The absence of the miRNA in the sample from the patient typically indicates that the patient does not have or is not at risk of developing the disease or condition. The presence or absence of the miRNA can be determined by identifying any miRNAs in the sample as discussed above.

The disease or condition is preferably cancer, coronary heart disease, cardiovascular disease or sepsis. The disease or condition is more preferably abdominal aortic aneurysm, acute lymphoblastic leukemia (ALL), acute myeloid leukemia (AML), acute myocardial infarction, acute promyelocytic leukemia (APL), adenoma, adrenocortical carcinoma, alcoholic liver disease, Alzheimer's disease, anaplastic thyroid carcinoma (ATC), anxiety disorder, asthma, astrocytoma, atopic dermatitis, autism spectrum disorder (ASD), B-cell chronic lymphocytic leukemia, B-cell lymphoma. Becker muscular dystrophy (BMD), bladder cancer, brain neoplasm, breast cancer, Burkitt lymphoma, cardiac hypertrophy, cardiomyopathy, cardiovascular disease, cerebellar neurodegeneration, cervical cancer, cholangiocarcinoma, cholesteatoma, choriocarcinoma, chronic lymphocytic leukemia, chronic myeloid leukemia, chronic pancreatitis, colon carcinoma, colorectal cancer, congenital heart disease, coronary artery disease, cowden syndrome, dermatomyositis (DM), diabetic nephropathy, diarrhea predominant irritable bowel syndrome, diffuse large B-cell lymphoma, dilated cardiomyopathy, down syndrome (DS), duchenne muscular dystrophy (DMD), endometrial cancer, endometrial endometrioid adenocarcinoma, endometriosis, epithelial ovarian cancer, esophageal cancer, esophagus squamous cell carcinoma, essential thrombocythemia (ET), facioscapulohumeral muscular dystrophy (FSHD), follicular lymphoma (FL), follicular thyroid carcinoma (FTC), frontotemporal dementia, gastric cancer (stomach cancer), glioblastoma, glioblastoma multiforme (GBM), glioma, glomerular disease, glomerulosclerosis, hamartoma, HBV-related cirrhosis, HCV infection, head and neck cancer, head and neck squamous cell carcinoma (HNSCC), hearing loss, heart disease, heart failure, hepatitis B, hepatitis C, hepatocellular carcinoma (HCC), hilar cholangiocarcinoma, Hodgkin's lymphoma, homozygous sickle cell disease (HbSS), Huntington's disease (HD), hypertension, hypopharyngeal cancer, inclusion body myositis (IBM), insulinoma, intrahepatic cholangiocarcinoma (ICC), kidney cancer, kidney disease, laryngeal carcinoma, late insomnia (sleep disease), leiomyoma of lung, leukemia, limb-girdle muscular dystrophies types 2A (LGMD2A), lipoma, lung adenocarcinoma, lung cancer, lymphoproliferative disease, malignant lymphoma, malignant melanoma, malignant mesothelioma (MM), mantle cell lymphoma (MCL), medulloblastoma, melanoma, meningioma, metabolic disease, miyoshi myopathy (MM), multiple myeloma (MM), multiple sclerosis, MYC-rearranged lymphoma, myelodysplastic syndrome, myeloproliferative disorder, myocardial infarction, myocardial injury, myoma, nasopharyngeal carcinoma (NPC), nemaline myopathy (NM), nephritis, neuroblastoma (NB), neutrophilia, Niemann-Pick type C (NPC) disease, non-alcoholic fatty liver disease (NAFLD), non-small cell lung cancer (NSCLC), obesity, oral carcinomaosteosarcoma ovarian cancer (OC), pancreatic cancer, pancreatic ductal adenocarcinoma (PDAC), pancreatic neoplasia, panic disease, papillary thyroid carcinoma (PTC), Parkinson's disease, PFV-1 infection, pharyngeal disease, pituitary adenoma, polycystic kidney disease, polycystic liver disease, polycythemia vera (PV), polymyositis (PM), primary biliary cirrhosis (PBC), primary myelofibrosis, prion disease, prostate cancer, psoriasic arthritis, psoriasis, pulmonary hypertension, recurrent ovarian cancer, renal cell carcinoma, renal clear cell carcinoma, retinitis pigmentosa (RP), retinoblastoma, rhabdomyosarcoma, rheumatic heart disease and atrial fibrillation, rheumatoid arthritis, sarcoma, schizophrenia, sepsis, serous ovarian cancer, Sezary syndrome, skin disease, small cell lung cancer, spinocerebellar ataxia, squamous carcinoma, T-cell leukemia, teratocarcinoma, testicular germ cell tumor, thalassemia, thyroid cancer, tongue squamous cell carcinoma, tourette's syndrome, type 2 diabetes, ulcerative colitis (UC), uterine leiomyoma (ULM), uveal melanoma, vascular disease, vesicular stomatitis or Waldenstrom macroglobulinemia (WM).

The patient may be any of the mammals discussed above. The patient is preferably human. The patient is an individual.

The sample may be any of those discussed above. The sample is typically from any tissue or bodily fluid. The sample typically comprises a body fluid and/or cells of the patient and may, for example, be obtained using a swab, such as a mouth swab. The sample may be, or be derived from, blood, urine, saliva, skin, cheek cell or hair root samples. The target RNA is typically extracted from the sample before it is used in the method of the invention.

The method may concern diagnosis of the disease or condition in the patient, i.e. determining whether or not the patient has the disease or condition. The patient may be symptomatic.

The method may concern prognosing the disease or condition in the patient, i.e. determining whether or not the patient is likely to develop the disease or condition. The patient can be asymptomatic. The patient can have a genetic predisposition to the disease or condition. The patient may have one or more family member(s) with the disease or condition.

Method of Improving the Movement of an RNA Polynucleotide

The present invention also provides a method of moving a target RNA polynucleotide with respect to a transmembrane pore when the movement is controlled by a DNA helicase enzyme, comprising:

a) providing (i) an RNA polynucleotide wherein the RNA is modified to comprise a non-RNA polynucleotide and (ii) a DNA helicase enzyme;

b) contacting the RNA polynucleotide and DNA helicase enzyme provided in a) with a transmembrane pore such that the DNA helicase controls the movement of the RNA polynucleotide with respect to the transmembrane pore.

The modification of the RNA polynucleotide results in increased DNA helicase binding thereto. Increased DNA helicase binding to the modified RNA polynucleotide is defined as an amount or level of DNA helicase binding that is greater than, or more than, the amount or level of DNA helicase binding that is observed for non-modified or unmodified RNA polynucleotide i.e., an RNA that has not been modified in accordance with the modification methods of the invention. The level of binding of DNA helicase to a target RNA polynucleotide can be easily tested using routine methods which are known and routine to one of skill in the art.

Preferably the DNA helicase enzyme is pre-bound to the non-RNA polynucleotide. Any of the embodiments described above also apply to this method. For example, in one embodiment, a non-RNA polynucleotide may comprise at least one of—(i) a polymer of 5 or more charged units; (ii) a blocking-strand hybridisation site of approximately 20 nucleotides in length; (iii) a DNA-helicase binding site of 1 or more non-RNA nucleotides, e.g., 1, 2, 3, 4, 5, 6, 7, 8, 9, 10, 11, 12, 13, 14, 15, 16, 17, 18, 19, 20, 30, 40, or 50 nucleotides; (iv) a stalling chemistry of 1 or more units e.g., 1, 2, 3, 4, 5, 6, 7, 8, 9, 10 or more units, such as Sp18, as described in WO2014/135838 which is incorporated by reference herein; (v) a tether hybridisation site of approximately 30 nucleotides in length; and/or (vi) a sequence that facilitates ligation of the non-RNA polynucleotide to the RNA polynucleotide, as described in the preceding sections.

The Examples further illustrate the use of a DNA helicase to control the movement of a DNA/RNA strand through a nanopore. Accordingly, in one embodiment, provided herein is a method for increasing the ability or efficiency of an RNA to be sequenced through a pore.

Methods of Producing Constructs of the Invention

The method of producing a construct comprises attaching a target RNA polynucleotide to a non-RNA polynucleotide. At least one nucleotide of the non-RNA polynucleotide is not a ribonucleotide, i.e. is not from RNA. The non-RNA polynucleotide may therefore comprise at least one ribonucleotide (or RNA nucleotide) but must also additionally comprise or include a non-RNA nucleotide or sequence i.e., a nucleotide or sequence of nucleotides that is not RNA. The non-RNA polynucleotide may comprise any of the embodiments as described above. Preferably the non-RNA polynucleotide comprises a DNA helicase binding site or a DNA adaptor. More preferably the non-RNA polynucleotide comprises a leader sequence.

The site of and method of attachment are selected as discussed above. Preferably, the attachment method may be selected from chemical attachment, covalent attachment, enzymatic attachment, hybridization, synthetic methods, or using a topoisomerase. The RNA polynucleotide may be attached to the non-RNA polynucleotide at more than one, such as two or three, points. The method of attachment may involve one, two, three, four, five or more different methods of attachment. Any combination of the attachment methods described above may be used in accordance with the invention.

The method may further comprise determining whether or not the construct is capable of controlled movement through a nanopore under the control of a DNA helicase. Assays for testing this are known to those of skill in the art. If the movement of the RNA polynucleotide through a nanopore can be controlled, a construct of the invention has been produced. If the movement of the RNA polynucleotide cannot be controlled, a construct of the invention has not been produced.

In one embodiment of the invention the method of producing the construct comprising attaching a target RNA polynucleotide to a non-RNA polynucleotide takes place before the contacting step (b). In another embodiment, provided herein is a method of generating a modified RNA capable of being sequenced through a pore with greater efficiency than the RNA in unmodified form.

Modification Method of the Invention

The present invention provides a method of modifying a target RNA polynucleotide for characterisation, such as for sequencing. The modified RNA polynucleotide is characterised, or sequenced, in accordance with the invention. This is discussed in more detail above.

The method involves the formation of one or more modified RNA polynucleotides using one or more of the methods described. The one or more modified polynucleotides are easier to characterise than the unmodified polynucleotide, especially using strand sequencing.

Products/Constructs of the Invention

The invention also provides an RNA polynucleotide modified using a modification method of the invention. The target RNA polynucleotide is modified by attachment of the RNA polynucleotide to a non-RNA polynucleotide to form a construct of the invention. The modification of the target RNA necessarily results in increased interaction between a DNA helicase and the modified RNA construct i.e., as compared with interaction that occurs between DNA helicase and RNA polynucleotide in un-modified form, without the attached non-RNA polynucleotide. Additionally or alternatively, the addition or attachment of the non-RNA polynucleotide to the RNA polynucleotide means that the specificity of DNA helicase for the modified RNA construct is increased i.e., as compared to the specificity of the DNA helicase for the RNA polynucleotide in un-modified form, without the attached non-RNA polynucleotide. Additionally or alternatively, the addition or attachment of the non-RNA polynucleotide to the RNA polynucleotide means that DNA helicase binding to the modified RNA construct is facilitated and/or DNA helicase binding to the modified RNA construct is increased i.e., as compared with binding that occurs between DNA helicase and RNA polynucleotide in un-modified form, without the attached non-RNA polynucleotide. Additionally or alternatively, the addition or attachment of the non-RNA polynucleotide to the RNA polynucleotide means that the DNA helicase binds more efficiently or more strongly to the modified RNA construct and is less likely to disengage from the modified construct i.e., as compared with binding that occurs between DNA helicase and RNA polynucleotide in un-modified form, without the attached non-RNA polynucleotide. The non-RNA polynucleotide may be any polynucleotide which is not RNA. The non-RNA polynucleotide may comprise at least one ribo nucleotide but must also additionally comprise or include a non-RNA nucleotide or sequence i.e., a nucleotide or sequence of nucleotides that is not RNA. The site of and method of attachment are selected as discussed above. The non-RNA polynucleotide may or may not comprise a pre-bound DNA helicase. Preferably the non-RNA polynucleotide comprises a region to which a DNA helicase is capable of binding (a DNA helicase binding site) or a DNA adaptor. More preferably the DNA helicase binding site or the DNA adaptor comprises a leader sequence which preferentially threads into a nanopore. The leader sequence can also be used to link the target RNA to the one or more anchors as discussed above. The leader sequence may be linked to the target RNA polynucleotide.

The construct of the invention is preferably a DNA/RNA hybrid strand which can be translocated through an MspA nanopore using a DNA helicase.

The construct may further comprise a barcoding section on the polynucleotide strand. Polynucleotide barcodes are well-known in the art (Kozarewa, I. et al., (2011), *Methods*

*Mol. Biol.* 733, p 279-298). A barcode is a specific sequence of polynucleotide that affects the current flowing through the pore in a specific and known manner. The barcoding section enables unambiguous identification of an analyte. Preferably the barcoding section is located between the leader sequence and the DNA helicase binding site.

An anchor e.g., a DNA anchor may be hybridised to the RNA polynucleotide or the non-RNA polynucleotide, as described above. The DNA anchor may further comprise spacers and cholesterol.

The RNA polynucleotide may be further extended using Poly (U) Polymerase. This ensures that the full length of the RNA is read.

The modified RNA polynucleotide may come in a variety of forms depending on which modification method(s) of the invention is used. Possible forms, include, but are not limited to, one or more of the following:
- an RNA polynucleotide chemically attached to a non-RNA polynucleotide e.g., using click chemistry
- an RNA polynucleotide ligated to a non-RNA polynucleotide
- an RNA polynucleotide hybridised to a non RNA leader sequence, with or without a bridging moiety
- an RNA polynucleotide hybridised to a cDNA sequence, with or without a bridging moiety
- an RNA polynucleotide attached to a non-RNA polynucleotide using a topoisomerase
- an RNA polynucleotide ligated to a non-RNA polynucleotide which has a region with reversed bases such that it runs in the opposite direction to the remainder of the non-RNA polynucleotide. Preferably the non-RNA polynucleotide is a DNA polynucleotide.

Kits

The invention also provides a kit for characterising a target RNA polynucleotide. The kit comprises a non-RNA polynucleotide which is adapted to attach to any target RNA polynucleotide for characterisation.

Preferably the non-RNA polynucleotide which is adapted to attach to any target RNA polynucleotide for characterisation has a reactive group attached, e.g., a click reactive group. The non-RNA polynucleotide with reactive group attached can ultimately be used by the end-user to react with any target RNA polynucleotide of choice to form a covalent bond. Preferably the target RNA polynucleotide also has a reactive group attached, e.g., a click reactive group which reacts with the reactive group attached to the non-RNA polynucleotide to form a covalent bond.

Alternatively the non-RNA polynucleotide which is adapted to attach to any target RNA polynucleotide for characterisation is provided with a ligase or is an oligonucleotide or primer which can be used by the end user to hybridise to any region of the target RNA polynucleotide of choice and act as a starting point for cDNA synthesis.

Alternatively the non-RNA polynucleotide which is adapted to attach to any target RNA polynucleotide for characterisation comprises a topoisomerase bound to a specific DNA polynucleotide. The topoisomerase bound DNA can ultimately be used by the end-user to attach the non-RNA (DNA) polynucleotide to any target RNA polynucleotide of choice. The end user can incubate the topoisomerase bound DNA with RNA which has a free 5' hydroxyl. The topoisomerase then joins the RNA to the DNA.

Alternatively the non-RNA polynucleotide which is adapted to attach to any target RNA polynucleotide for characterisation comprises a region with reversed bases (e.g A DNA region of reversed bases). This reversed region can be attached to the 5' ends of eukaryotic RNA which are modified by the addition of a 7-methylguanosine cap which runs in the opposite orientation.

Any of the embodiments discussed above with reference to the method of the invention equally apply to the kits. The kit may further comprise a DNA helicase binding protein which may be pre-bound to the non-RNA polynucleotide. The kit may further comprise a pore and the components of a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit typically comprises nucleotides. The kit preferably comprises dAMP, dTMP, dGMP and dCMP. The kit preferably does not comprise means to amplify and/or express polynucleotides.

The following Examples illustrate the invention.

Example 1

This example shows the sample preparation procedure which 1) extended the RNA region of an RNA/DNA strand, 2) annealed an anchor, 3) bound an enzyme and then 4) tested the resultant strand in an electrophysiology experiment. This example illustrated that it was possible to use a DNA helicase (T4 Dda-E94C/A360C (SEQ ID NO: 14 with mutations E94C/A360C and then (ΔM1)G1)) to control the movement of a synthetic DNA/RNA strand (DNA leader attached to an RNA strand, shown in FIG. 3) through an MspA nanopore.

Materials and Methods 1.1 Extension of the 3' End of an DNA/RNA Strand Using Poly(U) Polymerase The reagents listed in Table 3 below were mixed and incubated at 37° C. for 10 minutes. The mixture was then purified using Agencourt Ampure SPRI beads at a ratio of 1.8 μL SPRI beads per μL of sample. This sample was known as sample 1 (DNA/RNA 2).

Figure 4:
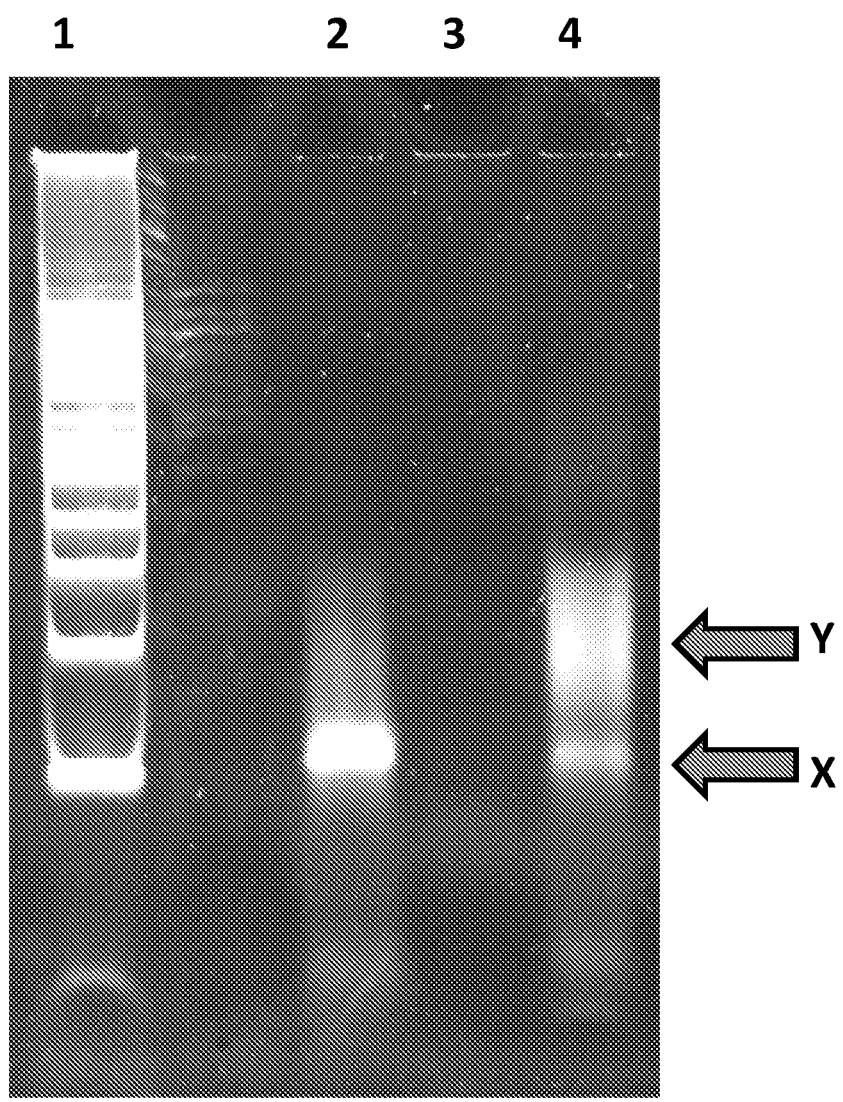
FIG. 4 shows a 5% PAGE TBE BioRad Criterion Gel (run at 140 V for 40 minutes) after the RNA poly(U) polymerase extension step (Example 1 step 1.1). Lane 1 shows a 100 bp TriDye™ ladder. Lane 2 shows synthetic DNA/RNA 1 (SEQ ID NO: 16 attached at its 3' end to four iSpC3 spacers which are attached at the opposite end to the 5' end of SEQ ID NO: 17) before polymerisation. Lane 3 shows the poly(U) polymerisation mix. Lane 4 shows the purified Sample 1 which contains poly(U) extended DNA/RNA 2. Arrow X corresponds to the non-extended DNA/RNA 1 and arrow Y corresponds to the poly(U) extended DNA/RNA 2.

FIG. 4 shows that the polymerase extension reaction was successful as a broad band labelled Y in the figure corresponded to variably extended DNA/RNA 1.

TABLE 3

| Reagent | Volume | Concentration of Stock | Final Concentration |
| --- | --- | --- | --- |
| Synthetic DNA/RNA 1 (SEQ ID NO: 16 attached at its 3' end to four iSpC3 spacers | 0.4 μl | 100 μM | 1 μM |

TABLE 3-continued

| Reagent | Volume | Concentration of Stock | Final Concentration |
|---|---|---|---|
| which are attached at the opposite end to the 5' end of SEQ ID NO: 17) | | | |
| rUTP | 0.4 µl | 100 mM | 1 mM |
| NEBuffer | 4 µl | 10 x | 1 x |
| PolyU Pol (NEB) | 2 µl | 2 U/µl | 4 U |
| NF H$_2$O | 33.2 µl | | |
| Total | 40 µl | | |

1.2 Anchor Anneal

The reagents listed in Table 4 below were mixed and incubated at 65° C. and then cooled to 4° C. at a rate of 0.1° C. per second. This sample was known as Sample 2.

TABLE 4

| Reagent | Volume | Concentration of Stock | Final Concentration |
|---|---|---|---|
| Sample 1 | 9 µl | ~1 µM | 942 µM |
| Anchor (SEQ ID NO: 18 attached at its 3' end to six iSp18 spacers, two thymines and a 3' cholesterol TEG) | 0.36 µl | 100 µM | 3.77 µM |
| 10 mM TRIS pH 7.5 50 mM NaCl | 0.19 µl | 50 x | 1 x |
| Total | 9.55 µl | | |

1.3 Bind DNA Helicase

Sample 2 (0.28 µL) was incubated with T4 Dda-E94C/A360C (0.36 µL, 3.8 µM, SEQ ID NO: 14 with mutations E94C/A360C and then (ΔM1)G1) in buffer (10 mM TRIS pH 7.5, 50 mM NaCl) at room temperature for one hour. This sample was known as Sample 3.

1.4 Electrophysiology

Sample 3 was diluted into buffer (1221 µL of 600 mM KCl, 50 mM HEPES pH 8.0, 463 mM glycerol). MgCl2 (13 µL, 1 M) and ATP (65 µL, 100 mM) were added to the sample 3 buffer mixture giving a total volume of 1300 µL.

Electrical measurements were acquired from single MspA nanopores inserted in block co-polymer in buffer (25 mM K Phosphate buffer, 150 mM Potassium Ferrocyanide, 150 mM Potassium Ferricyanide~pH 8.0). After achieving a single pore inserted in the block co-polymer, buffer (2 mL, 25 mM K Phosphate buffer, 150 mM Potassium Ferrocyanide, 150 mM Potassium Ferricyanide, pH 8.0) was flowed through the system to remove any excess MspA nanopores.

An excess of KCl buffer (600 mM KCl, 50 mM HEPES pH ~8, 463 mM glycerol) was flowed through the system and this KCl buffer was separated from an electrode buffer (25 mM K Phosphate buffer, 150 mM Potassium Ferrocyanide, 150 mM Potassium Ferricyanide, pH 8.0) by an agarose bridge.

The experiment was run at −120 mV and helicase-controlled DNA movement monitored.

Results

Figure 5:
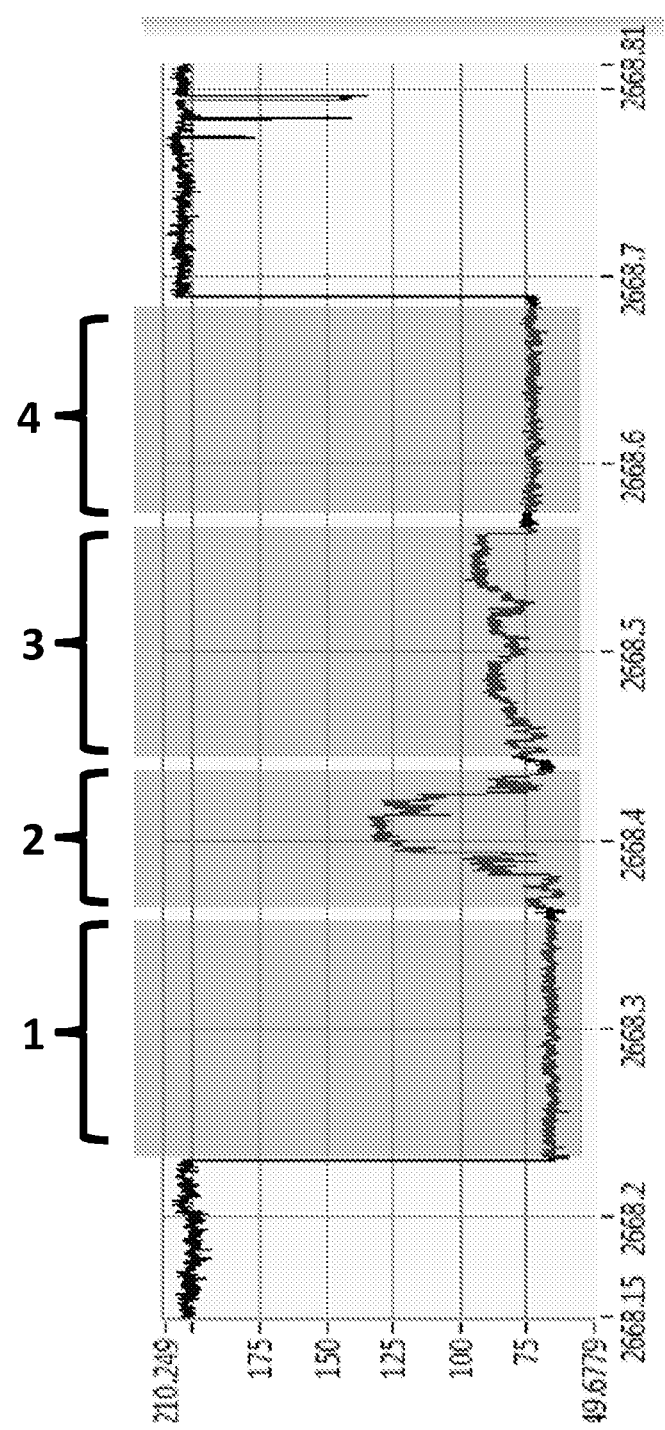
FIG. 5 shows an example trace of a helicase controlled DNA movement (y-axis=current (pA), x-axis=time (s)) where the DNA helicase (T4 Dda-E94C/A360C (SEQ ID NO: 14 with mutations E94C/A360C and then (ΔM1)G1)) controlled the movement of DNA/RNA 2 (cartoon representation shown in FIG. 3). Region 1 corresponds to the poly(dT) leader (SEQ ID NO: 16), region 2 corresponds to the iSpC3 spacers (the spacers allowed a larger amount of current to flow through the nanopore than the DNA or RNA regions), region 3 corresponds to the RNA sequence (SEQ ID NO: 17) and region 4 corresponds to the variable length poly(U) RNA region which was added in Example 1 step 1.1.

Helicase-controlled DNA movement was observed when Sample 3 (cartoon representation of the DNA/RNA 2 is shown in FIG. 3) was added to the nanopore system. An example of helicase controlled DNA movement for Sample 3 is shown in FIG. 5. The various regions of the synthetic strand were identified as the strand translocated through the nanopore (region 1=poly(dT) leader (SEQ ID NO: 16), region 2=iSpC3 spacers, region 3=RNA sequence (SEQ ID NO: 17) and region 4=the variable length poly(U) RNA). This example showed that it was possible to use a DNA helicase to control the movement of a DNA/RNA strand (cartoon representation shown in FIG. 3) through an MspA nanopore. The Poly (U) Polymerase extension step ensured that the full length of the RNA was read.

Example 2

This example shows the ligation of a DNA strand (SEQ ID NO: 21) to an RNA strand (SEQ ID NO: 19) using T4 DNA ligase.

Materials and Methods 2.1 Ligation of a DNA Strand to an RNA Strand Using T4 DNA Ligase The reagents listed in Table 5 below were mixed and placed on a thermocycler. The thermocycler was set to the program in Table 6 below. The samples were then analysed using a 10% PAGE TBE-Urea denaturing BioRad Criterion Gel which was run at 140 V for 60 minutes.

TABLE 5

| Reagent | Volume | Stock Concentration | Final Concentration |
|---|---|---|---|
| 5' phosphate RNA (SEQ ID NO: 19) | 0.3 ul | 50 uM | 1 uM |
| T4 DNA ligase buffer | 1.5 | 10 x | 1 x |
| T4 DNA ligase | 1 ul | 10 U/ul | 10 U |
| DNA splint (SEQ ID NO: 20) | 0.3 ul | 50 uM | 1 uM |
| Cy3 DNA (SEQ ID NO: 21) | 0.6 ul | 50 uM | 2 uM |
| ATP | 0.3 ul | 50 mM | 1 mM |
| NF H$_2$O | 11 ul | | |
| Total | 15 ul | | |

TABLE 6

| Number of Cycles | Step | Temp (° C.) | Time |
|---|---|---|---|
| 1 | Ligate | 25 | 1:00:00 |
| 1 | Denature | 65 | 0:10:00 |

Results

Figure 8:
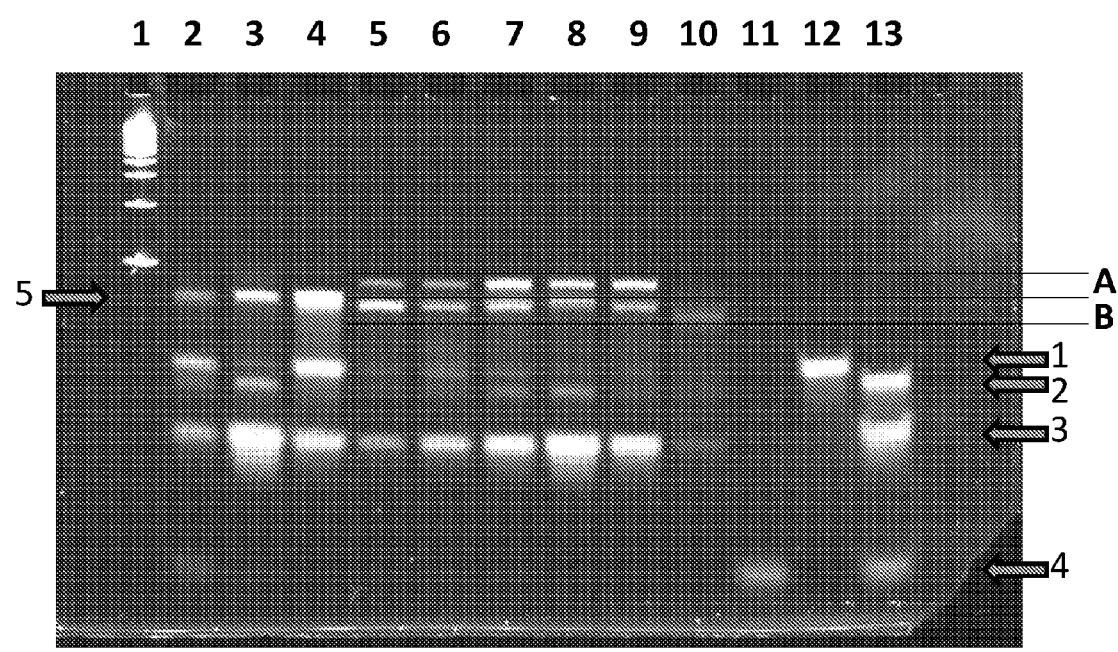
FIG. 8 shows a 10% PAGE TBE-Urea denaturing criterion gel run at 140 V for 60 minutes which includes samples from Example 2. Lane 1 shows a 100 bp TriDye™ ladder. Lane 2 shows the DNA oligo 1 (1× concentration, SEQ ID NO: 21), the RNA oligo 1 (1× concentration, SEQ ID NO: 19) and the DNA splint (0.5× concentration, SEQ ID NO: 20) after they have undergone the ligation reaction described in Example 2 in the absence of T4 DNA ligase. Lane 3 shows the DNA oligo 1 (1× concentration, SEQ ID NO: 21), the RNA oligo 1 (1× concentration, SEQ ID NO: 19) and the DNA splint (4× concentration, SEQ ID NO: 20) after they have undergone the ligation reaction described in Example 2 in the absence of T4 DNA ligase. Lane 4 shows unreacted DNA oligo 1 (SEQ ID NO: 21) and the DNA splint (SEQ ID NO: 20) mixed together as a control. Lane 5 shows the DNA oligo 1 (1× concentration, SEQ ID NO: 21), the RNA oligo 1 (1× concentration, SEQ ID NO: 19) and the DNA splint (0.5× concentration, SEQ ID NO: 20) after they have undergone the ligation reaction described in Example 2 in the presence of T4 DNA ligase. Lane 6 shows the DNA oligo 1 (1× concentration, SEQ ID NO: 21), the RNA oligo 1 (1× concentration, SEQ ID NO: 19) and the DNA splint (1× concentration, SEQ ID NO: 20) after they have undergone the ligation reaction described in Example 2 in the presence of T4 DNA ligase. Lane 7 shows the DNA oligo 1 (1× concentration, SEQ ID NO: 21), the RNA oligo 1 (1× concentration, SEQ ID NO: 19) and the DNA splint (2× concentration, SEQ ID NO: 20) after they have undergone the ligation reaction described in Example 2 in the presence of T4 DNA ligase. Lane 8 shows the DNA oligo 1 (1× concentration, SEQ ID NO: 21), the RNA oligo 1 (1× concentration, SEQ ID NO: 19) and the DNA splint (4× concentration, SEQ ID NO: 20) after they have undergone the ligation reaction described in Example 2 in the presence of T4 DNA ligase. Lane 9 shows the DNA oligo 1 (1× concentration, SEQ ID NO: 21), the RNA oligo 1 (1× concentration, SEQ ID NO: 19) and the DNA splint (0.5× concentration, SEQ ID NO: 20) after they have undergone the ligation reaction described in Example 2 in the presence of T4 DNA ligase and they have been incubated with further DNA splint (4.5× concentration of SEQ ID NO: 20) after the ligation step. Lane 10 shows the DNA oligo 1 (1× concentration, SEQ ID NO: 21), the RNA oligo 1 (1× concentration, SEQ ID NO: 19) and the DNA splint (1× concentration, SEQ ID NO: 20) after they have undergone the ligation reaction described in Example 2 in the presence of T4 DNA ligase and they have been further heat treated and exposed to ExoI. Lane 11 shows the DNA oligo 1 (SEQ ID NO: 21) as a control. Lane 12 shows the RNA oligo 1 as a control. Lane 13 shows unreacted RNA oligo 1 (SEQ ID NO: 19) and the DNA splint (SEQ ID NO: 20) mixed together as a control. The band labelled 1 corresponds to RNA oligo 1 (SEQ ID NO: 19). The band labelled 2 corresponds to RNA oligo 1 (SEQ ID NO: 19) hybridised to the splint (SEQ ID NO: 20). The band labelled 3 corresponds to the splint (SEQ ID NO: 20). The band labelled 4 corresponds to the DNA oligo 1 (SEQ ID NO: 21). The band labelled 5 corresponds to DNA oligo 1 (SEQ ID NO: 21) hybridised to the splint (SEQ ID NO: 20). The region labelled A corresponds to the ligated substrate in the presence of the splint (DNA oligo 1 ligated to RNA oligo 1, hybridised to splint). The region labelled B corresponds to the ligated substrate in the absence of the splint (DNA oligo 1 ligated to RNA oligo 1).

The TBE-Urea denaturing gel was used to analyse the ligation of CY®3 DNA (SEQ ID NO: 21) to RNA (SEQ ID NO: 19). FIG. 8, lanes 2-3 showed the control reactions of the ligation step with increasing concentration of the DNA splint (SEQ ID NO: 20) in the absence of T4 DNA ligase. For these control reactions no bands in regions A and B were observed indicating that no ligation reaction occurred under these conditions. Lanes 5-8 showed the ligation step with increasing concentrations of the DNA splint (SEQ ID NO: 20) in the presence of T4 DNA ligase. For all of lanes 5-8 a band was visible in both region A and region B which corresponded to ligated substrate with the hybridised DNA splint (A) and the ligated substrate without the hybridised DNA splint (B). As the concentration of splint was increased the intensity of band A also increased. Two further control reactions were carried out shown in lanes 9 and 10. Lane 9 corresponded to the same sample as shown in lane 5 which was further treated with the addition of extra DNA splint (4.5×) added after the ligation step. This showed the expected increase in intensity of the upper band (corresponding to ligated product with the splint hybridised) and decrease in intensity of the lower band B (corresponding to ligated product without the splint hybridised) when compared to lane 5. Lane 10 corresponded to the same sample as shown in lane 6 that was further treated with ExoI at 37° C. for 30 minutes. Heating during ExoI treatment resulted in the separation of the ligated strand and the DNA splint. The DNA splint was preferentially digested by ExoI because it had a 3' DNA end. This resulted in the disappearance of the band in region A which corresponded to the ligated product hybridised to the DNA splint, as the DNA splint was digested by the ExoI. The band in region B was still visible after digestion with ExoI. This meant that the ligation step had been successful because if the DNA had not been ligated to the RNA then the DNA that had not ligated would have been digested by the ExoI and no band would have been visible in region B. Therefore, this example showed that it was possible to ligate DNA to RNA using a T4 DNA ligase.

Example 3

Figure 10:
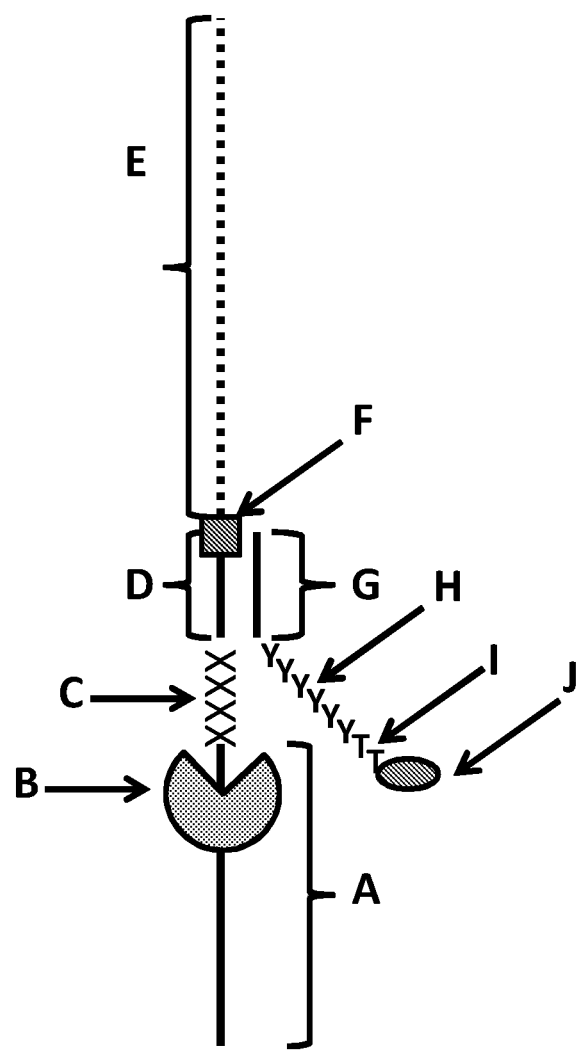
FIG. 10 shows a cartoon representation of the DNA/RNA strand produced in Example 3A which is translocated through an MspA nanopore using a DNA helicase (T4 Dda-E94C/A360C (SEQ ID NO: 14 with mutations E94C/A360C and then (ΔM1)G1)). Region A corresponds to the DNA leader (SEQ ID NO: 22) to which the DNA helicase (labelled B) binds. Region A is attached to four iSp18 spacers (shown as X's and labelled C). Region D corresponds to a second DNA sequence (SEQ ID NO: 23). Region E corresponds to the firefly luciferase mRNA with a 5'-hexynl-G region (RNA X1, mRNA with an open reading frame of SEQ ID NO: 26 which has a 5'-hexynl-G as the 5' most nucleotide and has a 3' polyA tail). Regions D and E are attached by click chemistry. The reacted azide and hexynl groups are represented by a box (labelled F). Region G is the DNA (SEQ ID NO: 18) which is hybridised to Region D. Attached to the DNA (SEQ ID NO: 18) is six iSp18 spacers (shown as Y's and labelled H) two thymines (shown as T's and labeled I) and a 3' cholesterol TEG (labelled J).

This example shows a sample preparation procedure that chemically attached a DNA strand to an RNA strand using click chemistry. This was carried out on two different samples one of which had a fluorescent group attached to the DNA, in order for the chemical attachment step to be confirmed using gel electrophoresis. The DNA/RNA strand that did not have a fluorescent group attached was then tested in an electrophysiology experiment. This example illustrated that it was possible to use a DNA helicase (T4 Dda-E94C/A360C (SEQ ID NO: 14 with mutations E94C/A360C and then (ΔM1)G1)) to control the movement of an RNA strand that was attached to a non-RNA polynucleotide by copper-mediated click-chemistry (cartoon representation of the construct is shown in FIG. 10) through an MspA or Lysenin nanopore.

Materials and Methods 3A.1 Click Reaction of DNA X1 to RNA X1

The RNA X1, DNA X1 and splint X1 (listed in Table 7 below) were mixed in buffer (TRIS-NaCl (500 mM-2.5M) pH 8). The DNA X1, RNA X1 and splint X1 were annealed in a PCR machine (protocol heat to 55° C. and cool to 4° C. at 0.1° C./s). CuSO4, Tris(3-hydroxypropyltriazolylmethylamine) and sodium ascorbate (Sigma A4034) were then added to the DNA X1/RNA X1 splint X1 mixture and the sample was then placed on a thermocycler. The thermocycler was set to the program in Table 8 below. The sample was then purified using Agencourt Ampure SPRI beads at a ratio of 1.8 µl SPRI beads per L of sample. This sample was known as sample 3A (DNA/RNA 3A). This sample was then analysed on a 5% PAGE TBE BioRad Criterion Gel and in electrophysiology as described in 3.3 below.

TABLE 7

| Reagent | Volume | Stock Concentration | Final Concentration |
|---|---|---|---|
| Firefly luciferase mRNA (RNA X1, mRNA with an open reading frame of SEQ ID NO: 26 which has a 5'-hexynl-G as the 5' most nucleotide and has a 3' polyA tail) from Trilink Biotech, CA | 12.9 ul | 1.1 uM | 0.94 uM |
| DNA with Azide (DNA X1, SEQ ID NO: 22 attached at its 3' end to four iSp18 spacers attached at their opposite end to the 5' end of SEQ ID NO: 23 which has a 3AzideN attached to the 3' end) | 0.3 ul | 50 uM | 1 uM |
| Splint X1 (SEQ ID NO: 24) | 0.6 ul | 50 uM | 2 uM |
| CuSO$_4$ | 0.3 ul | 50 mM | 1 mM |
| Tris(3-hydroxypropyltriazolylmethylamine) | 0.3 ul | 100 mM | 2 mM |
| Sodium Ascorbate (Sigma A4034) | 0.3 ul | 200 mM | 4 mM |
| TRIS-NaCl (500 mM-2.5M) pH 8 | 0.3 ul | 500 mM | 10 mM |
| Total | 15 ul | | |

TABLE 8

| Number of Cycles | Step | Temp (° C.) | Time |
|---|---|---|---|
| 1 | Click | 23 | 0:30:00 |
| 1 | Click | 37 | 0:30:00 |

3B.1 Click Reaction of DNA X2 to RNA X1

The RNA X1, DNA X2 and splint X1 (listed in Table 9 below) were mixed in buffer (TRIS or MOPS (500 mM-2.5M) pH 6.8-7). The DNA X2, RNA X1 and splint X1 were annealed in a PCR machine (protocol heat to 55° C. and cool to 4° C. at 0.1° C./s). CuSO4, Tris(3-hydroxypropyltriazolylmethylamine) and sodium ascorbate (Sigma A4034) were then added to the DNA X2/RNA X1/splint X1 mixture and the sample was then placed on a thermocycler. The thermocycler was set to the program in Table 10 below. The sample was then purified using Agencourt Ampure SPRI beads at a ratio of 1.8 µl SPRI beads per µL of sample.

This sample was known as sample 3B (DNA/RNA 3B). This sample was then analysed on a 5% PAGE TBE BioRad Criterion Gel.

TABLE 9

| Reagent | Volume | Stock Concentration | Final Concentration |
|---|---|---|---|
| Firefly luciferase mRNA with a 5'-hexynl-G (RNA X1, mRNA with an open reading frame of SEQ ID NO: 26 which has a 5'-hexynl-G as the 5' most nucleotide and has a 3' polyA tail | 12.9 ul | 1.1 uM | 0.94 uM |
| Cy3 DNA with Azide (DNA X2, SEQ ID NO: 25 which had a Cy3 attached to its 5' end and had a 3AzideN attached to the 3' end) | 0.3 ul | 50 uM | 1 uM |
| Splint X1 (SEQ ID NO: 24) | 0.6 ul | 50 uM | 2 uM |
| CuSO4 | 0.3 ul | 50 mM | 1 mM |
| Cu Ligand | 0.3 ul | 100 mM | 2 mM |
| Sodium Ascorbate (Sigma A4034) | 0.3 ul | 200 mM | 4 mM |
| TRIS-NaCl (500 mM-2.5M) pH 8 | 0.3 ul | 500 mM | 10 mM |
| Total | 15 ul | | |

TABLE 10

| Number of Cycles | Step | Temp (° C.) | Time |
|---|---|---|---|
| 1 | Click | 23 | 0:30:00 |
| 1 | Click | 37 | 0:30:00 |

3.3 Electrophysiology

Tether was annealed to Sample 3A as per Example 1 (see section 1.2). Sample 3A (0.28 µl) and T4 Dda-E94C/A360C (0.36 µl, 3.8 µM), SEQ ID NO: 14 with mutations E94C/A360C and then (ΔM1)G1) were diluted into buffer (1221 µL of 500 mM KCl, 25 mM potassium phosphate pH 8.0). MgCl2 (13 µL, 1 M) and ATP (65µL, 100 mM) were added to the sample 3A buffer mixture giving a total volume of 1300 µL.

Electrical measurements were acquired from single MspA or Lysenin nanopores inserted in block co-polymer in buffer (25 mM K Phosphate buffer, 150 mM Potassium Ferrocyanide, 150 mM Potassium Ferricyanide~pH 8.0). After achieving a single pore inserted in the block co-polymer, then buffer (2 mL, 25 mM K Phosphate buffer, 150 mM Potassium Ferrocyanide, 150 mM Potassium Ferricyanide, pH 8.0) was flowed through the system to remove any excess MspA or Lysenin nanopores.

An excess of buffer (500 mM KCl, 25 mM potassium phosphate pH 8.0) was flowed through the system prior to the addition of sample. Finally, T4 Dda-E94C/A360C bound to sample 3A was then added to the nanopore system, the experiment was run at −120 mV and helicase-controlled DNA movement monitored.

Results

Figure 9:
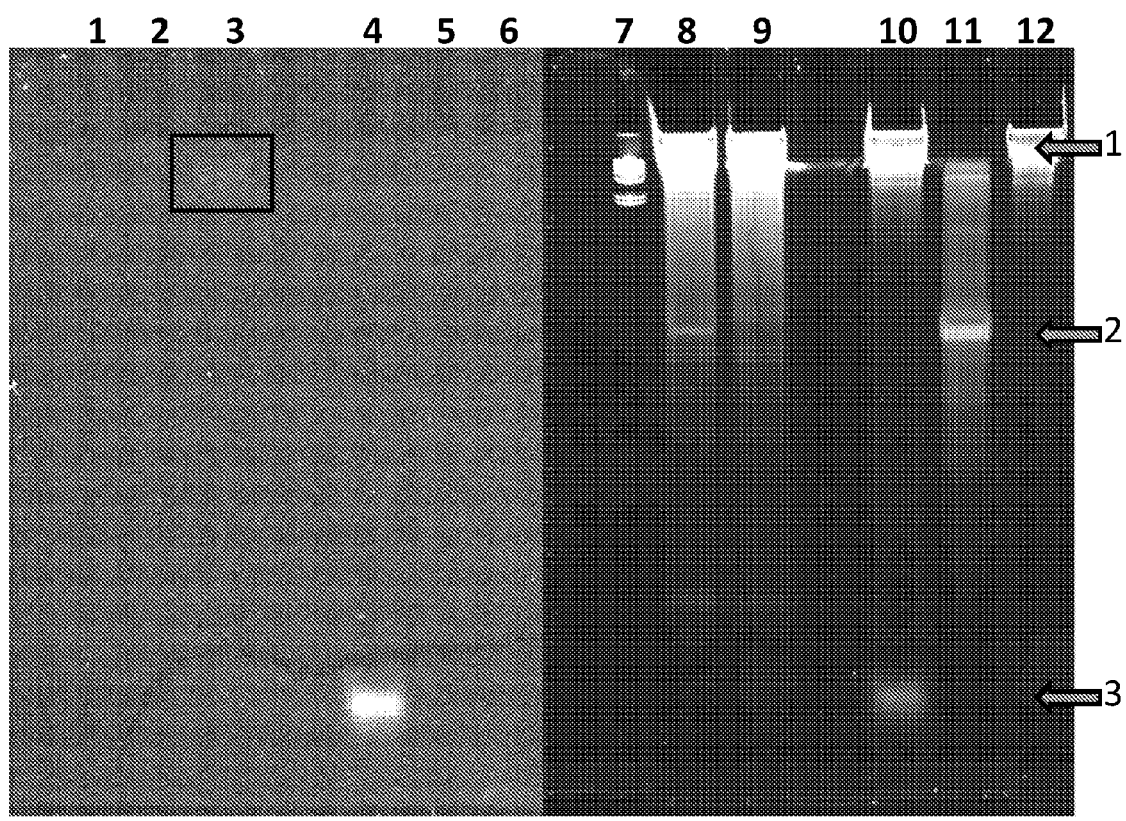
FIG. 9 shows a 5% PAGE TBE BioRad Criterion Gel run at 140 mV for 60 minutes, (A) before SYBR stain and (B) after SYBR stain, which includes samples from Example 3. Lanes 1 and 7 show a TriDye™ 1 kB ladder. Lanes 2 and 8 show the product produced from Example 3A (DNA X1 (SEQ ID NO: 22 attached at its 3' end to four iSp18 spacers attached at their opposite end to the 5' end of SEQ ID NO: 23 which has a 3AzideN attached to the 3' end) reacted with firefly luciferase mRNA with a 5'-hexynl-G (RNA X1, mRNA with an open reading frame of SEQ ID NO: 26 which has a 5'-hexynl-G as the 5' most nucleotide and has a 3' polyA tail) in the presence of DNA splint X1 (SEQ ID NO: 24)). Lanes 3 and 9 show the product produced from Example 3B (DNA X2 (SEQ ID NO: 25 which had a CY®3 attached to its 5' end and had a 3AzideN attached to the 3' end) reacted with firefly luciferase mRNA with a 5'-hexynl-G (RNA X1, mRNA with an open reading frame of SEQ ID NO: 26 which has a 5'-hexynl-G as the 5' most nucleotide and has a 3' polyA tail) in the presence of DNA splint X1 (SEQ ID NO: 24)). Lanes 4 and 10 show DNA X2 (SEQ ID NO: 25 which had a CY®3 attached to its 5' end and had a 3AzideN attached to the 3' end) mixed with firefly luciferase mRNA with a 5'-hexynl-G (RNA X1, mRNA with an open reading frame of SEQ ID NO: 26 which has a 5'-hexynl-G as the 5' most nucleotide and has a 3' polyA tail). Lanes 5 and 11 show DNA X1 (SEQ ID NO: 22 attached at its 3' end to four iSp18 spacers attached at their opposite end to the 5' end of SEQ ID NO: 23 which has a 3AzideN attached to the 3' end). Lanes 6 and 12 show firefly luciferase mRNA with a 5'-hexynl-G (RNA X1, mRNA with an open reading frame of SEQ ID NO: 26 which has a 5'-hexynl-G as the 5' most nucleotide and has a 3' polyA tail). The band labelled 1 corresponds to RNA X1 with and without DNA attached. Band 2 corresponds to unreacted DNA X1 (SEQ ID NO: 22 attached at its 3' end to four iSp18 spacers attached at their opposite end to the 5' end of SEQ ID NO: 23 which has a 3AzideN attached to the 3' end). Band 3 corresponds to unreacted DNA X2 (SEQ ID NO: 25 which had a CY®3 attached to its 5' end and had a 3AzideN attached to the 3' end). Only DNA which contained the CY®3 label was visible on the non-SYBR stained gel.

A TBE-Urea denaturing gel was used to analyse the click reaction of DNA (either DNA X1 (Example 3A, SEQ ID NO: 22 attached at its 3' end to four iSp18 spacers attached at their opposite end to the 5' end of SEQ ID NO: 23 which has a 3AzideN attached to the 3' end) or DNA X2 (Example 3B, SEQ ID NO: 25 which had a CY®3 attached to its 5' end and had a 3AzideN attached to the 3' end)) to RNA X1. The DNA that was used in Example 3B was visible before the SYBR stain owing to the Cy®3 group which was attached. FIG. 9, lanes 3 and 9 showed the sample produced after example 3B's click reaction. The fluorescent band at the top of lane 3 (highlighted by a white box in FIG. 9) showed that the DNA with the Cy®3 label had been attached to the mRNA (the fluorescent band for the DNA-only was at arrow 3 and the DNA bound to mRNA was at arrow 1). Lanes 2 and 8 showed the sample produced after the click reaction in Example 3A (no fluorescent group on the DNA). The band in lane 11 corresponded to unreacted DNA (arrow 2) and the DNA bound to mRNA was arrow 1. Therefore, this gel showed that the click reaction was successful at joining DNA (with a fluorescent label (X1) or without a fluorescent label (X2)) to mRNA (RNA X1).

Helicase-controlled RNA movement was observed when Sample 3A (cartoon representation of the DNA/RNA 3A is shown in FIG. 10) was added to the nanopore system. An example of helicase controlled RNA movement through MspA is shown in FIG. 11 (regions 2, 3 and 4) and movement through a Lysenin mutant in FIG. 21. The various regions of the strand in FIG. 11 were identified as the strand translocated through the nanopore. Taken together, regions 2, 3 and 4 represent the DNA leader reacted to the target RNA by click reaction (Region 2=SEQ ID NO: 22 joined to four iSp18 spacers; Region 3=SEQ ID NO: 23; Region 4=Firefly luciferase mRNA with open reading frame SEQ ID NO:26 and the arrow marked with * highlights the linkage formed by the click reaction). Region 1 shows a separate nanopore translocation of a DNA leader not reacted to RNA (SEQ ID NO: 22 joined to four iSp18 spacers joined to SEQ ID NO:23). Similar features can be identified for the Lysenin trace in FIG. 21. This example showed that it was possible to use a DNA helicase to control the movement of a long mRNA strand through a nanopore by linking a non-RNA polynucleotide (SEQ ID NO: 22 joined to four iSp18 spacers joined to SEQ ID NO:23) to the long mRNA strand, (cartoon representation shown in FIG. 10) through an MspA or Lysenin nanopore.

Example 4

This example shows ligation of hairpin-forming oligos (3T hairpin=SEQ ID NO: 29 is attached at its 5' end to a phosphate group and is attached at its 3' end to four iSpC3 spacers which are attached at the opposite end to the 5' end of SEQ ID NO: 27, or the 10T hairpin=SEQ ID NO: 29 is attached at its 5' end to a phosphate group and is attached at its 3' end to four iSpC3 spacers which are attached at the opposite end to the 5' end of SEQ ID NO: 28) to the 3' end of an RNA strand (SEQ ID NO: 30) using T4 DNA ligase and subsequent reverse-transcription from the 3' end of the hairpin-forming oligo. This ligation and reverse-transcription demonstrated a method of constructing a RNA/cDNA construct (see FIG. 13).

A poly T overhang at the 3' end of the hairpin-forming oligos (either the 3T or 10T hairpins) hybridizes to the poly A-tail of the mRNA and acts as a splint for efficient DNA to RNA ligation. The hairpin can act as a primer for subsequent reverse-transcription.

Materials and Methods

The reagents listed in Table 11 below were mixed and placed on a thermocycler. The thermocycler was set to the program in Table 12 below. The mixture was then purified using Agencourt Ampure SPRI beads at a ratio of 1.8 μL SPRI beads per μL of sample. After purification, reverse transcription was performed using Life Technologies Super Script II: reagents in Table 13 were mixed according to the manufacturer's protocol and placed on a thermocycler set to the program in Table 14. Samples were then analysed using a 10% PAGE TBE-Urea denaturing BioRad Criterion Gel which was run at 140 V for 60 minutes.

TABLE 11

| Reagent | Volume | Stock Concentration | Final Concentration |
| --- | --- | --- | --- |
| RNA strand (SEQ ID NO: 30) | 0.72 ul | 556 ng/ul | 0.2 uM |
| polyT hairpin (3T hairpin or 10T hairpin described above) | 0.4 ul | 50 uM | 1 uM |
| T4 DNA ligase buffer | 4 ul | 5 x | 1 x |
| T4 DNA ligase | 1 ul | 2000 U | 2000 U |
| NF H$_2$O | 13.88 ul | | |
| Total | 20 ul | | |

TABLE 12

| Number of Cycles | Step | Temp (° C.) | Time |
| --- | --- | --- | --- |
| 1 | Ligate | 16 | 2:00:00 |

TABLE 13

| Reagent | Volume | Stock Concentration | Final Concentration |
| --- | --- | --- | --- |
| RNA after polyT hairpin ligation | 7 ul | 35.5 ng/ul | 248.5 ng/reaction |
| dNTPs | 1 ul | 10 uM each | 0.5 uM |
| NF H$_2$O | 5 ul | | |
| First-Strand Buffer | 4 ul | 5x | 1x |
| 0.1M DTT | 2 ul | 0.1M | 0.01M |
| Super Script II | 1 ul | 200 U | 200 U |
| Total | 20 ul | | |

TABLE 14

| Number of Cycles | Step | Temp (° C.) | Time |
| --- | --- | --- | --- |
| 1 | Reverse Transcription | 42 | 0:50:00 |
| 2 | Denaturation | 70 | 0:15:00 |

Results

A TBE-Urea denaturing gel (see FIG. 14) was used to analyse the 3T and 10T hairpin ligation and reverse transcription. In lane 5, partial ligation of the 3T-hairpin was visible in the form of an upward shift of the RNA strand band (SEQ ID NO: 30, the RNA strand is labelled as band A in FIG. 14). After reverse transcription (Lane 6) the band was shifted below the level of the RNA strand (SEQ ID NO: 30, band A in FIG. 14) due to the fact that the double stranded construct of RNA/cDNA (shown in FIG. 13) migrated faster than the single stranded RNA (SEQ ID NO: 30 shown as band A in FIG. 14). In the lane 7, ligation of the 10T hairpin occurred with nearly 100% efficiency and was visible as a single band above the level of single stranded RNA strand (SEQ ID NO: 30 shown as band A in FIG. 14). Lane 8 shows the sample after reverse transcription, primed by the 10T hairpin, where the ligated and reverse transcribed product was shifted downwards below the single stranded RNA band (SEQ ID NO: 30 shown as band A in FIG. 14). A hybridization control sample in lane 9 (reaction mixture without T4 DNA ligase) was visible at the level of single stranded RNA (SEQ ID NO: 30 shown as band A in FIG. 14) and showed that a shift was observed only for the ligated product.

Example 5

This example shows how an RNA/cDNA construct was analysed in an electrophysiology experiment. To obtain the RNA/cDNA construct the 10T hairpin (SEQ ID NO: 29 is attached at its 5' end to a phosphate group and is attached at its 3' end to four iSpC3 spacers which are attached at the opposite end to the 5' end of SEQ ID NO: 28) was ligated to the 3' end of firefly luciferase mRNA (RNA X1, mRNA with an open reading frame of SEQ ID NO: 26 which has a 5'-hexynl-G as the 5' most nucleotide and has a 3' polyA tail). Prior to the ligation, click chemistry was used to attach DNA with Azide (DNA X1, SEQ ID NO: 22 attached at its 3' end to four iSp18 spacers attached at their opposite end to the 5' end of SEQ ID NO: 23 which has a 3AzideN attached to the 3' end) to the 5' end of Firefly luciferase mRNA with a 5'-hexynl-G (RNA X1, mRNA with an open reading frame of SEQ ID NO: 26 which has a 5'-hexynl-G as the 5' most nucleotide and has a 3' polyA tail) as described in Example 3. After hairpin ligation reverse transcription was performed.

Materials and Methods

Click Reaction

The RNA of Firefly luciferase mRNA with a 5'-hexynl-G (RNA X1, mRNA with an open reading frame of SEQ ID NO: 26 which has a 5'-hexynl-G as the 5' most nucleotide and has a 3' polyA tail) was ligated to DNA with Azide (DNA X1, SEQ ID NO: 22 attached at its 3' end to four iSp18 spacers attached at their opposite end to the 5' end of SEQ ID NO: 23 which has a 3AzideN attached to the 3' end) as described in Example 3B click reaction. This sample was known as Sample 3B.

Hairpin Ligation and RT

The sample 3B (DNA/RNA 3B) was then ligated to the 10T hairpin and reverse transcribed as described in Example 4. The volumes and quantities of reagents are shown in Tables 15 and 17 below and the thermocycle conditions in tables 16 and 18. The sample produced after ligation/reverse transcription was known as sample 5B. A cartoon representation of the sample construct is shown in FIG. 15.

TABLE 15

| Reagent | Volume | Stock Concentration | Final Concentration |
| --- | --- | --- | --- |
| Sample 3B | 10 ul | 22 ng/ul | 0.017 uM |
| polyT hairpin (3T hairpin or 10T hairpin described above) | 0.4 ul | 50 uM | 1 uM |

TABLE 15-continued

| Reagent | Volume | Stock Concentration | Final Concentration |
|---|---|---|---|
| T4 DNA ligase buffer | 4 ul | 5 x | 1 x |
| T4 DNA ligase | 1 ul | 2000 U/ul | 2000 U |
| NF H$_2$O | 4.6 ul | | |
| Total | 20 ul | | |

TABLE 16

| Number of Cycles | Step | Temp (° C.) | Time |
|---|---|---|---|
| 1 | Ligate | 16 | 2:00:00 |

TABLE 17

| Reagent | Volume | Stock Concentration | Final Concentration |
|---|---|---|---|
| Sample 3B after reverse transcription | 12 ul | 20 ng/ul | 240 ng/reaction |
| dNTPs | 1 ul | 10 uM each | 0.5 uM |
| First-Strand Buffer | 4 ul | 5x | 1x |
| 0.1M DTT | 2 ul | 0.1M | 0.01M |
| Super Script II | 1 ul | 200 U/ul | 200 U |
| Total | 20 ul | | |

TABLE 18

| Number of Cycles | Step | Temp (° C.) | Time |
|---|---|---|---|
| 1 | Reverse Transcription | 42 | 0:50:00 |
| 2 | Denaturation | 70 | 0:15:00 |

Electrophysiology

A tether was annealed to Sample 5B as described in Example 1 (see section 1.2). Sample 5B (4 µl) and (T4 Dda-E94C/C109A/C136A/A360C (0.36 µl, 3.8 µM, SEQ ID NO: 14 with mutations E94C/C109A/C136A/A360C and then (ΔM1)G1) were diluted into buffer (1221 µL of 500 mM KCl, 25 mM potassium phosphate pH 8.0). MgCl2 (13 µL, 1 M) and ATP (65 µL, 100 mM) were added to the sample 5B (DNA/RNA/cDNA 5B) buffer mixture giving a total volume of 1300 µL.

Electrical measurements were acquired from single MspA or CsgG-Eco-(Y51T/F56Q)-StrepII(C))9 (SEQ ID NO: 44 with mutations Y51T/F56Q where StepII(C) is SEQ ID NO: 45 and is attached at the C-terminus) nanopores inserted in block co-polymer in buffer (25 mM K Phosphate buffer, 150 mM Potassium Ferrocyanide, 150 mM Potassium Ferricyanide~pH 8.0). After achieving a single pore inserted in the block co-polymer, then buffer (2 mL, 25 mM K Phosphate buffer, 150 mM Potassium Ferrocyanide, 150 mM Potassium Ferricyanide, pH 8.0) was flowed through the system to remove any excess MspA or CsgG nanopores.

An excess of buffer (500 mM KCl, 25 mM potassium phosphate pH 8.0) was flowed through the system prior to the addition of sample. Finally, (T4 Dda-E94C/C109A/C136A/A360C bound to sample 5B (DNA/RNA/cDNA 5B) was then added to the nanopore system, the experiment was run at −140 mV and helicase-controlled DNA movement monitored.

Results

Helicase-controlled DNA/RNA/cDNA movement was observed when Sample 5B was added to the nanopore system. An example of a helicase-controlled DNA/RNA/cDNA movement event is shown in FIG. 16 (regions 1-5) for MspA or FIG. 22 for CsgG. The various regions of the strand in FIG. 16 were identified as the strand translocated through the nanopore; Region 1 represented the non-RNA polynucleotide reacted to the target RNA by click reaction; Region 2=Firefly luciferase mRNA; Region 3=the iSpC3 spacers present in the 10T hairpin which was ligated to the mRNA; Region 4=the polyT region of the 10T hairpin which was ligated to the mRNA; Region 5=the cDNA which was produced by reverse transcription of the mRNA. Similar features can be identified in the CsgG trace in FIG. 22. This example showed that it was possible to use a DNA helicase to control the movement of a strand DNA RNA cDNA (formed by linking a DNA strand to an mRNA strand, ligating a hairpin to that mRNA strand and using the hairpin to reverse transcribe the mRNA) (cartoon representation shown in FIG. 15) through an MspA or CsgG nanopore.

Example 6

This example shows how a non-RNA polynucleotide can be attached to an RNA strand that has a 5' methylguanosine cap (homologous to some native cellular mRNAs) by removing the cap before ligation. In this case, a capped RNA strand (SEQ ID NO: 30 which has a 7-methylguanosine cap connected to the 5' end of the strand by a 5' to 5' triphosphate linkage) was used, which was then decapped using RNA 5' pyrophosphohydrolase (RppH) and subsequently ligated to a non-RNA polynucleotide (30 SpC3 spacers attached to the 5' end of SEQ ID NO: 31 which was attached at the 3' end to four iSp18 spacers which were attached at the opposite end to the 5' end of SEQ ID NO: 32 which was attached at the 3' end to four 5-nitroindoles which were attached at the opposite end to the RNA sequence CAAGGG) using T4 RNA ligase 1.

Materials and Methods

In order to ligate a non-RNA polynucleotide to the 5' end of the capped RNA strand (SEQ ID NO: 30 which has a 7-methylguanosine cap connected to the 5' end of the strand by a 5' to 5' triphosphate linkage) the mRNA was first decapped using RppH as a decapping enzyme. The reagents listed in Table 19 were mixed and the reaction mixture was then placed on a thermocycler set to the program in Table 20. The resulting reaction mixture was then purified using Agencourt Ampure SPRI beads at a ratio of 1.8 µL SPRI beads per µL of sample. Subsequently, a non-RNA polynucleotide (30 SpC3 spacers attached to the 5' end of SEQ ID NO: 31 which was attached at the 3' end to four iSp18 spacers which were attached at the opposite end to the 5' end of SEQ ID NO: 32 which was attached at the 3' end to four 5-nitroindoles which were attached at the opposite end to the RNA sequence CAAGGG) was ligated to the RNA by mixing the reagents listed in a Table 21 and placing the mixture on a thermocycler set to the program in Table 22. The reaction mixture was then analysed using a 5% PAGE TBE-Urea denaturing BioRad Criterion Gel which was run at 140 V for 60 minutes.

TABLE 19

| Reagent | Volume | Stock Concentration | Final Concentration |
|---|---|---|---|
| Capped RNA strand (SEQ ID NO: 30 which has a 7-methylguanosine cap connected to the 5' end of the strand by a 5' to 5' triphosphate linkage) | 5.39 ul | 556 ng/ul | 2996.8 ng/reaction |
| NEB2 buffer | 2 ul | 10x | 1x |
| RNA 5' Pyrophosphohydrolase | 2 ul | 5 U/ul | 10 U |
| NF H$_2$O | 10.61 ul | | |
| Total | 20 ul | | |

TABLE 20

| Number of Cycles | Step | Temp (° C.) | Time |
|---|---|---|---|
| 1 | Decapping | 37 | 1:00:00 |

TABLE 21

| Reagent | Volume | Stock Concentration | Final Concentration |
|---|---|---|---|
| Decapped RNA strand (SEQ ID NO: 30) | 1.5 ul | 166 ng/ul | 250 ng/reaction |
| T4 RNA ligase 1 reaction buffer | 2 ul | 10x | 1x |
| non-RNA polynucleotide (30 SpC3 spacers attached to the 5' end of SEQ ID NO: 31 which was attached at the 3' end to four iSp18 spacers which were attached at the opposite end to the 5' end of SEQ ID NO: 32 which was attached at the 3' end to four 5-nitroindoles which were attached at the opposite end to the RNA sequence | 2.4 ul | 50 uM | 8.33 uM |
| ATP | 0.4 ul | 50 mM | 1 mM |
| NF H$_2$O | 0.8 ul | | |
| T4 RNA ligase 1 | 2.9 ul | 10 U/ul | 29 U |
| PEG 8k | 10 ul | 50% | 25% |
| Total | 20 ul | | |

TABLE 22

| Number of Cycles | Step | Temp (° C.) | Time |
|---|---|---|---|
| 1 | Ligation | 16 | 4:00:00 |

Results

The TBE-Urea denaturing gel (See FIG. 17) was used to analyse the success of the decapping of the RNA strand (SEQ ID NO: 30) and subsequent ligation with the non-RNA polynucleotide (30 SpC3 spacers attached to the 5' end of SEQ ID NO: 31 which was attached at the 3' end to four iSp18 spacers which were attached at the opposite end to the 5' end of SEQ ID NO: 32 which was attached at the 3' end to four 5-nitroindoles which were attached at the opposite end to the RNA sequence CAAGGG). Lane 4 of FIG. 17 showed an additional band (labelled C) which was observed above the level of the RNA strand (SEQ ID NO: 30, control shown in lane 2 and labelled A) indicating that successful ligation of the non-RNA polynucleotide (30 SpC3 spacers attached to the 5' end of SEQ ID NO: 31 which was attached at the 3' end to four iSp18 spacers which were attached at the opposite end to the 5' end of SEQ ID NO: 32 which was attached at the 3' end to four 5-nitroindoles which were attached at the opposite end to the RNA sequence CAAGGG) occurred with ~40% efficiency.

Example 7

This example shows how a 2D (RNA-sense and DNA-antisense) library was prepared from cellular mRNA extracted from *Saccharomyces cerevisiae* to allow DNA helicase controlled movement of native *Saccharomyces cerevisiae* mRNA strands through a nanopore.

Materials and Methods

A 2D (RNA-sense and DNA-antisense) library was prepared from cellular mRNA extracted from *Saccharomyces cerevisiae* by ligating a hairpin to the 3' of the mRNA, decapping the 5' end of the mRNA, reverse transcribing to create a DNA complement, and ligating a non-RNA polynucleotide to the 5' end of the mRNA.

Ligate 3' Hairpin

PolyA+ mRNA from *Saccharomyces cerevisiae* was purchased from Clontech. A hairpin that hybridises to the polyA tail of the mRNA was ligated to the mRNA by mixing the reagents shown in Table 23 below and placing the mixture in a thermocycler with the program shown in Table 24 below. The mixture was then purified using Agencourt Ampure SPRI beads at a ratio of 1.8 μL SPRI beads per μL of sample and eluted in 16 ul of NF H$_2$O.

TABLE 23

| Reagent | Volume | Stock Concentration | Final Concentration |
|---|---|---|---|
| polyA+ mRNA | 0.5 ul | 1 ug/ul | 500 ng |
| polyT hairpin (SEQ ID NO: 29 is attached at its 5' end to a phosphate group and is attached at its 3' end to four iSpC3 spacers which are attached at the opposite end to the 5' end of SEQ ID NO: 28) | 0.4 ul | 25 uM | 1 uM |
| T4 DNA ligase buffer | 4 ul | 5 x | 1 x |
| T4 DNA ligase | 1 ul | 2000 U/ul | 2000 U |
| NF H$_2$O | 14.1 ul | | |
| Total | 20 ul | | |

TABLE 24

| Number of Cycles | Step | Temp (° C.) | Time |
|---|---|---|---|
| 1 | Ligate | 16 | 0:30:00 |

Decap

Prior to ligating the non-RNA polynucleotide to the 5' end of the RNA strand (SEQ ID NO: 30), which has a 7-methylguanosine cap connected to its 5' end via a 5' to 5' triphosphate linkage, the cap was enzymatically removed by RNA-5'-pyrophosphohydrolase (RppH). Decapping was achieved by mixing the reagents in Table 25 below and placing the mixture in a thermocycler set to the program in table 26 below. The resulting reaction mixture was then purified using Agencourt Ampure SPRI beads at a ratio of 1.8 μL SPRI beads per L of sample and eluted in 12 ul of NF H$_2$O.

TABLE 25

| Reagent | Volume | Stock Concentration | Final Concentration |
|---|---|---|---|
| Yeast polyA+ mRNA (Clontech) | 16 ul | 28 ng ug/ul | 500 ng/reaction |
| NEB2 buffer | 2 ul | 10x | 1x |
| RNA 5' Pyrophosphohydrolase | 2 ul | 5 U/ul | 10 U |
| Total | 20 ul | | |

TABLE 26

| Number of Cycles | Step | Temp (° C.) | Time |
|---|---|---|---|
| 1 | Decapping | 37 | 1:00:00 |

RT

After decapping, reverse transcription was performed using Life Technologies Super Script II: reagents in Table 27 below were mixed according to the manufacturer's protocol and placed on a thermocycler set to the program in Table 28.

TABLE 27

| Reagent | Volume | Stock Concentration | Final Concentration |
|---|---|---|---|
| 3B (DNA/RNA 3B) after reverse | 12 ul | ~20 ng/ul | 240 ng/reaction |
| dNTPs | 1 ul | 10 uM each | 0.5 uM |
| First-Strand Buffer | 4 ul | 5x | 1x |
| 0.1M DTT | 2 ul | 0.1M | 0.01M |
| Super Script II | 1 ul | 200 U/ul | 200 U |
| Total | 20 ul | | |

TABLE 28

| Number of Cycles | Step | Temp (° C.) | Time |
|---|---|---|---|
| 1 | Reverse Transcription | 42 | 0:50:00 |
| 2 | Denaturation | 70 | 0:15:00 |

The mixture was then purified using Agencourt Ampure SPRI beads at a ratio of 1.8 μL SPRI beads per μL of sample and eluted into 10 ul of NF H$_2$O.

Non-RNA Polynucleotide Ligation

The non-RNA polynucleotide (30 SpC3 spacers attached to the 5' end of SEQ ID NO: 31 which was attached at the 3' end to four iSp18 spacers which were attached at the opposite end to the 5' end of SEQ ID NO: 32 which was attached at the 3' end to four 5-nitroindoles which were attached at the opposite end to the RNA sequence CAAGGG) was ligated to the reverse-transcribed mRNA by mixing the reagents listed in a Table 29 and placing the mixture in a thermocycler set to the program in Table 30. The sample produced after non-RNA polynucleotide ligation was known as Sample 7A.

A 5' leader was ligated by

TABLE 29

| Reagent | Volume | Stock Concentration | Final Concentration |
|---|---|---|---|
| Reverse-transcribed mRNA | 10.0 ul | | |
| Non-RNA polynucleotide (described above) | 1.2 ul | 50 uM | 2 ul |
| T4 RNA ligase buffer | 3.0 ul | 10x | 1x |
| ATP | 0.6 ul | 50 mM | 1 mM |
| 8k PEG | 12.0 ul | 50% | |
| T4 RNA Ligase 1 | 3.2 ul | 10 U/ul | |
| Total | 30.0 ul | | |

TABLE 30

| Number of Cycles | Step | Temp (° C.) | Time |
|---|---|---|---|
| 1 | Ligate | 25 | 0:30:00 |

Hairpin Purification

Sample EX was purified from ligase and unreacted components via a sequence specific tether and Lifetech MyOne C1 streptavidin beads.

Sample 7A was hybridized to a tether (/5desthiobiotin/TT/iSp18/iSp18//iSp18//iSp18//iSp18/iSp18/(SEQ ID NO: 65)/iSp18//iSp18//iSp18//iSp18//iSp18//iSp18/TT/3 CholTEG/) by mixing 1.25 ul of 100 uM tether with 30 ul of Sample 7A and 8.75 ul of NF H$_2$O and incubating the mixture for 15 min at room temperature.

Using a magnetic rack, 20 ul of MyOne C1 streptavidin beads were washed with 200 ul of 1× Binding and washing buffer (B&W buffer) as specified by the manufacturer then resuspended in 40 ul of 2× B&W buffer.

2× B& W Buffer Specified by Lifetech:
10 mM TRIS-HCl pH 7.5
1 mM EDTA
2 M NaCl 40 ul of tethered Sample 7A was added to 40 ul of streptavidin beads and incubated on a roller for 15 minutes. The solution was then placed on a magnetic rack and washed twice with 1× B&W buffer per manufacturer's instructions. The sample was eluted from the streptavidin beads by adding 15 uL of 133 uM biotin in H$_2$O to the beads and heating to 37 C for 10 min. The tube was quickly placed on a magnetic rack and the supernatant was removed from the beads. This product is the purified sample and was known as Sample 7B.

Electrophysiology

Sample 7B (9 µl) was hybridised to a tethering oligo by mixing 3 ul of (1 uM tethering oligo (SEQ ID NO: 66/iSp18//iSp18//iSp18//iSp18//iSp18//iSp18/TT/3CholTEG/), 750 mM KCl, 125 mM KPhos Buffer pH 7, and 5 mM EDTA) and incubating the mixture at room temperature for 20 minutes.

This tethered Sample 7B was then incubated with 2 µl of 17.4 µM T4 Dda (E94C/F98W/C109A/C136A/K194L/A360C (SEQ ID NO: 8 with mutations E94C/F98W/C109A/C136A/K194L/A360C and then (ΔM1)G1)) for 15 minutes. 2.1 µl of 800 µM TMAD was then added to the incubated mixture and kept at room temperature for 10 min. This sample was then diluted into buffer (282 µL of 500 mM KCl, 25 mM potassium phosphate pH 8.0) and mixed with 2 ul of (70 uM ATP and 75 uM MgCl$_2$).

Electrical measurements were acquired from single MspA nanopores inserted in block co-polymer in buffer (25 mM K Phosphate buffer, 150 mM Potassium Ferrocyanide, 150 mM Potassium Ferricyanide~pH 8.0). After achieving a single pore inserted in the block co-polymer, then buffer (2 mL, 25 mM K Phosphate buffer, 150 mM Potassium Ferrocyanide, 150 mM Potassium Ferricyanide, pH 8.0) was flowed through the system to remove any excess MspA nanopores.

An excess of buffer (500 mM KCl, 25 mM potassium phosphate pH 8.0) was flowed through the system prior to the addition of sample. Finally, T4 Dda-E94C/A360C bound to sample 3A was then added to the nanopore system, the experiment was run at −120 mV and helicase-controlled DNA movement monitored.

Results

FIG. 19 shows an ionic current recording from a single nanopore when sample 7B was added. The electrophysiology experiment showed good throughput, with 2D strands of varying lengths (corresponding to different native cellular mRNA transcript lengths). FIG. 19 also demonstrates that RNA has a different mean amplitude and range versus DNA. Thus, RNA and DNA can be differentiated from each other as a function of mean amplitude and range even when the RNA and DNA sequences are the same.

Example 8

This example shows how a DNA-containing leader was attached to messenger RNA (mRNA) to facilitate loading of a DNA helicase, Hel308Mbu-E284C/S615C (SEQ ID NO: 8 with mutations E284C/S615C), and subsequent helicase controlled movement of the RNA through a nanopore. The 1.9 kb mRNA was purchased from Trilink Biotech. The DNA-containing leader was ligated to the 3' end of the mRNA. Hel308 was then loaded onto a DNA binding site in the leader and the substrate was analysed by the nanopore.

Materials and Methods

A DNA-containing leader pre-annealed with several oligos (SEQ ID NO: 35 (which has a 5' phosphate) was attached at its 3' end to four iSp18 spacers which are attached at the opposite end to the 5' end of SEQ ID NO: 36, which is attached at its 5' end to thirty iSpC3 spacers was annealed with SEQ ID NO: 37, 38 and 39 (which has a 3' cholesterol TEG)) and this pre-annealed leader was ligated to the mRNA by mixing the reagents listed in a Table 31 and placing the mixture on a thermocycler set to the program in Table 32.

TABLE 31

| Reagent | Volume | Stock Concentration | Final Concentration |
|---|---|---|---|
| FLuc mRNA (RNA X1, mRNA with an open reading frame of SEQ ID NO: 26 which has a 5'-hexynl-G as the 5' most nucleotide and has a 3' polyA tail) | 2.5 ul | 1 ug/ul | 2500 ng/reaction |
| Leader pre-annealed 1:1:1:1 | 3.5 ul | 2 uM ea | 1x |
| NEB Quick Ligase Buffer (Lifetech) | 4.0 ul | 5 x | 1x |
| NEB Quick Ligase | 2.0 ul | 2,000 U/ul | 4,000 U |
| Splint (SEQ ID NO: 40) | 0.2 ul | 100 uM | 1 uM |
| Water | 8 ul | | |
| Total | 20.2 ul | | |

TABLE 32

| Number of Cycles | Step | Temp (° C.) | Time |
|---|---|---|---|
| 1 | Ligate | 16 | 0:30:00 |

The mixture was then purified using Agencourt Ampure SPRI beads at a ratio of 1.8 µL SPRI beads per µL of sample.

Reverse Transcription

The sample was reverse transcribed using SuperScript 11 kit by mixing the reagents listed in a Table 33 and placing the mixture on a thermocycler set to the program in Table 34.

TABLE 33

| Reagent | Volume | Stock Concentration | Final Concentration |
|---|---|---|---|
| Sample from ligation | 2.2 ul | | 500 ng |
| dNTPs | 1 ul | 10 mM Ea | |
| First Strand Buffer (Lifetech) | 4 ul | 5 x | 1 x |
| DTT | 2 ul | 0.1M | |
| SSII Reverse Transcriptase | 1 ul | | |
| NF H₂O | 9.8 ul | | |
| Total | 20 ul | | |

TABLE 34

| Number of Cycles | Step | Temp (° C.) | Time |
|---|---|---|---|
| 1 | Reverse Transcription | 42 | 0:50:00 |
| 2 | Denaturation | 70 | 0:15:00 |

The mixture was then purified using Agencourt Ampure SPRI beads at a ratio of 1.8 µL SPRI beads per µL of sample. Hel308Mbu-E284C/S615C (SEQ ID NO: 8 with mutations E284C/S615C) was buffer exchanged into 50 mM HEPES pH8, 100 mM KAc using a 7 kda Zeba column. The reverse transcribed RNA sample was mixed with an equal volume of 100 mM HEPES pH8, 200 mM KAc then mixed with Hel308Mbu-E284C/S615C at a mole ratio of 1:100 and buffer exchanged into 100 mM KPhos pH 8, 100 mM NaCl, 5 mM EDTA, 0.1% TWEEN. 20 mM BMOE dissolved in DMF was added to 100 mM KPhos pH 8, 100 mM NaCl, 5 mM EDTA, 0.1% TWEEN to a concentration of 5 mM. This 5 mM BMOE solution was added to the mixture of RNA and Hel308 to a final concentration of 40 uM BMOE. This solution was incubated at room temperature for 2 hours. The solution was then bound to Agencourt Ampure SPRI beads at a ratio of 1.8 µL SPRI beads per µL of sample. Instead of washing the SPRI beads with an EtOH mixture, a single wash with a modified wash buffer of 20% PEG, 2.5M Nacl, 50 mM Tris was used. The sample was eluted in 30 ul of 500 mM KCl 25 mM KPhosphate pH 8. This was known as Sample 6.

Electrophysiology

Sample 6 (4 ul) was mixed with buffer (500 mM KCl 25 mM KPhosphat pH 8, 2 mM ATP, 2 mM MgCl₂, 295 ul)

Electrical measurements were acquired from single MspA nanopores inserted in block co-polymer in buffer (25 mM K Phosphate buffer, 150 mM Potassium Ferrocyanide, 150 mM Potassium Ferricyanide~pH 8.0). After achieving a single pore inserted in the block co-polymer, then buffer (2 mL, 25 mM K Phosphate buffer, 150 mM Potassium Ferrocyanide, 150 mM Potassium Ferricyanide, pH 8.0) was flowed through the system to remove any excess MspA nanopores.

An excess of buffer (500 mM KCl, 25 mM potassium phosphate pH 8.0) was flowed through the system prior to the addition of Sample 6. Finally, Sample 6 was then added to the nanopore system, the experiment was run at −140 mV and helicase-controlled DNA movement was monitored.

Results

This example shows how a DNA-containing leader was attached to messenger RNA (mRNA) to facilitate loading of a DNA helicase, Hel308Mbu-E284C/S615C (SEQ ID NO: 8 with mutations E284C/S615C), and subsequent helicase controlled movement of the RNA was observed. An example of a helicase controlled RNA movement is shown in FIG. 20.

The invention claimed is:

1. A method of characterising a target RNA polynucleotide comprising:
   a) providing (i) an RNA polynucleotide wherein the RNA polynucleotide is modified to comprise a non-RNA polynucleotide and (ii) a DNA helicase enzyme; wherein the DNA helicase comprises a modification to reduce the size of an opening in the polynucleotide binding domain through which in at least one conformational state the RNA polynucleotide can unbind from the helicase
   b) contacting the RNA polynucleotide and DNA helicase enzyme provided in a) with a transmembrane pore such that the DNA helicase controls the movement of the RNA polynucleotide through the transmembrane pore;
   c) taking one or more measurements as the RNA polynucleotide moves with respect to the transmembrane pore, wherein the measurements are indicative of one or more characteristics of the RNA polynucleotide, and thereby characterising the target RNA polynucleotide.

2. A method according to claim 1 wherein the non-RNA polynucleotide comprises a DNA helicase binding site or a DNA adaptor.

3. A method according to claim 2 wherein the DNA helicase binding site or the DNA adaptor comprises a leader sequence.

4. A method according to claim 3 wherein the leader sequence preferentially threads into the pore.

5. A method according to claim 1 wherein the non-RNA polynucleotide is covalently attached to the RNA polynucleotide.

6. A method according to claim 1 wherein the non-RNA polynucleotide is ligated to the RNA polynucleotide.

7. A method according to claim 1 wherein the non-RNA polynucleotide is hybridised to the RNA polynucleotide.

8. A method according to claim 1, wherein the one or more characteristics are selected from (i) length of the RNA polynucleotide, (ii) identity of the RNA polynucleotide, (iii) the sequence of the RNA polynucleotide, (iv) the secondary structure of the RNA polynucleotide and (v) whether or not the RNA polynucleotide is modified.

9. A method according to claim 1 wherein the one or more characteristics of the RNA polynucleotide are measured by electrical and/or optical measurement.

10. A method according to claim 1, wherein step c) comprises measuring the current passing through the transmembrane pore as the RNA polynucleotide moves with respect to the transmembrane pore wherein the current is indicative of one or more characteristics of the RNA polynucleotide and thereby characterising the RNA polynucleotide.

11. A method according to claim 1, wherein the RNA polynucleotide comprises modification by methylation, by oxidation, by damage, with one or more proteins, base analogues or with one or more labels, tags or spacers.

12. A method according to claim 1, wherein the RNA polynucleotide is coupled to the membrane using one or more anchors.

13. A method according to claim 1, wherein the movement is controlled by a series of one of more DNA helicases.

14. A method according to claim 1, wherein the one or more helicases are a) Hel308 helicases, RecD helicases, XPD helicases or Dda helicases (b) helicases derived from any of the helicases in (a); or (c) a combination of any of the helicases in (a) and/or (b).

15. A method according to claim 1, wherein the transmembrane pore is a protein pore or a solid state pore.

16. A method according to claim 15, wherein the transmembrane protein pore is a protein pore and is derived from a hemolysin, leukocidin, *Mycobacterium smegmatis* porin A (MspA), MspB, MspC, MspD, CsgG, lysenin, outer membrane porin F (OmpF), outer membrane porin G (OmpG), outer membrane phospholipase A, *Neisseria* autotransporter lipoprotein (NalP) and WZA.

17. A method of characterising an RNA polynucleotide comprising:
   a) providing (i) an RNA polynucleotide wherein the RNA polynucleotide is modified to comprise a non-RNA polynucleotide, (ii) a DNA helicase enzyme, and (iii) one or more molecular brakes that are derived from helicases and are modified such that they bind the polynucleotide but do not function as a helicase;
   b) contacting the RNA polynucleotide and DNA helicase enzyme provided in a) with a transmembrane pore such that the DNA helicase controls the movement of the RNA polynucleotide through the transmembrane pore;
   c) taking one or more measurements as the RNA polynucleotide moves with respect to the transmembrane pore, wherein the measurements are indicative of one or more characteristics of the RNA polynucleotide, and thereby characterising the RNA polynucleotide.

18. A method according to claim 17 wherein the non-RNA polynucleotide comprises a DNA helicase binding site or a DNA adaptor.

19. A method according to claim 18 wherein the DNA helicase binding site or the DNA adaptor comprises a leader sequence.

20. A method according to claim 19 wherein the leader sequence preferentially threads into the pore.

21. A method according to claim 17 wherein the non-RNA polynucleotide is covalently attached to the RNA polynucleotide.

22. A method according to claim 17 wherein the non-RNA polynucleotide is ligated to the RNA polynucleotide.

23. A method according to claim 17 wherein the non-RNA polynucleotide is hybridised to the RNA polynucleotide.

24. A method according to claim 17, wherein the one or more characteristics are selected from (i) length of the RNA polynucleotide, (ii) identity of the RNA polynucleotide, (iii) the sequence of the RNA polynucleotide, (iv) the secondary structure of the RNA polynucleotide and (v) whether or not the RNA polynucleotide is modified.

25. A method according to claim 17 wherein the one or more characteristics of the RNA polynucleotide are measured by electrical and/or optical measurement.

26. A method according to claim 17, wherein step c) comprises measuring the current passing through the transmembrane pore as the RNA polynucleotide moves with respect to the transmembrane pore wherein the current is indicative of one or more characteristics of the RNA polynucleotide and thereby characterising the RNA polynucleotide.

27. A method according to claim 17, wherein the RNA polynucleotide comprises modification by methylation, by oxidation, by damage, with one or more proteins, base analogues or with one or more labels, tags or spacers.

28. A method according to claim 17, wherein the RNA polynucleotide is coupled to the membrane using one or more anchors.

29. A method according to claim 17, wherein the movement is controlled by a series of one of more DNA helicases.

30. A method according to claim 17, wherein the one or more helicases are a) Hel308 helicases, RecD helicases, XPD helicases or Dda helicases (b) helicases derived from any of the helicases in (a); or (c) a combination of any of the helicases in (a) and/or (b).

31. A method according to claim 17, wherein the transmembrane pore is a protein pore or a solid state pore.

32. A method according to claim 31, wherein the transmembrane protein pore is a protein pore and is derived from a hemolysin, leukocidin, *Mycobacterium smegmatis* porin A (MspA), MspB, MspC, MspD, CsgG, lysenin, outer membrane porin F (OmpF), outer membrane porin G (OmpG), outer membrane phospholipase A, *Neisseria* autotransporter lipoprotein (NalP) and WZA.

* * * * *